US010363344B2

(12) United States Patent
Zamierowski

(10) Patent No.: US 10,363,344 B2
(45) Date of Patent: *Jul. 30, 2019

(54) EXTERNALLY-APPLIED PATIENT INTERFACE SYSTEM AND METHOD WITH A CONTROLLED REGION FOR IMPLANTED OR BURIED BIO-REACTOR

(71) Applicant: KCI Licensing, Inc., San Antonio, TX (US)

(72) Inventor: David S. Zamierowski, Overland Park, KS (US)

(73) Assignee: KCI Licensing, Inc., San Antonio, TX (US)

( * ) Notice: Subject to any disclaimer, the term of this patent is extended or adjusted under 35 U.S.C. 154(b) by 1018 days.

This patent is subject to a terminal disclaimer.

(21) Appl. No.: 14/624,417

(22) Filed: Feb. 17, 2015

(65) Prior Publication Data
US 2015/0157774 A1 Jun. 11, 2015

Related U.S. Application Data

(63) Continuation-in-part of application No. 13/181,399, filed on Jul. 12, 2011, now Pat. No. 8,956,335, which
(Continued)

(51) Int. Cl.
*A61M 1/00* (2006.01)
*A61F 13/02* (2006.01)
(Continued)

(52) U.S. Cl.
CPC ........ *A61M 1/0086* (2014.02); *A61F 13/0203* (2013.01); *A61M 1/0025* (2014.02);
(Continued)

(58) Field of Classification Search
CPC ........ A61M 1/00; A61M 39/02; A61M 27/00; A61F 13/00; A61F 5/00; A61L 15/00
See application file for complete search history.

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 8/1982
AU 745271 12/2002
(Continued)

OTHER PUBLICATIONS

"Algorithm for Abdominal Wall Construction", Plastic and Reconstructive Surgery, Jan. 2000, 207-209.
(Continued)

*Primary Examiner* — Tatyana Zalukaeva
*Assistant Examiner* — Ilya Y Treyger
(74) *Attorney, Agent, or Firm* — Law Office of Mark Brown, LLC; Mark E. Brown; Ryan S. Hinderliter

(57) ABSTRACT

A tissue closure treatment system and method are provided with an external patient interface. A first fluid transfer component FTC.1 comprises a strip of porous material, such as rayon, with liquid wicking properties. FTC.1 can be placed directly on a suture line for transferring fluid exuded therethrough. An underdrape is placed over FTC.1 and includes a slot exposing a portion of same. FTC.2 comprises a suitable hydrophobic foam material, such as polyurethane ether, and is placed over the underdrape slot in communication with FTC.1. Negative pressure is applied to FTC.2 through a connecting fluid transfer component FTC.3. A negative pressure source can comprises a manual device or a power-operated suction device. The tissue closure method includes a manual operating mode using a manual suction device with an automatic shut off for discontinuing suction when a predetermined volume of fluid has been drained. An automatic operating mode utilizes a microprocessor, which can be preprogrammed to respond to various patient and
(Continued)

operating conditions. Alternative embodiments include fluid transfer components with beveled or angle-cut ends, a bio-reactor, internal organ applications and corresponding closure methods.

8 Claims, 60 Drawing Sheets

Related U.S. Application Data is a continuation of application No. 11/242,508, filed on Oct. 3, 2005, now Pat. No. 7,976,519, which is a continuation-in-part of application No. 10/409,225, filed on Apr. 8, 2003, now Pat. No. 6,936,037, which is a continuation-in-part of application No. 10/334,766, filed on Dec. 31, 2002, now Pat. No. 6,951,553.

(51) Int. Cl.
  *A61M 39/02* (2006.01)
  *A61M 27/00* (2006.01)
  *A61F 13/00* (2006.01)
  *A61F 5/00* (2006.01)
  *A61L 15/00* (2006.01)

(52) U.S. Cl.
  CPC ........ *A61M 1/0027* (2014.02); *A61M 1/0029* (2014.02); *A61M 1/0031* (2013.01); *A61M 1/0088* (2013.01); *A61M 1/0092* (2014.02); *A61M 2205/05* (2013.01); *A61M 2205/50* (2013.01); *A61M 2230/00* (2013.01)

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. |
| 3,115,138 A | 12/1963 | McEvenny et al. |
| 3,367,332 A | 2/1968 | Groves |
| 3,520,300 A | 7/1970 | Flower |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 3,981,051 A | 9/1976 | Brumlik |
| 4,080,970 A | 3/1978 | Miller |
| 4,096,853 A | 6/1978 | Weigand |
| 4,139,004 A | 2/1979 | Gonzalez |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,248,232 A | 2/1981 | Engelbrecht et al. |
| 4,256,109 A | 3/1981 | Nichols |
| 4,259,959 A | 4/1981 | Walker |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errade et al. |
| 4,382,441 A | 5/1983 | Svedman |
| 4,392,853 A | 7/1983 | Muto |
| 4,392,858 A | 7/1983 | George et al. |
| 4,419,093 A | 12/1983 | Deaton |
| 4,419,097 A | 12/1983 | Rowland |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vailancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,339 A | 8/1986 | Hasslinger |
| 4,605,399 A | 8/1986 | Weston et al. |
| 4,608,041 A | 8/1986 | Nielson |
| 4,640,688 A | 2/1987 | Hauser |
| 4,655,754 A | 4/1987 | Richmond et al. |
| 4,664,662 A | 5/1987 | Webster |
| 4,696,301 A | 9/1987 | Barabe |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,775,909 A | 10/1988 | Inoue |
| 4,787,888 A | 11/1988 | Fox |
| 4,826,494 A | 5/1989 | Richmond et al. |
| 4,828,546 A | 5/1989 | McNeil et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,976,726 A | 12/1990 | Haverstock |
| 4,985,019 A | 1/1991 | Michelson |
| 5,007,921 A | 4/1991 | Brown |
| 5,007,936 A | 4/1991 | Woolson |
| 5,019,083 A | 5/1991 | Klapper et al. |
| 5,037,397 A | 8/1991 | Kalt et al. |
| 5,045,054 A | 9/1991 | Hood et al. |
| 5,045,075 A | 9/1991 | Ersek |
| 5,086,170 A | 2/1992 | Luheshi et al. |
| 5,092,858 A | 3/1992 | Benson et al. |
| 5,100,396 A | 3/1992 | Zamierowski |
| 5,112,338 A | 5/1992 | Anspach, III |
| 5,134,994 A | 8/1992 | Say |
| 5,139,023 A | 8/1992 | Stanley et al. |
| 5,149,331 A | 9/1992 | Ferdman et al. |
| 5,167,613 A | 12/1992 | Karami et al. |
| 5,169,399 A | 12/1992 | Ryland et al. |
| 5,176,663 A | 1/1993 | Svedman et al. |
| 5,215,522 A | 6/1993 | Page et al. |
| D337,639 S | 7/1993 | Beckman |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,291,887 A | 3/1994 | Stanley et al. |
| 5,298,015 A | 3/1994 | Komatsuzaki et al. |
| 5,318,570 A | 6/1994 | Hood et al. |
| 5,342,376 A | 8/1994 | Ruff |
| 5,344,415 A | 9/1994 | Debusk et al. |
| 5,358,494 A | 10/1994 | Svedman |
| 5,383,897 A | 1/1995 | Wholey |
| 5,423,885 A | 6/1995 | Williams |
| 5,437,622 A | 8/1995 | Carion |
| 5,437,651 A | 8/1995 | Todd et al. |
| 5,507,833 A | 4/1996 | Bohn |
| 5,522,901 A | 6/1996 | Thomas et al. |
| 5,527,293 A | 6/1996 | Zamierowski |
| D372,309 S | 7/1996 | Heldreth |
| 5,549,584 A | 8/1996 | Gross |
| 5,556,375 A | 9/1996 | Ewall |
| 5,580,353 A | 12/1996 | Mendes et al. |
| 5,584,859 A | 12/1996 | Brotz |
| 5,607,388 A | 3/1997 | Ewall |
| 5,630,819 A | 5/1997 | Ashby et al. |
| 5,636,643 A | 6/1997 | Argenta et al. |
| 5,645,081 A | 7/1997 | Argenta et al. |
| 5,716,360 A | 2/1998 | Baldwin et al. |

(56) References Cited

U.S. PATENT DOCUMENTS

| | | |
|---|---|---|
| 5,738,686 A | 4/1998 | Kubein-Meesenburg |
| 5,785,700 A | 7/1998 | Olson |
| 5,800,546 A | 9/1998 | Marik et al. |
| 5,827,246 A | 10/1998 | Bowen |
| 5,846,244 A | 12/1998 | Cripe |
| 5,911,222 A | 6/1999 | Lawrence et al. |
| 5,921,972 A | 7/1999 | Skow |
| 5,931,855 A | 8/1999 | Buncke |
| 5,941,859 A | 8/1999 | Lerman |
| 6,071,267 A | 6/2000 | Zamierowski |
| 6,113,618 A | 9/2000 | Nic |
| 6,126,659 A | 10/2000 | Wack |
| 6,135,116 A | 10/2000 | Vogel et al. |
| 6,142,982 A | 11/2000 | Hunt et al. |
| 6,146,423 A | 11/2000 | Cohen et al. |
| 6,159,246 A | 12/2000 | Mendes et al. |
| 6,174,306 B1 | 1/2001 | Fleischmann |
| 6,179,804 B1 | 1/2001 | Satterfield |
| 6,190,391 B1 | 2/2001 | Stubbs |
| 6,190,392 B1 | 2/2001 | Vandewalle et al. |
| 6,203,563 B1 | 3/2001 | Fernandez |
| 6,241,747 B1 | 6/2001 | Ruff |
| 6,270,517 B1 | 8/2001 | Brotz |
| RE37,358 E | 9/2001 | Del Rio et al. |
| 6,287,316 B1 | 9/2001 | Agarwal et al. |
| 6,293,929 B1 | 9/2001 | Smith et al. |
| 6,345,623 B1 | 2/2002 | Heaton et al. |
| 6,355,215 B1 | 3/2002 | Poggie et al. |
| 6,377,653 B1 | 4/2002 | Lee et al. |
| 6,398,767 B1 | 6/2002 | Fleischmann |
| 6,430,427 B1 | 8/2002 | Lee et al. |
| 6,488,643 B1 | 12/2002 | Tumey |
| 6,493,568 B1 | 12/2002 | Bell et al. |
| 6,500,209 B1 | 12/2002 | Kolb |
| 6,503,281 B1 | 1/2003 | Mallory |
| 6,540,705 B2 | 4/2003 | Norstrem et al. |
| 6,553,998 B2 | 4/2003 | Heaton et al. |
| 6,589,285 B2 | 7/2003 | Penenberg |
| 6,620,132 B1 | 9/2003 | Skow |
| 6,626,891 B2 | 9/2003 | Ohmstede |
| 6,645,226 B1 | 11/2003 | Jacobs et al. |
| 6,669,735 B1 | 12/2003 | Pelissier |
| 6,685,681 B2 | 2/2004 | Lockwood et al. |
| 6,695,823 B1 | 2/2004 | Lina et al. |
| 6,695,824 B2 | 2/2004 | Howard et al. |
| 6,726,706 B2 | 4/2004 | Dominguez |
| 6,752,794 B2 | 6/2004 | Lockwood et al. |
| 6,764,462 B2 | 7/2004 | Risk et al. |
| 6,800,074 B2 | 10/2004 | Henley et al. |
| 6,814,079 B2 | 11/2004 | Heaton et al. |
| 6,824,533 B2 | 11/2004 | Risk et al. |
| 6,828,468 B2 | 12/2004 | Ansmann et al. |
| 6,856,821 B2 | 2/2005 | Johnson |
| 6,860,903 B2 | 3/2005 | Mears et al. |
| 6,936,037 B2 | 8/2005 | Bubb |
| 6,951,553 B2 | 10/2005 | Bubb et al. |
| 6,953,480 B2 | 10/2005 | Mears et al. |
| 6,991,643 B2 | 1/2006 | Saadat |
| 7,070,584 B2 | 7/2006 | Johnson et al. |
| 7,105,021 B2 | 9/2006 | Edens et al. |
| 7,108,683 B2 | 9/2006 | Zamierowski |
| 7,381,211 B2 | 6/2008 | Zamierowski |
| 7,645,269 B2 | 1/2010 | Zamierowski |
| 7,976,519 B2 | 7/2011 | Bubb et al. |
| 2002/0022861 A1 | 2/2002 | Jacobs et al. |
| 2002/0029063 A1 | 3/2002 | Wittman |
| 2002/0143286 A1 | 10/2002 | Tumey |
| 2002/0198503 A1 | 12/2002 | Risk |
| 2002/0198504 A1* | 12/2002 | Risk, Jr. ............ A61M 1/0058 604/318 |
| 2004/0006319 A1 | 1/2004 | Lina et al. |
| 2005/0043818 A1 | 2/2005 | Bellon et al. |

FOREIGN PATENT DOCUMENTS

| | | |
|---|---|---|
| AU | 755496 | 12/2002 |
| CA | 2005436 | 6/1990 |
| DE | 2640413 | 3/1978 |
| DE | 4306478 | 9/1994 |
| DE | 29504378 | 9/1995 |
| EP | 0100148 | 2/1984 |
| EP | 0117632 | 9/1984 |
| EP | 0161865 | 11/1985 |
| EP | 0358302 | 3/1990 |
| EP | 1018967 | 8/2004 |
| EP | 1513478 | 12/2009 |
| GB | 692578 | 6/1953 |
| GB | 2195255 | 4/1988 |
| GB | 2197789 | 6/1988 |
| GB | 2220357 | 1/1990 |
| GB | 2235877 | 3/1991 |
| GB | 2333965 | 8/1999 |
| GB | 2329127 | 8/2000 |
| JP | 4129536 | 4/1992 |
| SG | 71559 | 4/2002 |
| WO | 80/02182 | 10/1980 |
| WO | 87/04626 | 8/1987 |
| WO | 90/10424 | 9/1990 |
| WO | 93/09727 | 5/1993 |
| WO | 94/20041 | 9/1994 |
| WO | 96/05873 | 2/1996 |
| WO | 97/18007 | 5/1997 |
| WO | 99/13793 | 3/1999 |
| WO | 04/60148 | 7/2004 |
| WO | 2004060148 | 7/2004 |

OTHER PUBLICATIONS

"All Silicone Jackson Pratt Style Flat Drain", C. Daniel Medical, Inc., retrieved from internet Mar. 15, 2007, http://www.cdanielmedical.com/flat-drain.html, 1-2.

"All Silicone Jackson Pratt Style Round Drain", C. Daniel Medical, Inc., retrieved from internet Mar. 15, 2007, http://www.cdanielmedical.com/round-drain.html, 1-2.

"Antibacterial Silver Wound Dressing, Bandage, Gauze and Adhesive Strips", Silverlon Woundcare Products; http://www.silverlon.com/wound.htm; retrieved from Internet Jul. 27, 2006, 1-5.

"Hydrophobic Rigid Canisters", http://www.bemishealthcare.com/docs/anisterHydrophobic; Retrieved from Internet Mar. 15, 2007, 1-1.

"International Preliminary Examination Report and Search Report", PCT/GB96/02802, dated Jan. 15, 1998 and dated Apr. 29, 1997.

"International Search Report", PCT/GB98/02713, dated Jan. 8, 1999.

"International Search Report", PCT/GB95/01983, dated Nov. 23, 1995.

"International Search Report and Written Opinion", PCT/US2013/069756, dated Jan. 30, 2014, 1-10.

"NPD 1000 Negative Pressure Wound Therapy System", Kalypto Medical: www.kalyptomedical.com, Sep. 2008, 1-4.

"Occlude", Merriam Webster Online Dictionary; http://www.merriam-webster.com/dictionary/occlude; retrieved from internet Mar. 4, 2008.

"Patentee's Observations on the Oppositions", KCI Licensing, Inc. Response to Opponents Smith & Nephew, Inc., and Paul Hartmann Aktiengesellschaft Oppositions, Apr. 21, 2011, 1-15.

"PCT Written Opinion", PCT/GB98/02713, dated Jun. 8, 1999.

"PCT Written Opinion", PCT/GB96/028202, dated Sep. 3, 1997.

"Search Report and Written Opinion of the International Search Authority", International Application No. PCT/US06/38855 filed Oct. 3, 2006, report dated Aug. 8, 2007.

"Smith & Nephew, Inc. Opposition against EP 1,513,478", Sep. 16, 2010.

"V.A.C. Therapy Clinical Guidelines: A Reference Source for Clinicians", KCI: The Clinical Advantage, Jul. 2007, 1-92, 28.

Aktiengesellschaft, "Opposition to EP1513478", Sep. 16, 2010.

(56) References Cited

OTHER PUBLICATIONS

Ambrosio, et al., "V.A.C. GranuFoam Silver Dressing a New Antimicrobial Silver Foam Dressing Specifically Engineered for Use with V.A.C. Therapy", http://silverlon.com/fda.html, retrieved from the internet Jul. 27, 2006, 1-71.

Anderson, et al., "Design of Tissue Engineering Scaffolds as Delivery Devices for Mechanical and Mechanically Modulated Signals", Tissue Engineering, vol. 13, No. 10, 2007, 2525-2539.

Arcand, et al., "Negative Pressure Wound Therapy and Its Application to Orthopaedics. Part II: Clinical Application", Osteo Trauma Care, 2006, 254-258.

Argenta, et al., "Vacuum-Assisted Closure: A New Method for Wound Control and Treatment: Clinical Experience", Annals of Plastic Surgery, vol. 38, No. 6, Jun. 1997, 563-576.

Armstrong, et al., "Planter Pressure Changes Using a Novel Negative Pressure Wound Therapy Technique", Journal of the Am. Podiatric Med. Assoc., vol. 94, No. 5, Sep. 2004, 456-460.

Arnljots, et al., "Irrigation Treatment in Split-Thickness Skin Grafting of Intractable Leg Ulcers", Scand J. Plast. Reconstr. Surg., 19, Nov. 19, 1984, 211-213.

Bagautdinov, "Variant of External Aspiration in the Treatment of Purulent Diseases of Soft Tissues", Ministry of Higher and Secondary Education of the RSFSR I.N. Ulyanov Chuvash State University, 1986, 94-96.

Baig, et al., "Percutaneous Postoperative Intra-Abdominal Abscess Drainage After Elective Colorectal Surgery", Tech Coloproctol, vol. 6, 2002, 159-164.

Barker, et al., "Vacuum Pack Technique of Temporary Abdominal Closure: A 7-Year Experience with 112 Patients", The Journal Trauma: Injury, Infection and Critical Care, vol. 48, No. 2, Feb. 2000, 201-207.

Blackburn, II, MD, "Negative-Pressure Dressings as a bolster for Skin Grafts", Annals of Plastic Surgery, vol. 40, No. 5, May 1998, 453-457.

Gemmiti, et al., "Fluid Flow Increases Type II Collagen Deposition and Tensile Mechanical Properties in Bioreactor-Grown Tissue-Engineered Cartilage", Tissue Engineering, vol. 12, No. 3, 2006, 469-479.

Grauhan, et al., "Prevention of Poststernotomy Wound Infections in Obese Patients by Negative Pressure Wound Therapy", The Journal of Thoracic and Cardiovascular Surgery, vol. 145, No. 5., May 2013, pp. 1387-1392.

Greer, et al., "The Use of Subatmospheric Pressure Dressing Therapy to Close Lymphocutaneous Fistulas of the Groin", British Journal of Plastic Surgery (2000), 53, 484-487.

Gupta, et al., "Guidelines for Managing Pressure Ulcers with Negative Pressure Wound Therapy", Supplement to Advances in Skin and Wound Care, vol. 17, Supp. 2, Nov. 2004, 1-16.

Herte, et al., "Comparative Wound Healing in Animal Subjects Using the Cuba System VS Conventional Surgical instruments", The American Society of Plastic and Reconstructive Surgeons, Nov. 1978, 1-19.

Jeschke, et al., "Development of New Reconstructive Techniques: Use of Integra in Combination with Fibrin Glue and Negative-Pressure Therapy fro Reconstruction of Acute and Chronic Wounds", Departments of General Surgery and Trauma and Reconstructive Surgery, University of Regensburg, Jan. 15, 2003, 525-530.

Jeter, et al., "Managing Draining Wounds and Fistulae: New and Established Methods", Chronic Wound Care: Health Management Publications, 1990, 240-246.

Johnson, "An Improved Technique for Skin Graft Placement Using a Suction Drain", Surgery, Gynecology & Obstetrics, vol. 159, Dec. 1984, 585-586.

Kaplan, et al., "Guidelines for the Management of the Open Abdomen", Supplement to Wounds, Oct. 2005, 1-26.

Khatyr, "Model of the Viscoelastic Behaviour of Skin in vivo and Study of Anisotropy", Skin Research and Technology, vol. 10, 2004, 96-103.

Kostyuchenok, et al., "Vacuum Treatment in the Surgical Management of Purulent Wounds", Vestnik Khirugi, Sep. 1986, 18-21.

Kuznetsov, et al., "Vacuum and Vacuum-Sorption Treatment of open Septic Wounds, Appendix B", II All-Union Conference on Wounds and Wound Infections: Presentation Abstracts Moscow, U.S.S.R., Oct. 29, 1986, 91-92.

Kwan, et al., "A Structural Model to Describe the Nonlinear stress-Strain Behavior for Parallel-Fibered Collagenous Tissues", Journal of Biomechanical Engineering, vol. 111, Nov. 1989, 361-363.

Lago, et al., "Neurobiological Assessment of Regenerative Electrodes for Bidirectional Interfacing Injured Peripheral Nerves", IEEE Transactions on Biomedical Engineering, vol. 54, No. 6, Jun. 2007, 1129-1137.

Laskin, "Minimally Invasive Total Knee Replacement Using a Mini-Mid Vastus Incision Technique and Results", Surgical Technology International, vol. 13, 2004, 231-238.

Latenser, et al., "A Pilot Study Comparing Percutaneous Decompression with Decompressive Laparotomy for Acute Abdominal Compartment Syndrome in Thermal Injury", Journal of Burn Care & Rehab., vol. 23, No. 3, May/Jun. 2002, 190-195.

Lavery, et al., "Emerging Concepts with VAC Therapy", Podiatry Today, vol. 20, Jul. 1, 2007, 1-6.

Letsou, M.D., et al., "Stimulation of Adenylate Cyclase Activity in Cultured Endothelial Cells Subjected to Cyclic Stretch", Journal of Cardiovascular Surgery, 31, 1990, 534-539.

Manwaring, et al., "Characterization of Rat Meningeal Cultures on Materials of Differing Surface Chemistry", Biomaterials, vol. 22, 2001.

Manwaring, et al., "Contact Guidance Induced Organization of Extracellular Matrix", Biomaterials, vol. 25, 2003, 3631-3638.

Masters, "Letter to the Editor", British Journal of Plastic Surgery, vol. 51(3), 1998; Elsevier Science/The British Association of Plastic Surgeons, UK, 267.

Mendez-Eastman, RN, "When Wounds Won't Heal", RN, Jan. 1998, vol. 61(1), Medical Economics Company, Inc., Montvale, NJ, USA, 20-24.

Boersma, et al., "Photogrammetric Wound Measurement with a Three-Camera Vision System", IAPRS, vol. 33, 2000.

Brabmamdam, et al., "Critical Care I", Surg. Forum Abstracts, vol. 207, No. 3S, Sep. 2008, S34-S35.

Brock, et al., "Temporary Closure of Open Abdominal Wounds: The Vacuum Pack", The Am. Surgeon,, Jan. 1995, 30-35.

Brody, et al., "Approaches to Heart Valve Tissue Engineering Scaffold Design", Journal of Biomedical Materials Research Part B: Applied Biomaterials, 2006, 16-43.

Burdette, et al., "Systemic Inflammatory Response Syndrome", eMedicine Critical Care; http://emedicine.medscape.com/article/168943-print, Apr. 16, 2007, 1-19.

Chariker, et al., "Effective Management of Incisional and Cutaneous Fistulae with Closed Suction Wound Drainage", Contemporary Surgery, vol. 34, Jun. 1989, 59-63.

Cheboksary, "Current Problems in Modern Clinical Surgery Interdepartmental Collection", Ministry of Higher and Secondary Education of the RSFSR I.N. Ulyanov Chuvash State University, May 21, 1986, 1-153.

Chinn, et al., "Closed Wound Suction Drainage", The Journal of Foot Surgery, vol. 1, No. 1, 1985, 76-81.

Culliford, et al., "A Novel Technique for Vacuum Assisted Closure Device Application in Noncontiguous Wounds", Journal of Plastic, Reconstructive and Aesthetic Surgery, 2006, 1-2.

Cunningham, "Development of in-vitro Model to Simulate Dermal Wound Bed Interaction with Granufoam and Gauze Dressing Under Sub Atmospheric Pressure", Micro CT Study-Test Cell Development, Report, Jul. 30, 2006, 1-19.

Dattilo, Jr., et al., "Medical Textiles: Application of an Absorbable Barbed Bi-directional Surgical Suture", Journal of Textile and Apparel, Technology and Management, vol. 2, Issue 2, Spring 2002, 1-5.

Davydov, et al., "Bacteriological and Cytological Assessment of Vacuum Therapy of Purulent Wounds", Vestnik Khirurgi, Oct. 1998, 48-52.

(56) References Cited

OTHER PUBLICATIONS

Davydov, et al., "Concepts for the Clinical-Biological Management of the Wound Process in the Treatment of Purulent Wounds by Means of Vacuum Therapy", Vestnik Khirurgi, Jul. 7, 1980, 132-136.
Davydov, et al., "Vacuum Therapy in the Treatment of Purulent Lactation Mastitis", Vestnik Khirurgi, May 14, 1986, 66-70.
Dee, "The Successful Management of a dehisced Surgical Wound with TNP Following Femoropopliteal Bypass", Journal of Wound Care, vol. 16, No. 1, Jan. 2007, 42-44.
Delalleau, et al., "Characterization of the Mechanical Properties of Skin by Inverse Analysis Combined with the Indentation Test", Journal of Biomechanics, vol. 39, 2006, 1603-1610.
Diridollou, et al., "In vivo Model of the Mechanical Properties of the Human Skin Under Suction", Skin Research and Technology, vol. 6, 2000, 214-221.
Dubick, et al., "Issues of Concern Regarding the Use of Hypertonic/Hyperoncotic Fluid Resuscitation of Hemorrahagic Hypotension", Shock, vol. 25, No. 4, 2006, 321-328.
Egnell Minor, "Addition to the User's Manual Concerning Overflow Protection", Industrigaton2, 461, 37 Trollhattan, Feb. 3, 1983, 2.
Egnell Minor, "Egnell Minor Instruction Book, 1st Edition, 300 7502", Feb. 1975, 1-24.
Fong, et al., "Initial Clinical Experience Using a Novel Ultraportable Negative Pressure Wound Therapy Device", Wounds, a Compendium of Clinical Research and Practice, vol. 22 Issue 9., Sep. 2010, 230-236.
Garner, et al., "Vacuum-Assisted Wound Closure Provides Early Fascial Reapproximation in Trauma Patients with Open Abdomens", The Am. Journ. Surg, vol. 182, 2001, 630-638.
Mercier, et al., "Poly(lactide-co-glycolide) microspheres as a moldable scaffold for Cartilage Tissue Engineering", Biomaterials, vol. 26, 2005, 1945-1952.
Meyer, et al., "A New Abdominal Drain for Overflowing Lavage in Instances of Severe Pancreatitis with Persistent Peritoneal Contamination", Surgery, Gynecology & Obstetrics, vol. 165, Sep. 1987.
Meyer, et al., "Selections from Bier's Hyperemic Treatment in Surgery, Medicine, and the Specialties: A Manual of Its Practical Application", W.B. Sunders Co., 2 Ed., 1909, 17-25, 44-64, 90-96, 167-170, and 210-211.
Mikos, et al., "Preparation of Poly(glycolic acid) Bonded Fiber Structures for Cell Attachment and Transplantation", Journal of Biomedical Materials Research, vol. 27, 1993, 183-189.
Miyauchi, et al., "Repair of Incisional Hernia with Prolene Hernia System", The Journal of Medical Investigation, vol. 50, p. 108-111, 2003; received for publication Aug. 8, 2002.
Morykwas, et al., "Vacuum-Assisted Closure: A new Method for Wound Control and Treatment: Animal Studies and Basic Foundation", Annals of Plastic Surgery, vol. 38, No. 6, 1997, 553-562.
"First Examination Report, 2161/DE:MP/2008", pp. 1-2.
Norman, et al., "Methods for Fabrication of Nanoscale Topography for Tissue Engineering Scaffolds", Annals of Biomedical Engineering, vol. 34, No. 1, Jan. 2006, 89-101.
Orringer, et al., "Management of Wounds in Patients with Complex Enterocutaneous Fistulas", Surgery, Gynecology & Obstetrics, vol. 165, Jul. 1987, 79-80.
Pailler-Mattei, et al., "Study of Adhesion Forces and Mechanical Properties of Human Skin in vivo", J. Adhesion Sci. Technol., vol. 18, No. 15-16, 2004, 1739-1758.
Pfister, et al., "Neural Engineering to Produce In Vitro Nerve Constructs and Neurointerface", Neurosurgery: www.neurosurgery-online.com, 2007, 137-142.
Poritz, et al., "Percutaneous Drainge and Ileocolectomy for Spontaneus Intraabdominal Abscess in Chrohn's Disease", J. Gast. Surg., vol. 11, Jan. 19, 2007, 204-207.
Puyana, "Resuscitation of Hypovolemic Shock", Textbook of Critical Care, 5th Ed., Ch. 229, 2005, 1933-1943.

Reckard, et al., "Management of Intraabdominal Hypertension by Percutaneous Catheter Drainage", JVIR, vol. 16, No. 7, Jul. 2005, 1019-1021.
Robledo-Ogazon, et al., "Using the Vacuum Assisted Closure System VAC in the Treatment of Infected Surgical Wounds. Clinical Experience", madigraphic Artemisa, vol. 74, No. 2, Mar.-Apr. 2006, 107-113.
Sachlos, et al., "Making Tissue Engineering Scaffolds Work. Review on the Application of Solid Freeform Fabrication Technology to the Production of Tissue Engineering Scaffolds", European Cells and Materials, vol. 5, 2003, 29-40.
Safronov, "Vacuum Therapy of Trophic Ulcers of the Lower Leg with Simultaneous Autoplasty of the Skin", Ministry of Public Health of the USSR, 1967, 1-50.
Saxena, et al., "Vacuum-Assisted Closure: Microdeformations of Wounds and Cell Proliferation", Plast Reconstr Surg., 114(5), Oct. 2004, 1086-1096.
Schein, et al., "The 'sandwich technique' Management of the Open Abdomen", Br. J. Surg., vol. 73, May 1986, 369-370.
Segvich, et al., "Uniform Deposition of Protein Incorporated Mineral Layer on Three-Dimensional Porous Polymer Scaffolds", Journal of Biomedical Materials Research Part B: Applied Biomaterials 84B(2): <http://hdl.handle.net/2027.42/57926>, May 8, 2007, 340-349.
Sherck, et al., "Covering the "Open Abdomen": A Better Technique", The American Surgeon, vol. 64, Sep. 1998.
Shimko, et al., "Effect of Porosity on the Fluid Flow Characteristics and Mechanical Properties of Tantalum Scaffolds", Journal of Biomedical Materials Research, Part B, Applied Biomaterials, Sep. 24, 2004, 315-324.
Solovev, et al., "The Method of Treatment of Immature External Fistulas in the Upper Gastrointestinal Tract", S.M. Kirov Gorky State Medical Institute, 1987, 1-20.
Solovev, "Treatment and Prevention of Suture Failures After Gastric Resection", S.M. Kirov Gorky State Medical Institute, 1988, 1-55.
Stannard, et al., "Use of negative pressure wound therapy over clean, closed surgical incisions", International Wound Journal, 2012 vol. 9 (Suppl. 1), Aug. 2012, 32-39.
Svedman, "A Dressing Allowing Continuous Treatment of a Biosurface", IRCS Medical Science: Biomedical Technology; Clinical Medicine; Surgery and Transplantation, Jul. 1979, 221.
Svedman, et al., "A Dressing System Providing Fluid Supply and Suction Drainage Used for Continuous or Intermittent Irrigation", Annals of Plastic Surgery, vol. 17, No. 2, Aug. 1986, 125-133.
Svedman, "Irrigation Treatment of Leg Ulcers", The Lancet, vol. 322, Issue 8349, Sep. 3, 1983, 532-534.
Takahashi, et al., "Induction of Pluripotent Stem Cells from Mouse Embryonic and Adult Fibroblast Cultures by Defined Factors", Cell, vol. 126, Aug. 25, 2006, 663-676.
Tan, et al., "Inhibition of Osteocyte Apoptosis by Fluid Flow is Mediated by Nitric Oxide", Biochemical and Biophysical Research Communications, vol. 369, Issue 4, May 16, 2008, 1150-1154.
Tan, et al., "Osteocytes Subjected to Fluid Flow Inhibit Osteoclast Formation and Bone Resorption", Bone, vol. 4, Jul. 27, 2007, 745-751.
Tennant, "The Use of Hyperemia in the Postoperative Treatment of Lesions of the Extremities and Thorax", Jour. A.M.A., May 8, 1915, 1548-1549.
Timmenga, et al., "The Effect of Mechanical Stress on Healing Skin Wounds: An Experimental Study of Rabbits Using Tissue Expansion", British Journal of Plastic Surgery, vol. 44, 1991, 514-519.
Tribble, "An Improved Sump Drain-Irrigation Device of Simple Construction", Arch. Surg., vol. 105, Sep. 1972, 511-513.
Venturi, et al., "Mechanisms and CLinical Applications of the Vacuum-Assisted Closure (VAC) Device", Am. J. Clin. Dermatol., vol. 6 (3), 2005, 185-194.
Walsh, et al., "Directional Neurite Outgrowth is Enhanced by Engineered Meningeal Cell-Coated Substrates", Tissue Engineering, vol. 11, No. 7/8, Mary Ann Liebert, Inc., 2005, 1085-1095.
Wilkes, et al., "3D Strain Measurement in Soft Tissue: Demonstration of a Novel Inverse Finite Element Model Algorithm on MicroCT

(56) References Cited

OTHER PUBLICATIONS

Images of a Tissue Phantom Exposed to Negative Pressure Wound Therapy", Journal of the Mechanical Behavior of Biomedical Materials, Nov. 5, 2008, 1-16.
Yusupov, et al., "Active Wound Drainage", Vestnik Khirurgi, vol. 138, Issue 4, 1987, 42-46.
Zivadinovic, et al., "Vacuum Therapy in the Treatment of Peripheral Blood Vessels", Conference Papers of the 5th Timok Medical Days, Timok Medical Journal, Majdanpek, Copy and Certified Translation, 1986, 161-164.

* cited by examiner

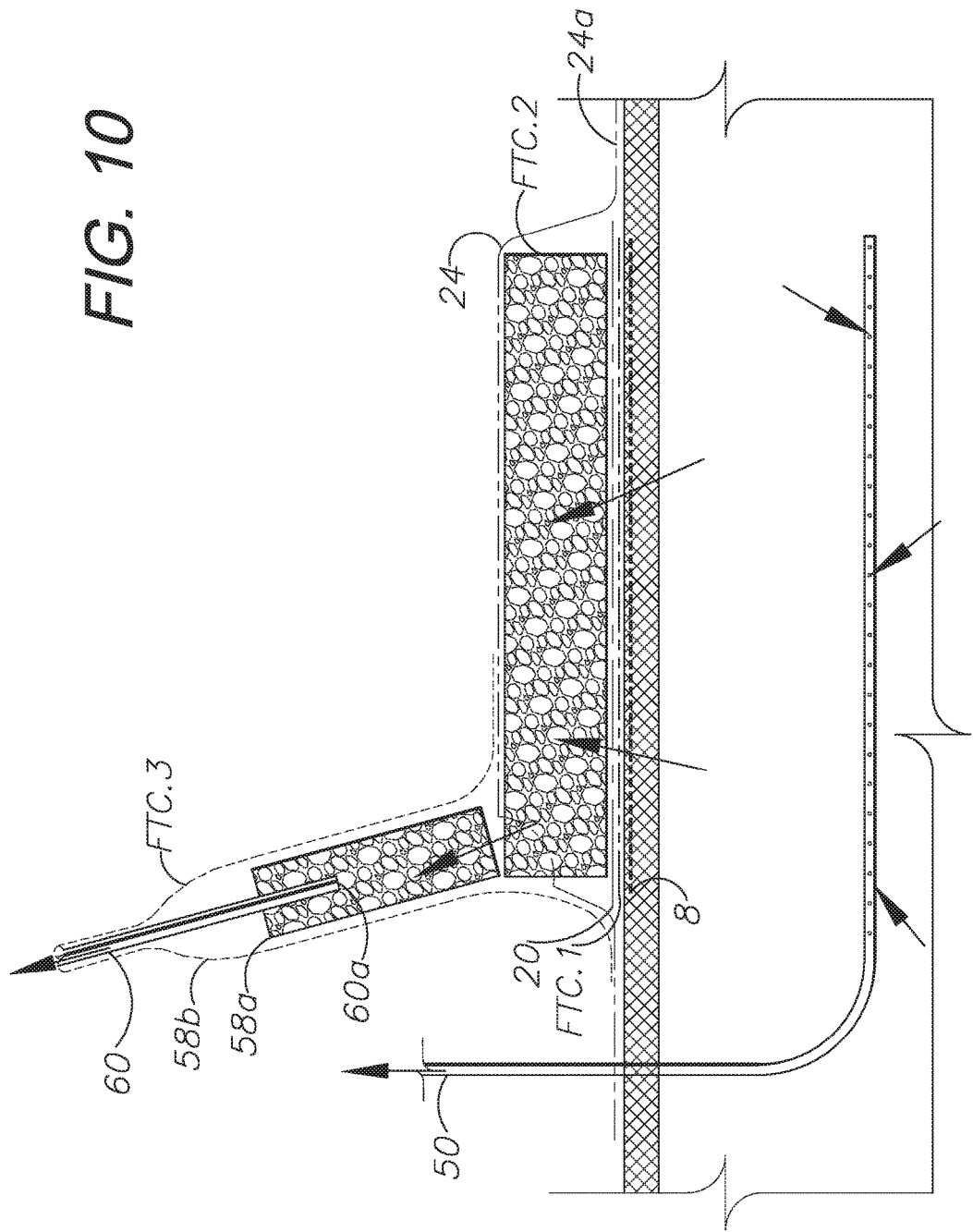

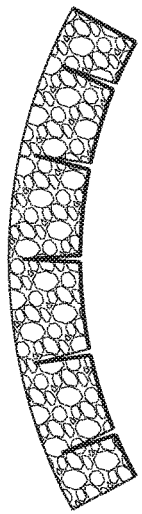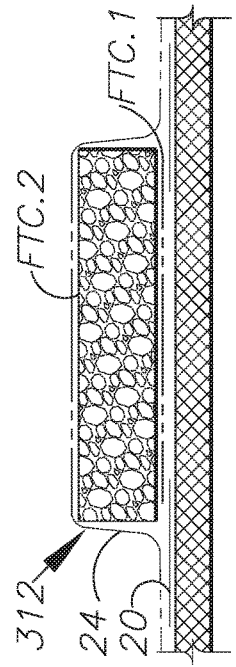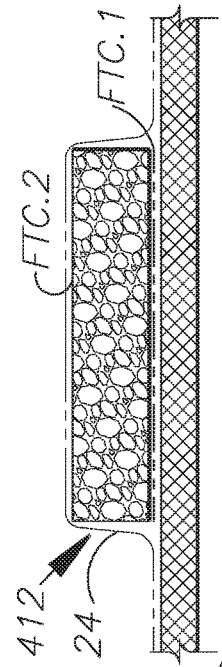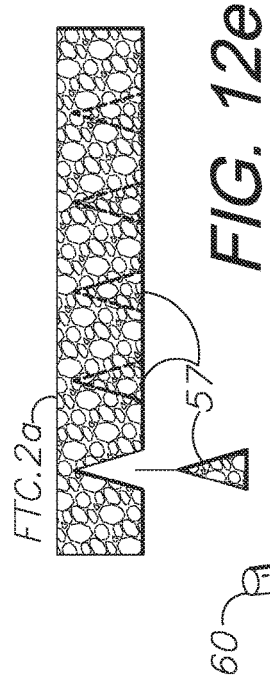

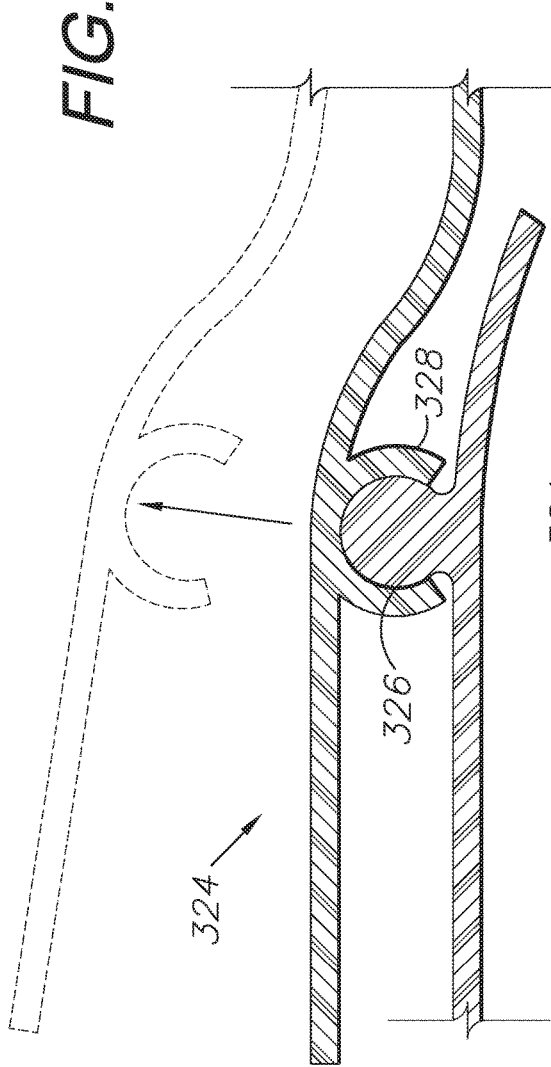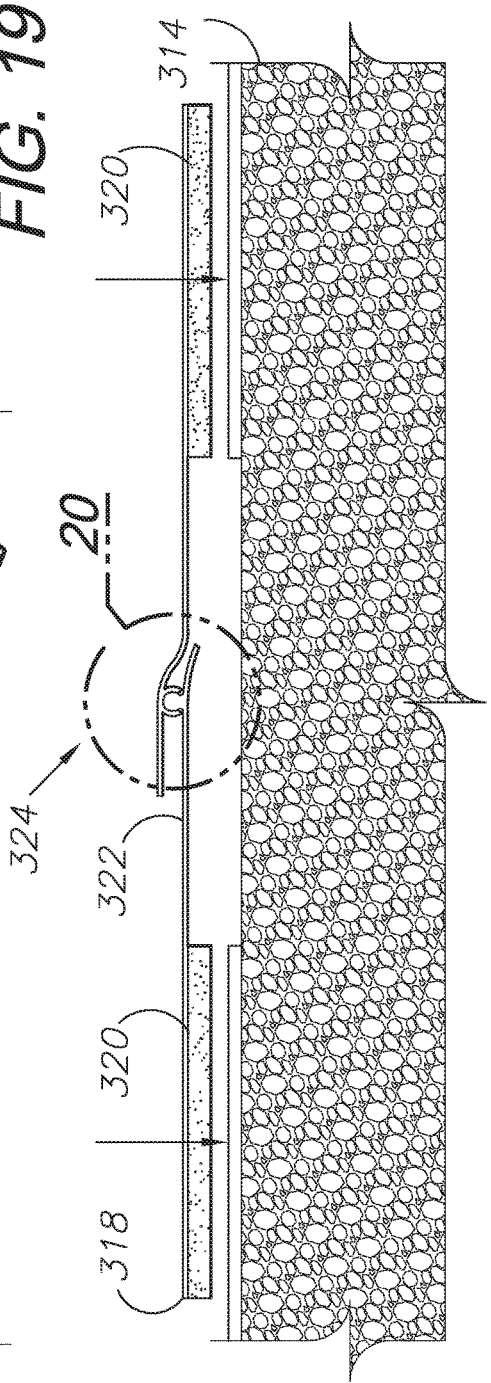

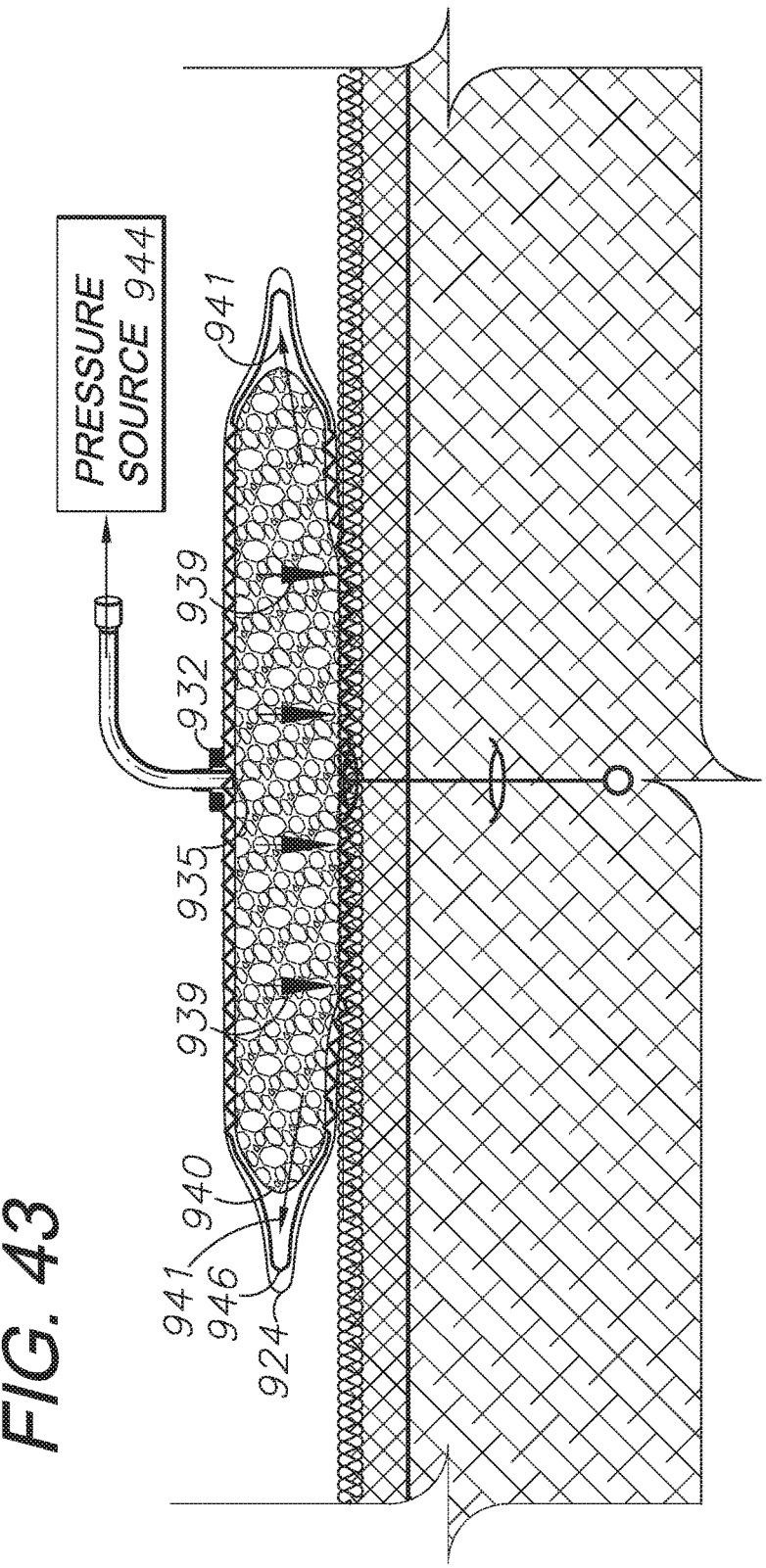

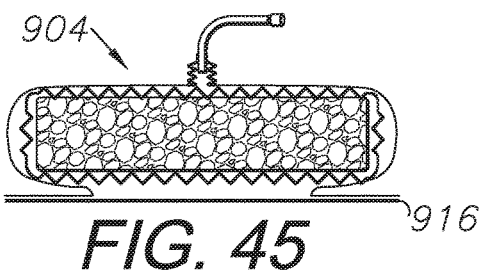
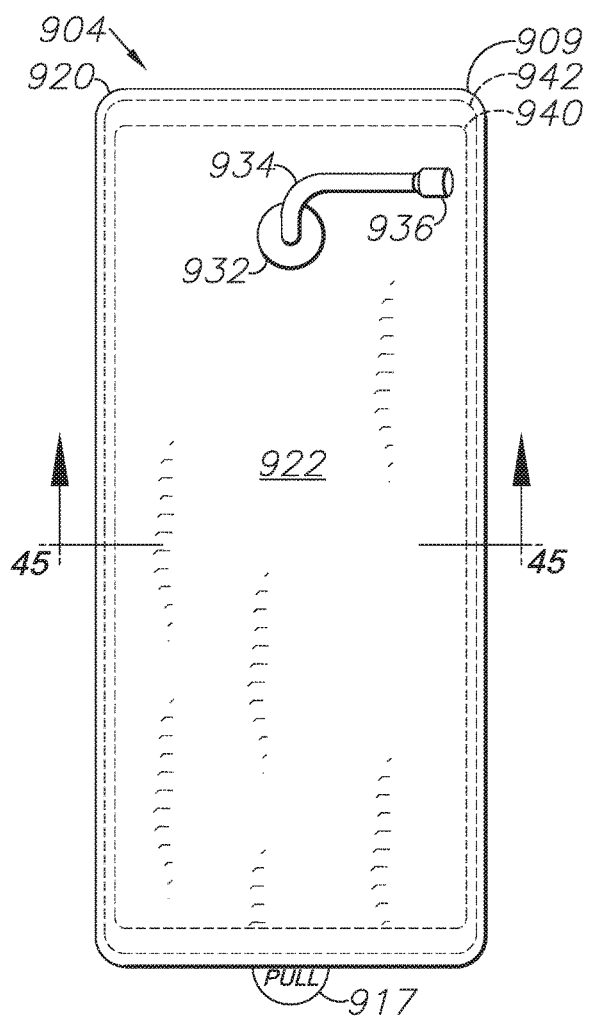
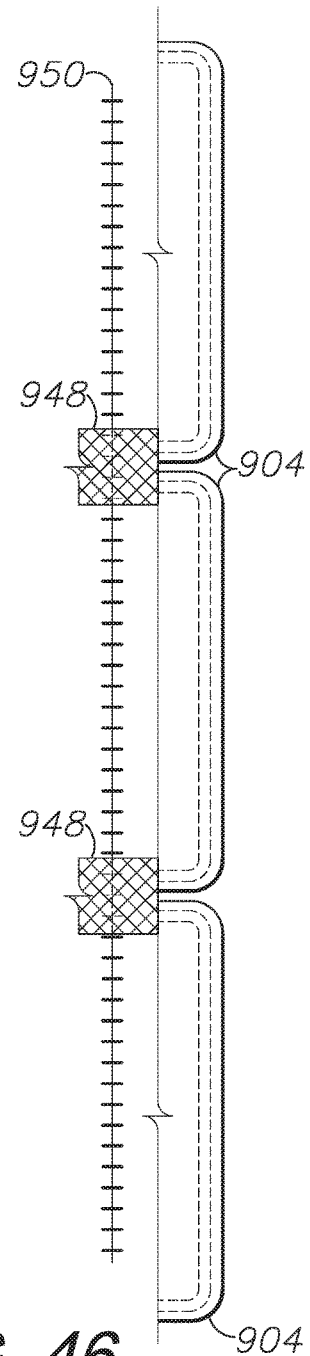
FIG. 45
FIG. 44
FIG. 46

EXTERNALLY-APPLIED PATIENT INTERFACE SYSTEM AND METHOD WITH A CONTROLLED REGION FOR IMPLANTED OR BURIED BIO-REACTOR

CROSS-REFERENCE TO RELATED APPLICATIONS

This application is a continuation-in-part of U.S. patent application Ser. No. 13/181,399, filed Jul. 12, 2011, U.S. Pat. No. 8,956,335, which is a continuation of U.S. patent application Ser. No. 11/242,508, filed Oct. 3, 2005, U.S. Pat. No. 7,976,519, which is a continuation-in-part of U.S. patent application Ser. No. 10/409,225, filed Apr. 8, 2003, U.S. Pat. No. 6,936,037, which is a continuation-in-part of U.S. patent application Ser. No. 10/334,766, filed Dec. 31, 2002, U.S. Pat. No. 6,951,553, all of which are incorporated herein by reference. In addition, U.S. Provisional patent application 62/114,438, filed Feb. 10, 2015 is incorporated by reference.

BACKGROUND OF THE INVENTION

1. Field of the Invention

The present invention relates generally to medical devices and methods for treating closed wounds and incisions and for managing moisture therein, and in particular to a system and method for draining and/or irrigating tissue separations, such as surgical incisions, and for compressing and stabilizing a dissected or traumatized field with ambient air pressure created by an external patient interface component and a vacuum source.

2. Description of the Related Art

Tissue separations can result from surgical procedures and other causes, such as traumatic and chronic wounds. Various medical procedures are employed to close tissue separations. An important consideration relates to securing separate tissue portions together in order to promote closure and healing. Incisions and wounds can be closed with sutures, staples and other medical closure devices. The "first intention" (primary intention healing) in surgery is to "close" the incision. For load-bearing tissues, such as bone, fascia, and muscle, this requires substantial material, be it suture material, staples, or plates and screws. For the wound to be "closed," the epithelial layer must seal. To accomplish this, the "load bearing" areas of the cutaneous and subcutaneous layers (i.e., the deep dermal elastic layer and the superficial fascia or fibrous layers of the adipose tissue, respectively) must also at least be held in approximation long enough for collagen deposition to take place to unite the separated parts.

Other important considerations include controlling bleeding, reducing scarring, eliminating the potential of hematoma, seroma, and "dead-space" formation and managing pain. Dead space problems are more apt to occur in the subcutaneous closure. Relatively shallow incisions can normally be closed with surface-applied closure techniques, such as sutures, staples, glues and adhesive tape strips. However, deeper incisions may well require not only skin surface closure, but also time-consuming placement of multiple layers of sutures in the load-bearing planes.

Infection prevention is another important consideration. Localized treatments include various antibiotics and dressings, which control or prevent bacteria at the incision or wound site. Infections can also be treated and controlled systemically with suitable antibiotics and other pharmacologics.

Other tissue-separation treatment objectives include minimizing the traumatic and scarring effects of surgery and minimizing edema. Accordingly, various closure techniques, postoperative procedures and pharmacologics are used to reduce postoperative swelling, bleeding, seroma, infection and other undesirable, postoperative side effects. Because separated tissue considerations are so prevalent in the medical field, including most surgeries, effective, expedient, infection-free and aesthetic tissue closure is highly desirable from the standpoint of both patients and health-care practitioners. The system, interface and method of the present invention can thus be widely practiced and potentially provide widespread benefits to many patients.

Fluid control considerations are typically involved in treating tissue separations. For example, subcutaneous bleeding occurs at the fascia and muscle layers in surgical incisions. Accordingly, deep drain tubes are commonly installed for the purpose of draining such incisions. Autotransfusion has experienced increasing popularity in recent years as equipment and techniques for reinfusing patients' whole blood have advanced considerably. Such procedures have the advantage of reducing dependence on blood donations and their inherent risks. Serous fluids are also typically exuded from incision and wound sites and require drainage and disposal. Fresh incisions and wounds typically exude blood and other fluids at the patient's skin surface for several days during initial healing, particularly along the stitch and staple lines along which the separated tissue portions are closed.

Another area of fluid control relates to irrigation. Various irrigants are supplied to separated tissue areas for countering infection, anesthetizing, introducing growth factors and otherwise promoting healing. An effective fluid control system preferably accommodates both draining and irrigating functions sequentially or simultaneously.

Common orthopedic surgical procedures include total joint replacements (TJRs) of the hip, knee, elbow, shoulder, foot and other joints. The resulting tissue separations are often subjected to flexure and movement associated with the articulation of the replacement joints. Although the joints can be immobilized as a treatment option, atrophy and stiffness tend to set in and prolong the rehabilitation period. A better option is to restore joint functions as soon as possible. Thus, an important objective of orthopedic surgery relates to promptly restoring to patients the maximum use of their limbs with maximum ranges of movement.

Similar considerations arise in connection with various other medical procedures. For example, arthrotomy, reconstructive and cosmetic procedures, including flaps and scar revisions, also require tissue closures and are often subjected to movement and stretching. Other examples include incisions and wounds in areas of thick or unstable subcutaneous tissue, where splinting of skin and subcutaneous tissue might reduce dehiscence of deep sutures. The demands of mobilizing the extremity and the entire patient conflict with the restrictions of currently available methods of external compression and tissue stabilization. For example, various types of bandage wraps and compressive hosiery are commonly used for these purposes, but none provides the advantages and benefits of the present invention.

The aforementioned procedures, as well as a number of other applications discussed below, can benefit from a tissue-closure treatment system and method with a surface-applied patient interface for fluid control and external compression.

Postoperative fluid drainage can be accomplished with various combinations of tubes, sponges, and porous materials adapted for gathering and draining bodily fluids. The prior art includes technologies and methodologies for assisting drainage. For example, the Zamierowski U.S. Pat. Nos. 4,969,880; 5,100,396; 5,261,893; 5,527,293; and 6,071,267 disclose the use of pressure gradients, i.e., vacuum and positive pressure, to assist with fluid drainage from wounds, including surgical incision sites. Such pressure gradients can be established by applying porous sponge material either internally or externally to a wound, covering same with a permeable, semi-permeable, or impervious membrane, and connecting a suction vacuum source thereto. Fluid drawn from the patient is collected for disposal. Such fluid control methodologies have been shown to achieve significant improvements in patient healing. Another aspect of fluid management, postoperative and otherwise, relates to the application of fluids to wound sites for purposes of irrigation, infection control, pain control, growth factor application, etc. Wound drainage devices are also used to achieve fixation and immobility of the tissues, thus aiding healing and closure. This can be accomplished by both internal closed wound drainage and external, open-wound vacuum devices applied to the wound surface. Fixation of tissues in apposition can also be achieved by bolus tie-over dressings (Stent dressings), taping, strapping and (contact) casting.

Surgical wounds and incisions can benefit from tissue stabilization and fixation, which can facilitate cell migration and cell and collagen bonding. Such benefits from tissue stabilization and fixation can occur in connection with many procedures, including fixation of bone fractures and suturing for purposes of side-to-side skin layer fixation.

Moisture management is another critical aspect of surgical wound care involving blood and exudate in deep tissues and transudate at or near the skin surface. For example, a moist phase should first be provided at the epithelial layer for facilitating cell migration. A tissue-drying phase should next occur in order to facilitate developing the functional keratin layer. Moisture management can also effectively control bacteria, which can be extracted along with the discharged fluids. Residual bacteria can be significantly reduced by wound drying procedures. In some cases such two-stage moist-dry sequential treatments can provide satisfactory bacterial control and eliminate or reduce dependence on antibiotic and antiseptic agents.

Concurrently with such phases, an effective treatment protocol would maintain stabilization and fixation while preventing disruptive forces within the wound. The treatment protocol should also handle varying amounts of wound exudate, including the maximum quantities that typically exude during the first 48 hours after surgery. Closed drainage procedures commonly involve tubular drains placed within surgical incisions. Open drainage procedures can employ gauze dressings and other absorptive products for absorbing fluids. However, many previous fluid-handling procedures and products tended to require additional clean-up steps, expose patients and healthcare professionals to fluid contaminants and require regular dressing changes. Moreover, insufficient drainage could result in residual blood, exudate and transudate becoming isolated in the tissue planes in proximity to surgical incisions.

Still further, certain hemorrhages and other subdermal conditions can be treated with hemostats applying compression at the skin surface. Free fluid edema resorption can be expedited thereby.

Yet another area of wound-dressing and wound-healing technology is what is referred to as "moist wound healing." Three major components that constitute the external and physical environment of the healing wound should, in an ideal wound-healing environment, be controlled. First, wound healing is inversely related to bacterial growth. Second, it has been shown that, holding other variables constant, there is a relationship between the moisture level at the wound-site and the rate of epithelial advancement. The final important characteristic is the surface contact property of the wound dressing. The surface contact property can help to control the other two major factors, but must be made of a suitable material that promotes endurance of the dressing as well as comfort to the patient.

As one example, a piece of thin foam is one format used as a dressing in moist-wound healing applications. The external face of the thin foam may have larger pore sizes for allowing enough moisture retention initially, but then allowing drying to occur with the dressing still in place. Because this foam does not adhere to the wound, it could be moved or removed without disrupting the epithelium. However, this practice has heretofore been limited to use with relatively small incisional wounds, as the thin foam is incapable of managing the amount of exudates from larger, fresh wounds, or being securely held against a raw wound over a larger surface area. Moreover, if exudates accumulate under the foam piece, the foam will lose surface contact which allows bacteria to build up, among other undesirable consequences.

In general, epithelium advances or migrates best if moisture is initially maximized to mature the epithelium (e.g., stratifies, thickens and forms keratin), after which moisture should be minimized. Although the idea of moist wound healing is now over 50 years old, the present invention applies moisture control concepts in systems and methods for closing various types of incisions.

Heretofore there has not been available an externally-applied patient interface including an air press and an incision-closing method with the advantages and features of the present invention.

SUMMARY OF THE INVENTION

In the practice of the present invention, a system and method are provided for enhancing closure of separated tissue portions using a surface-applied patient interface. Subsurface drainage, irrigation and autotransfusion components can optionally be used in conjunction with the surface-applied, external interface. The external interface can be advantageously placed over a stitch or staple line and includes a primary transfer component comprising a strip of porous material, such as rayon, applied directly to the patient for wicking or transferring fluid to a secondary transfer component comprising a sponge or foam material. An underdrape is placed between the transfer elements for passing fluid therebetween through an underdrape opening, such as a slot. An overdrape is placed over the secondary transfer component and the surrounding skin surface. The patient interface is connected to a negative pressure source, such as a vacuum assisted closure device, wall suction or a mechanical suction pump. A manual control embodiment utilizes a finite capacity fluid reservoir with a shut-off valve for discontinuing drainage when a predetermined amount of fluid is collected. An automatic control embodiment utilizes a microprocessor, which is adapted for programming to respond to various inputs in controlling the operation of the negative pressure source. A closed wound or incision treatment method of the present invention involves three phases of fluid control activity, which correspond to different stages of the healing process. In a first phase active drainage is handled. In a second phase components can be independently or sequentially disengaged. In a third phase the secondary transfer component can optionally be left in place for protection and to aid in evacuating any residual fluid from the suture/staple line through the primary transfer component.

In other embodiments of the invention, components of the dressing system can be premanufactured for efficient application. A foam piece can be provided with a full or partial rayon cover and a close-fitting overdrape. An access panel with a reclosable seal strip can be installed on the overdrape for access to the foam pieces and the wound area. A premanufactured external dressing can be provided with a sheath receiving a foam piece, which is accessible through a reclosable seal strip for replacement or reorientation. Treatment area access is also provided through the seal strip. The system can also be employed as a hemostat.

In still other embodiments of the invention, alternative aspects of the unique dressing can be adapted for closing incisions, facilitating and expediting (re)epithelialization and promoting migration and maturation, while minimizing disruption of the fragile cell layers by undue adherence or by motion/friction/abrasion. The invention also facilitates maintaining relatively close tissue surface or edge contacts without intervening dead space, consequential fluid accumulation, lytic bleeding, micro abscess formation or inability to dry and mature epithelium. The invention also facilitates the linking and joining of cell types and tissue planes of all layers of an incisional wound by the "press" effect of creating differential pressure between the negative pressure of open planes (or "dead space" in surgical terms) communicating with the negative pressure and the positive pressure or "press" effect transmitted by the ambient air pressure differential through the tissues. Incision closure is expedited by drawing away vapor and liquid from the wound and introducing drying fresh air with or without liquid rinses or medication administration to the skin surface whereby healing is expedited. In this embodiment, air and moisture levels at the wound-site are balanced by using vacuum pumps to remove contaminated air or moisture, and input pumps or valves are used to add additional clean air, moisture, or other elements which enhance healing. The vacuum pump will also provide the necessary negative pressure to press the dressing against the wound and enhance healing.

By utilizing a fabric or surface lining that has a minimum of alternating spaces of tension and compression and instead has a maximum compressive or contact (i.e. tightly woven fabrics, gels, hydrocollids, rubber or even flexible solids) relationship with the skin, the skin then adopts the elastic characteristics of the external portion of the device and becomes a more rigid sounding board for internal pulsations which in turn influences internal fluid wave dynamics. If we then utilize this zone by placing a bio-reactor in a subsurface or subcutaneous (perhaps even sub fascial) position, we will enhance the cell progression we desire in our bio-reactor.

BRIEF DESCRIPTION OF THE DRAWINGS

The drawings constitute a part of this specification and include exemplary embodiments of the present invention and illustrate various objects and features thereof.

FIG. 10 is a cross-sectional view thereof, taken generally along line 10-10 in FIG. 9 and particularly showing FTC.3.

FIG. 11c is a perspective view of a patient interface adapted for prepackaging, application to a patient and connection to a negative pressure source.

FIGS. 12e,f show a modified FTC.2a with removable wedges to facilitate articulation, such as flexure of a patient joint.

FIGS. 12g,h show alternative embodiment external patient interface assemblies.

FIG. 19 is a cross-sectional view of the tissue closure treatment system, taken generally along line 19-19 in FIG. 18.

FIG. 20 is an enlarged, cross-sectional view of the tissue closure system, particularly showing a reclosable seal strip thereof.

FIG. 43 is a cross-sectional view thereof, showing the dressing compressed under pressure.

FIG. 44 is a top plan view thereof.

FIG. 45 is a cross-sectional view thereof, showing the dressing configuration prior to application to a patient and taken generally along line 45-45 in FIG. 44.

FIG. 46 is a top plan view of an application involving multiple dressings covering an elongated tissue separation, such as a surgical incision.

DETAILED DESCRIPTION OF THE PREFERRED EMBODIMENTS

I. Introduction and Environment

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

II. Tissue Closure System 2

Figure 1:
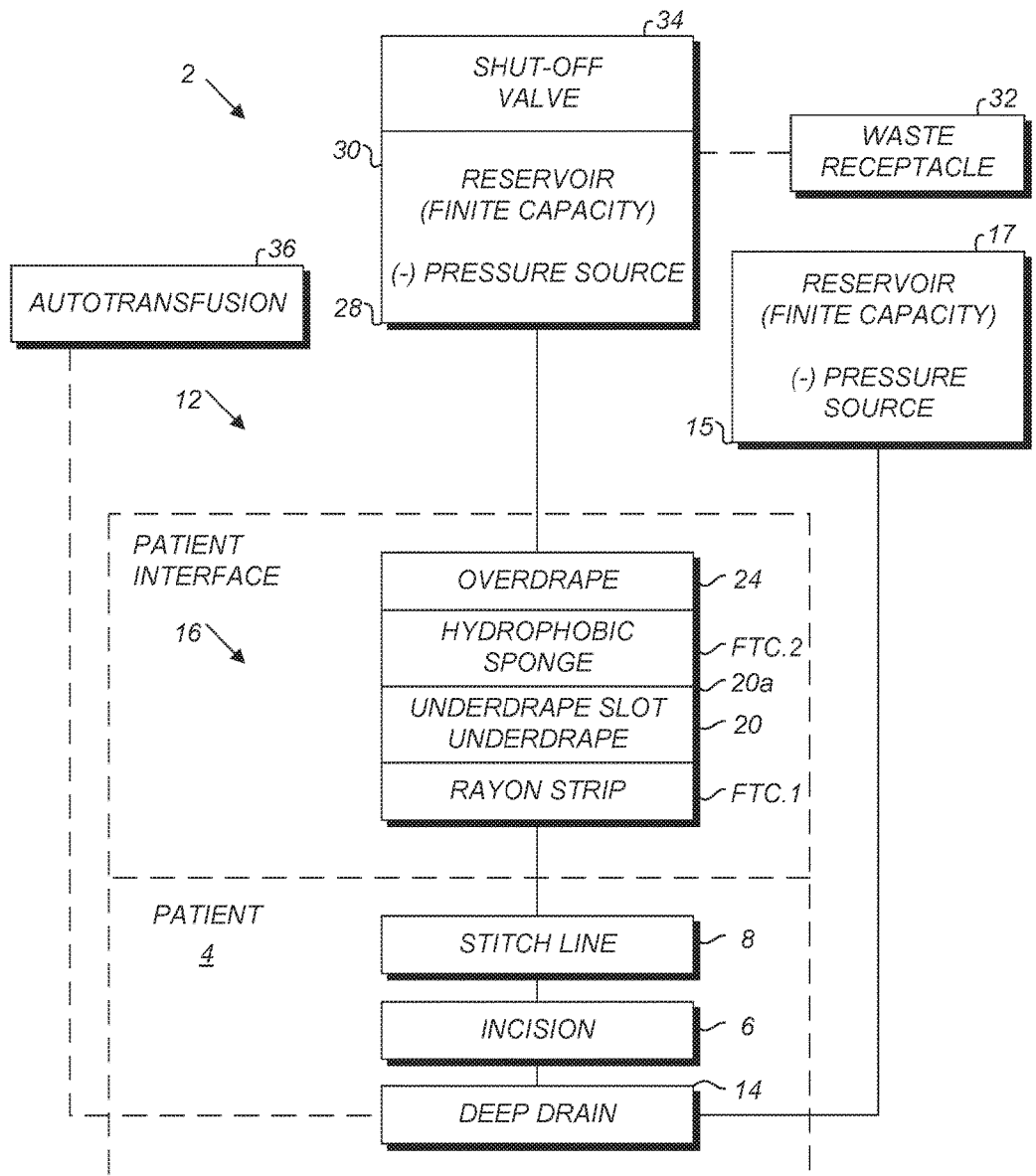
FIG. 1 is a schematic, block diagram of a tissue closure treatment and system embodying the present invention.

Referring to the drawings in more detail, the reference numeral 2 generally designates a tissue closure treatment system embodying the present invention. As shown in FIG. 1, the system 2 is adapted for use on a patient 4 with an incision or wound 6, which can be closed by a stitch line 8 consisting of sutures 10, staples or other suitable medical fasteners.

A patient interface 12 consists of an optional deep drain 14 connected to a deep drain negative pressure source 15 associated with a deep drainage reservoir 17 and an external patient interface 16 including a primary fluid transfer component FTC.1 comprising a strip of rayon or other suitable porous material, an underdrape 20 generally covering FTC.1 and including a slot 20a, a secondary fluid transfer component FTC.2 comprising a hydrophobic sponge and an overdrape 24.

A fluid handling subsystem 26 includes the deep drain negative pressure source 15 and a surface drain negative pressure source 28, which can be combined for applications where a common negative pressure source and a collection receptacle are preferred. The negative pressure sources 15, 28 can operate either manually or under power. Examples of both types are well-known in the medical art. For example, a manually operable portable vacuum source (MOPVS) is shown in U.S. Pat. No. 3,115,138, which is incorporated herein by reference. The MOPVS is available from Zimmer, Inc. of Dover, Ohio under the trademark HEMOVAC®. Bulb-type actuators, such as that shown in U.S. Pat. No. 4,828,546 (incorporated herein by reference) and available from Surgidyne, Inc. of Eden Prairie, Minn., can be used on smaller wounds, for shorter durations or in multiples. Moreover, power-actuated vacuum can be provided by vacuum assisted closure equipment available under the trademark THE VAC® from Kinetic Concepts, Inc. of San Antonio, Tex. Still further, many health-care facilities, particularly hospitals and clinics, are equipped with suction systems with sources of suction available at wall-mounted outlets.

A finite capacity reservoir 30 is fluidically connected to the negative pressure source 28 and is adapted to discharge to a waste receptacle 32. A shut-off valve 34 is associated with the reservoir 30 and is adapted to automatically discontinue drainage when the reservoir 30 is filled to a predetermined volume.

An optional autotransfusion subsystem 36 can be connected to the deep drain 14 and is adapted for reinfusing the patient 4 with his or her own blood. U.S. Pat. No. 5,785,700 discloses such an autotransfusion system with a portable detachable vacuum source, which is available from Zimmer, Inc. and is incorporated herein by reference.

Figure 2:
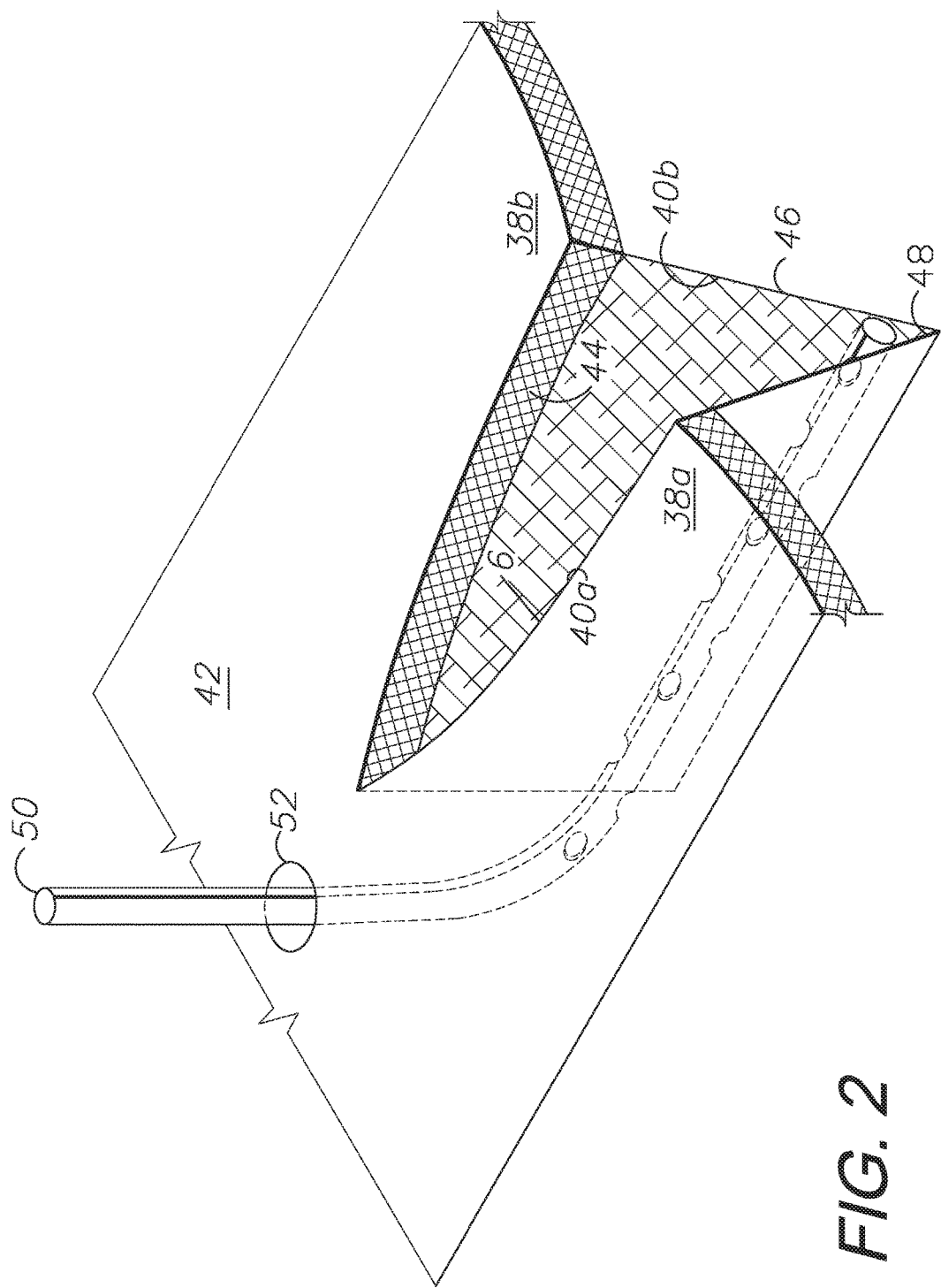
FIG. 2 is a perspective view of an incision tissue separation with a deep drain tube installed.

FIG. 2 shows an incision 6 forming first and second separated tissue portions 38a,b with incision edges 40a,b. The incision 6 extends from and is open at the skin 42, through the deep dermal layer 44 and the subcutaneous layer 46, to approximately the fascia 48. A deep drain tube 50 is placed in a lower part of the incision 6 and penetrates the skin 42 at an opening 52.

Figure 3:
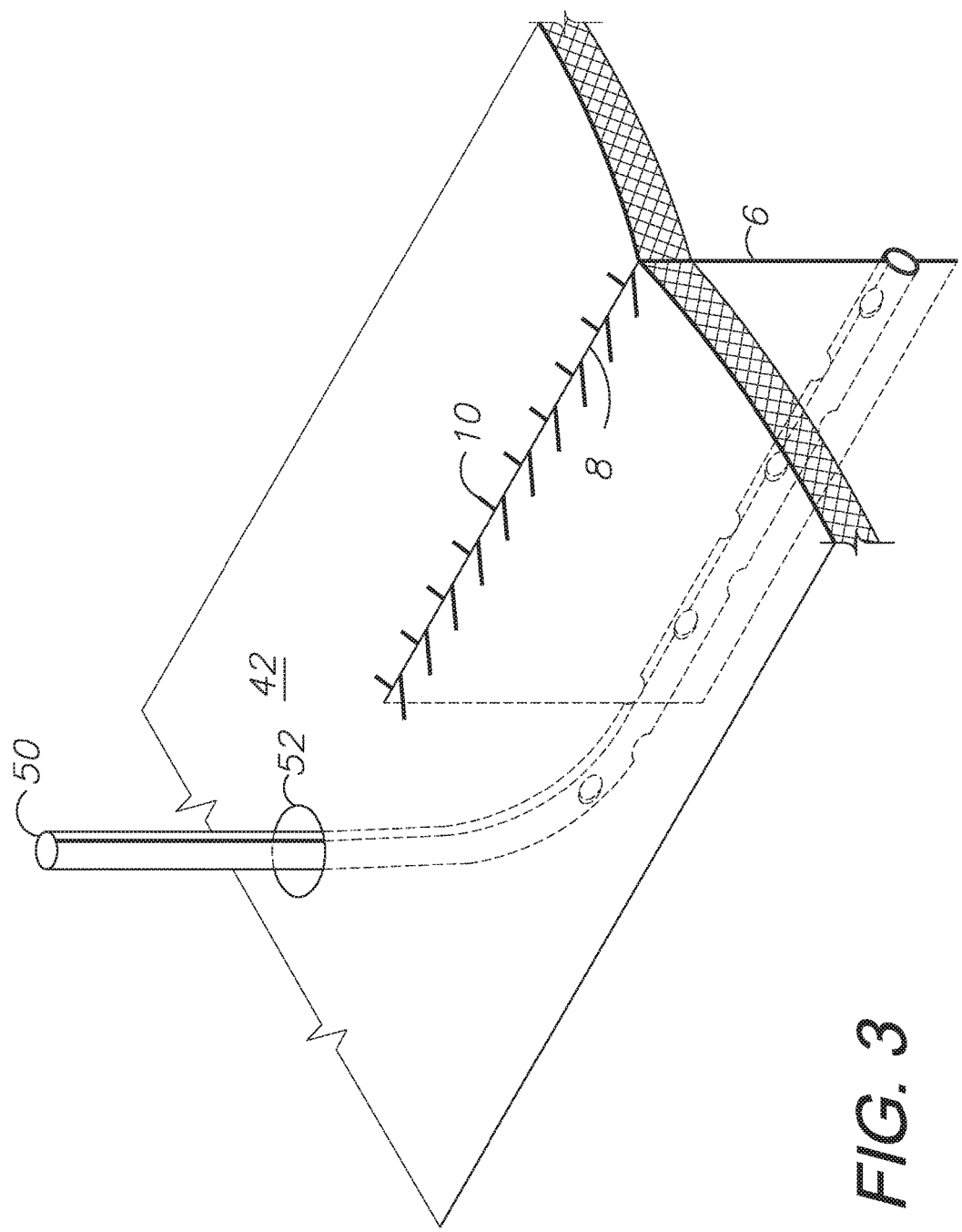
FIG. 3 is a perspective view thereof, showing the separated tissue sutured together at the skin.
Figure 4:
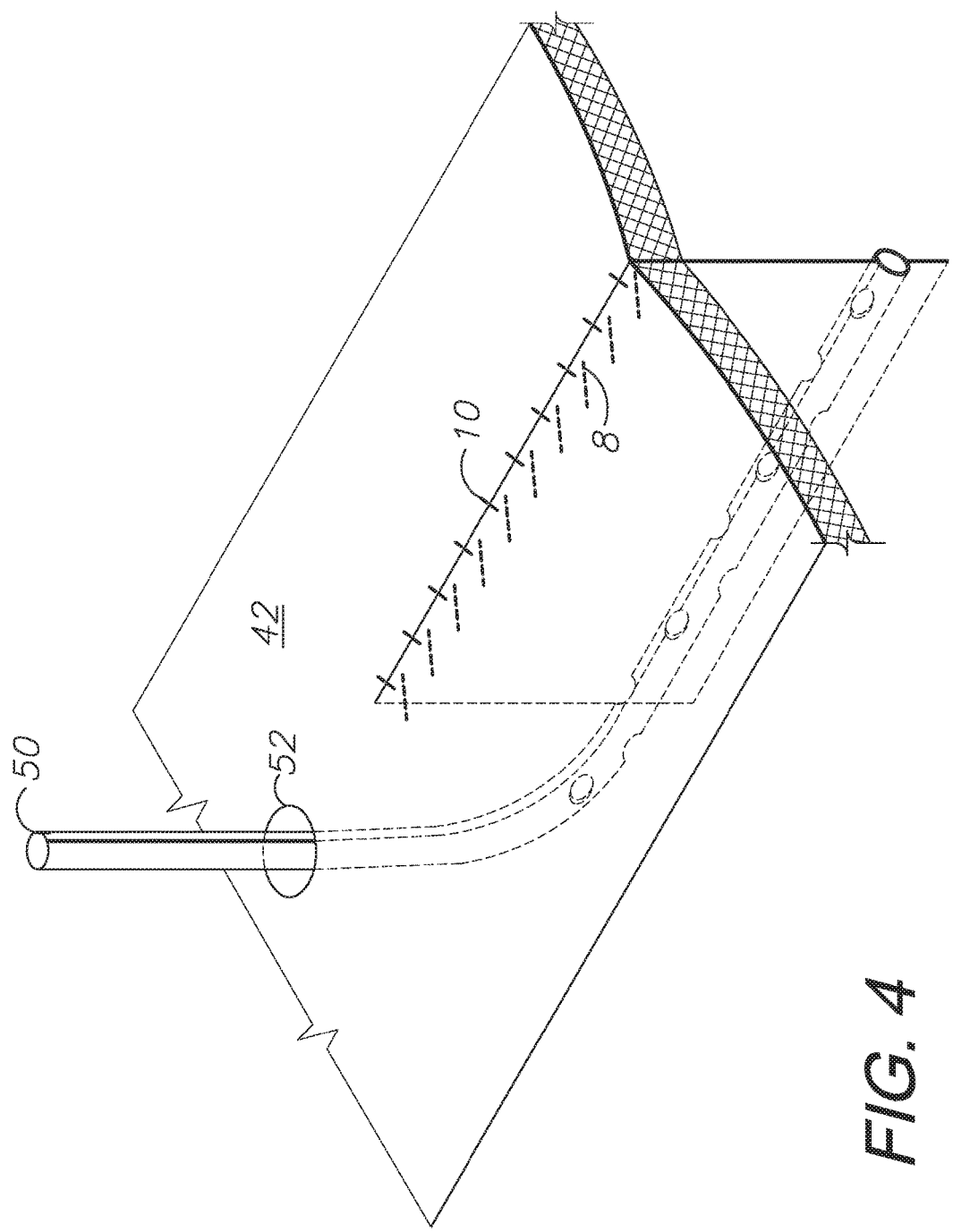
FIG. 4 is a perspective view thereof, showing the separated tissue sutured together at the deep dermal layer below the skin surface.

FIG. 3 shows the incision edges 40a,b secured together by sutures 10 forming a stitch line 8 at the skin surface 42. As an alternative to sutures 10, various other medical fasteners, such as staples, can be used. FIG. 4 shows sutures 10 placed in the deep dermal layer 44 below the skin surface 42.

Figure 5:
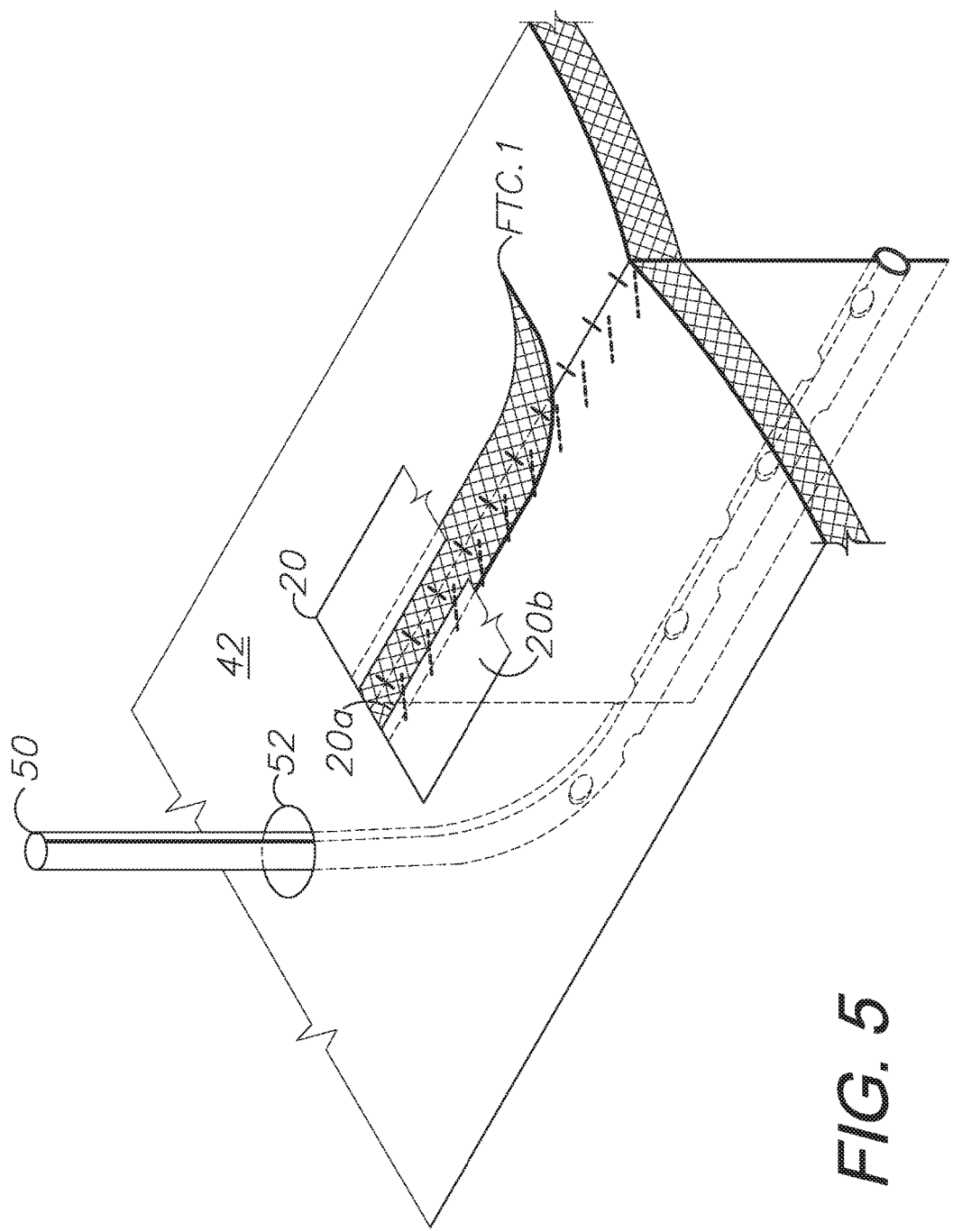
FIG. 5 is a perspective view thereof, showing a rayon strip primary fluid transfer component (FTC.1) and an underdrape being placed on the stitch line.
Figure 6:
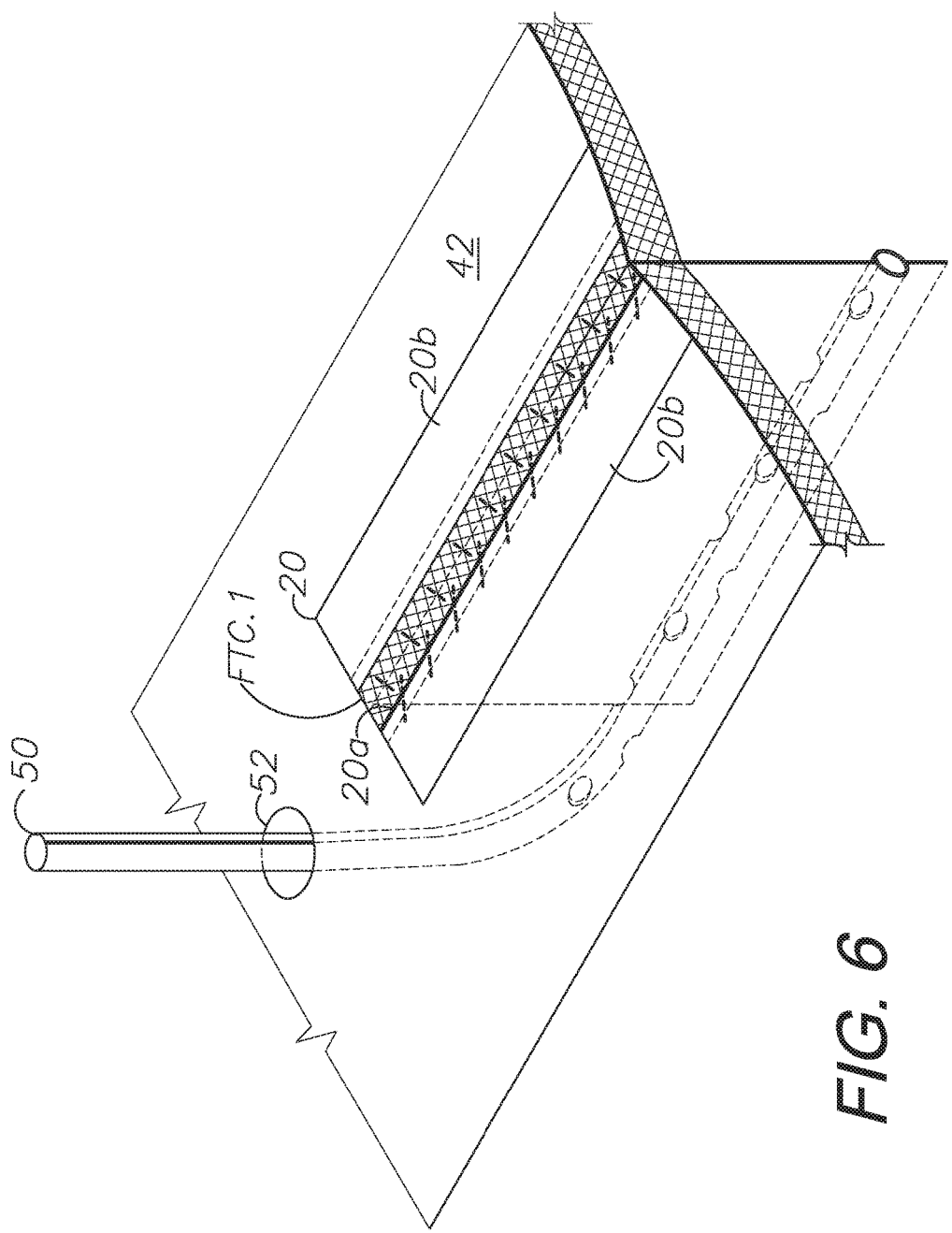
FIG. 6 is a perspective view thereof, showing FTC.1 and the underdrape in place on the stitch line.

FIG. 5 shows application of FTC.1 on top of the stitch line 8. FTC.1 preferably comprises a suitable porous wicking material, such as rayon, which is well-suited for wicking the fluid that exudes along the stitch line 8. Rayon also tends to dry relatively quickly, and thus efficiently transfers fluid therethrough. The underdrape 20 is placed over FTC.1 and the adjacent skin surface 42. Its slot 20a is generally centered along the centerline of FTC.1 and directly above the stitch line 8. FTC.1 and the underdrape 20 can be preassembled in a roll or some other suitable configuration adapted to facilitate placement on the stitch line 8 in any desired length. FIG. 6 shows FTC.1 and the underdrape 20 in place.

Figure 7:
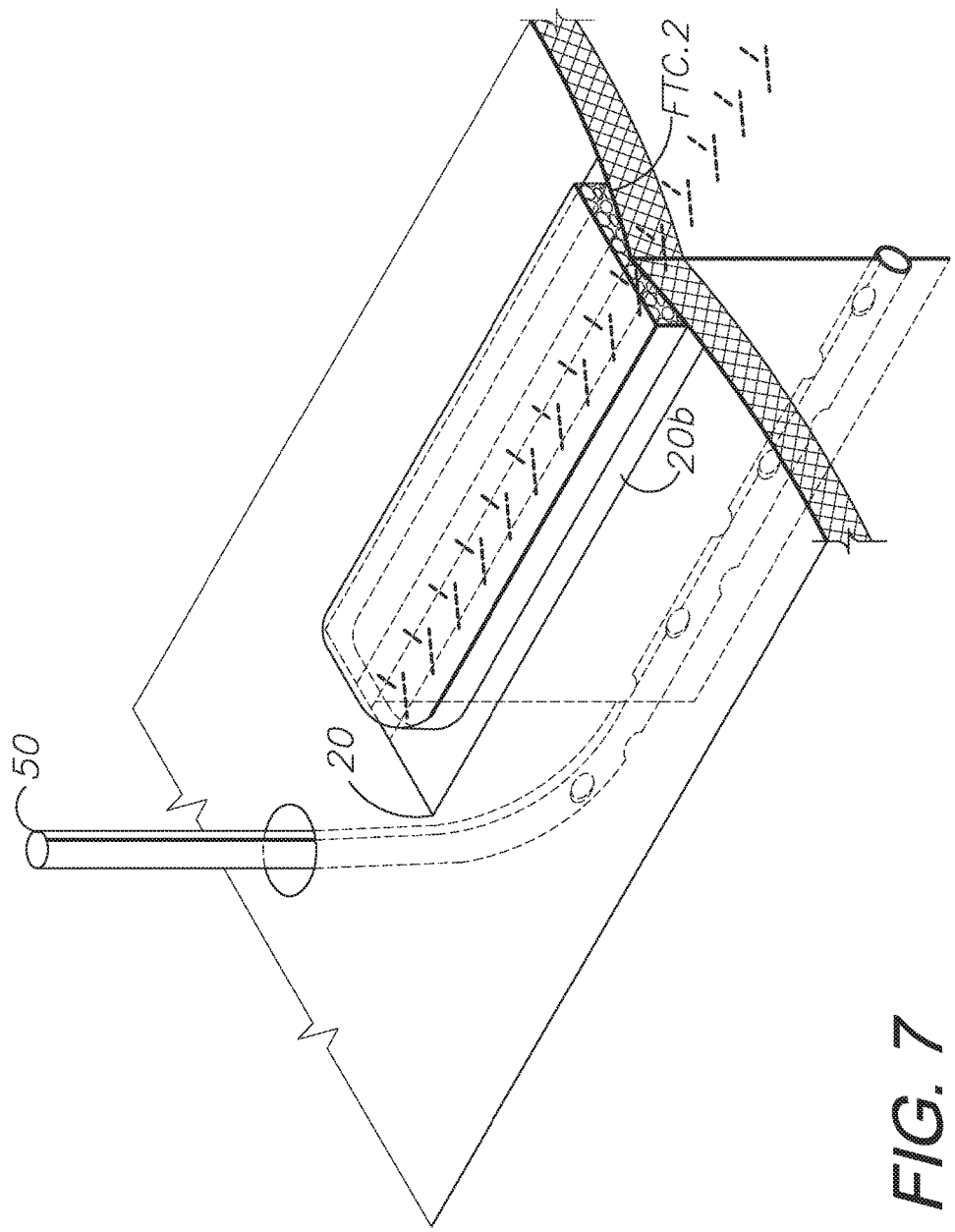
FIG. 7 is a perspective view thereof, showing a secondary fluid transfer component (FTC.2) in place.

The secondary fluid transfer component FTC.2 is shown installed in FIG. 7. It preferably comprises a suitable hydrophobic foam material, such as polyurethane ether (PUE), which comprises a reticulated, lattice-like (foam) material capable of being collapsed by vacuum force (negative pressure) in order to exert positive "shrink-wrap" type compression on skin surface and still maintain channels that allow passage of fluid. As shown, its footprint is slightly smaller than that of the underdrape 20, thus providing an underdrape margin 20b. The wicking layer of FTC.1 can, as an alternative, be sized equal to or almost equal to the footprint of FTC.2. This configuration lends itself to prefabrication as an individual, pre-assembled pad that can be employed by simply removing a releasing layer backing from an adhesive lined underdrape. This configuration also lends itself to easy total removal and replacement of the central part of the assembly without removing drape already adhered to skin if removal and replacement is the desired clinical option rather then staged removal or prolonged single application.

Figure 8:
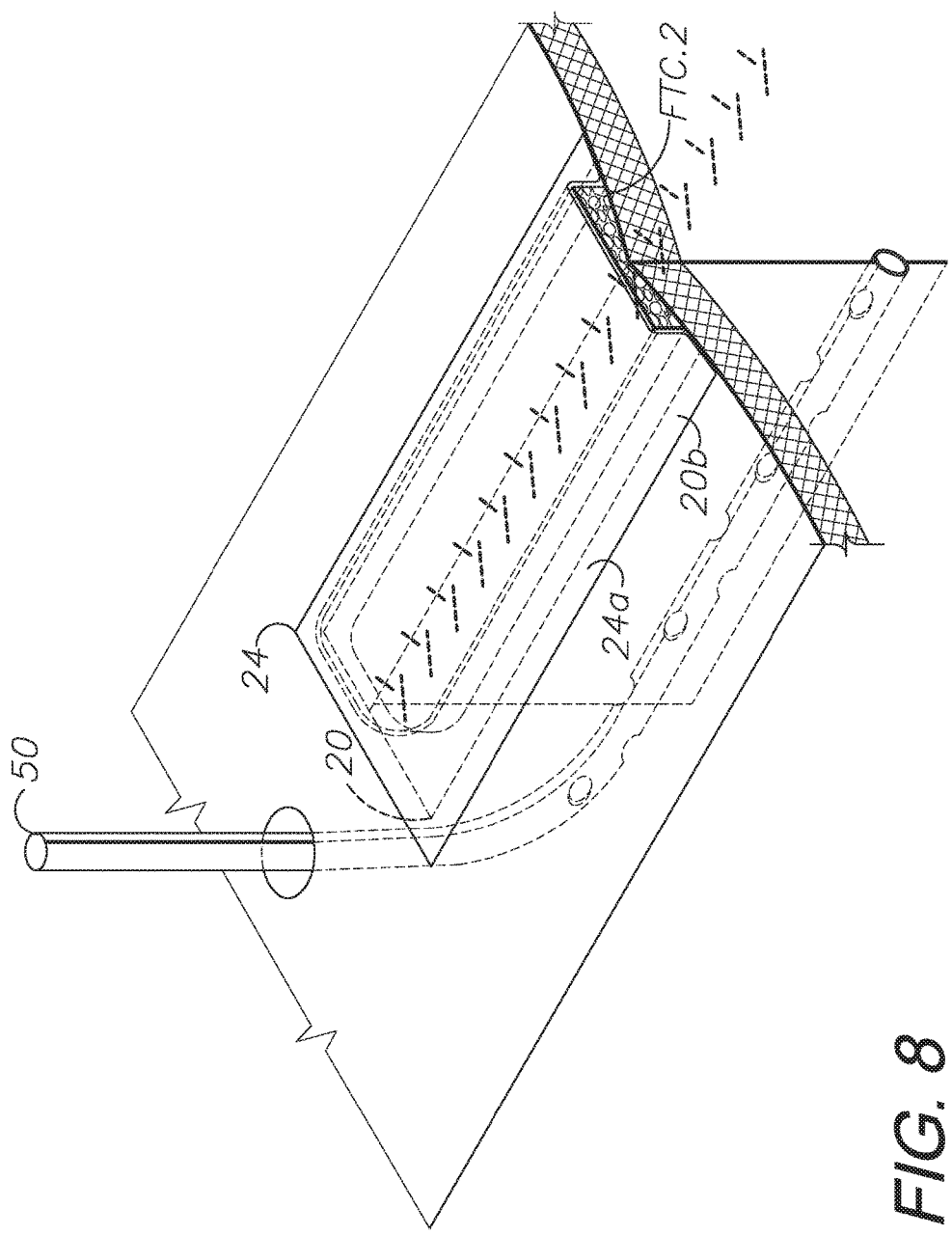
FIG. 8 is a perspective view thereof, showing an overdrape in place.
Figure 9:
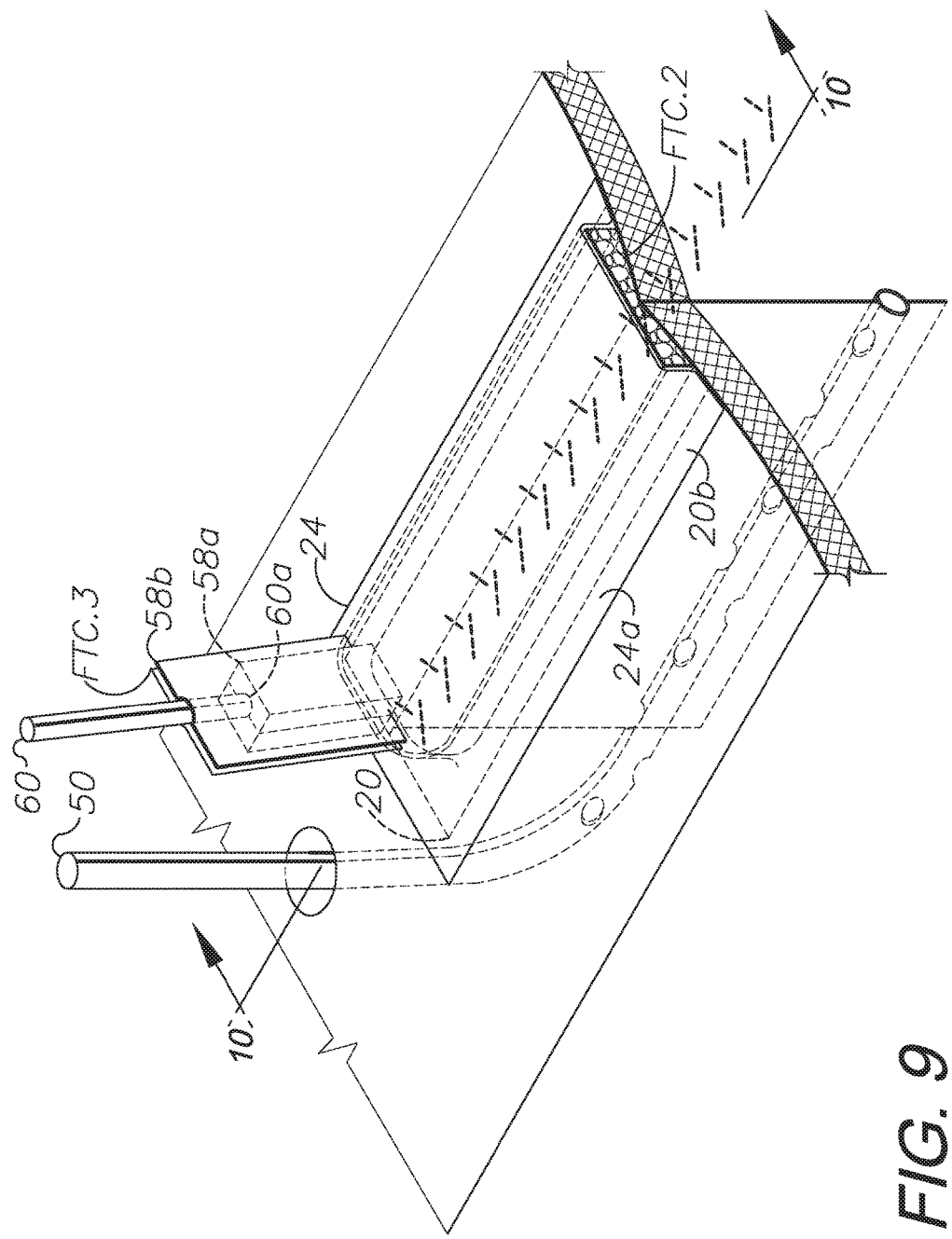
FIG. 9 is a perspective view thereof, showing a connecting fluid transfer component (FTC.3) in place for connecting the system to a negative pressure source.

FIG. 8 shows the overdrape 24 applied over FTC.2 and the underdrape 20, with a margin 24a extending beyond the underdrape margin 22b and contacting the patient's skin surface (dermis) 42. FIGS. 9 and 10 show a patch connector 58 mounted on FTC.2 and comprising a hydrophobic foam (PUE) material core 58a sandwiched between drape layers 58b. A vacuum drain tube 60 includes an inlet end 60a embedded in the foam core 58a and extends between the drape layers 58b to an outlet end 60b connected to the surface drainage negative pressure source 28.

Figure 11A:
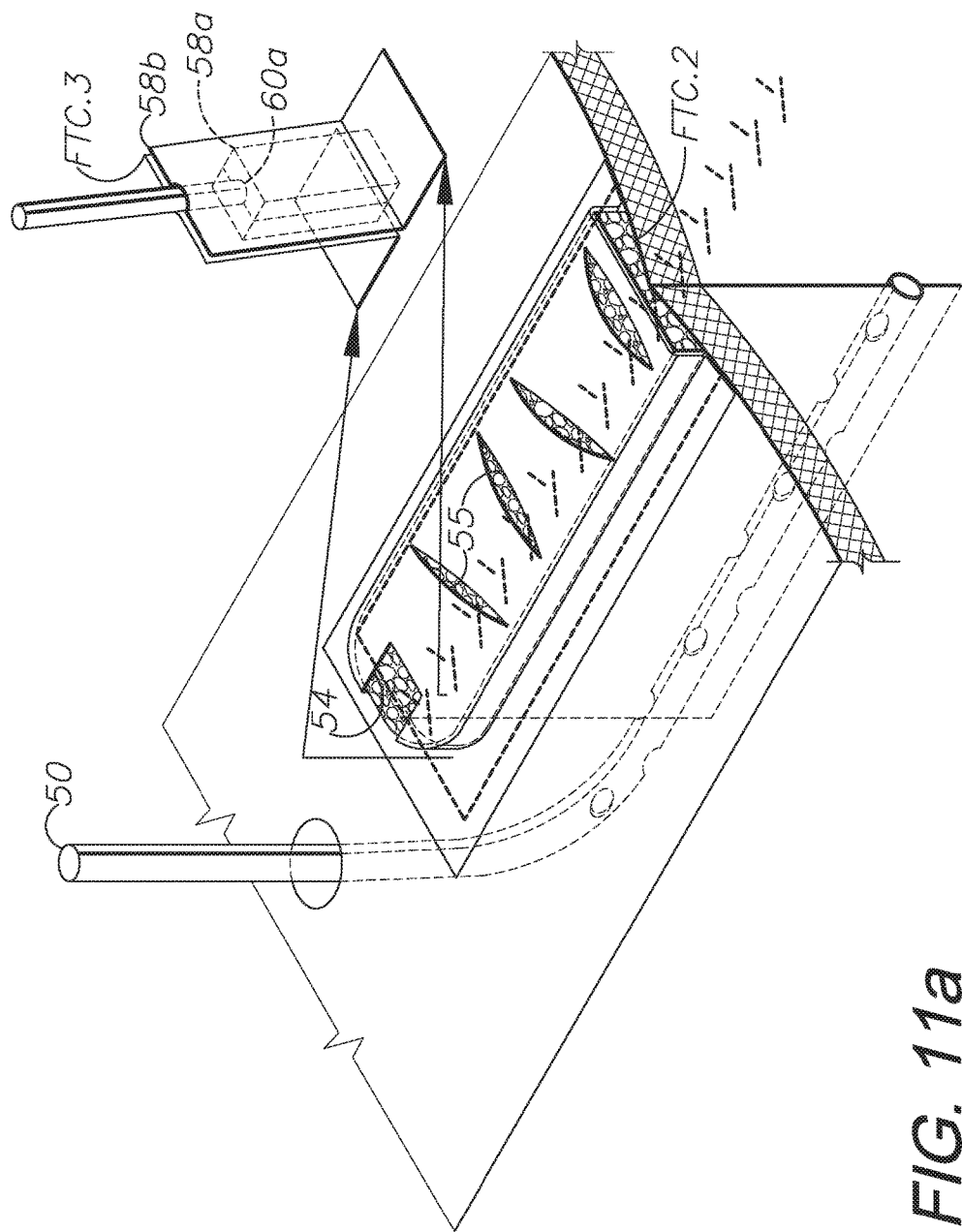
FIG. 11a is a perspective view thereof, showing FTC.3 removed and the overdrape scored for ventilation.

FIG. 11a shows FTC.3 removed, e.g. by cutting away portions of the overdrape 24 to provide an overdrape opening 54. In addition, the overdrape 24 can be slit at 55 to further ventilate FTC.2. Draining FTC.2 under negative pressure, and further drying it with air circulation (FIG. 11a) can provide significant healing advantages by reducing the growth of various microbes requiring moist environments in FTC.2. Such microbes and various toxins produced thereby can thus be evaporated, neutralized and otherwise prevented from reentering the patient. Microbe control can also be accomplished by introducing antiseptics in and irrigating various components of the patient interface 12, including the drapes 20, 24; FTC.1; FTC.2; and FTC.3.

Figure 11B:
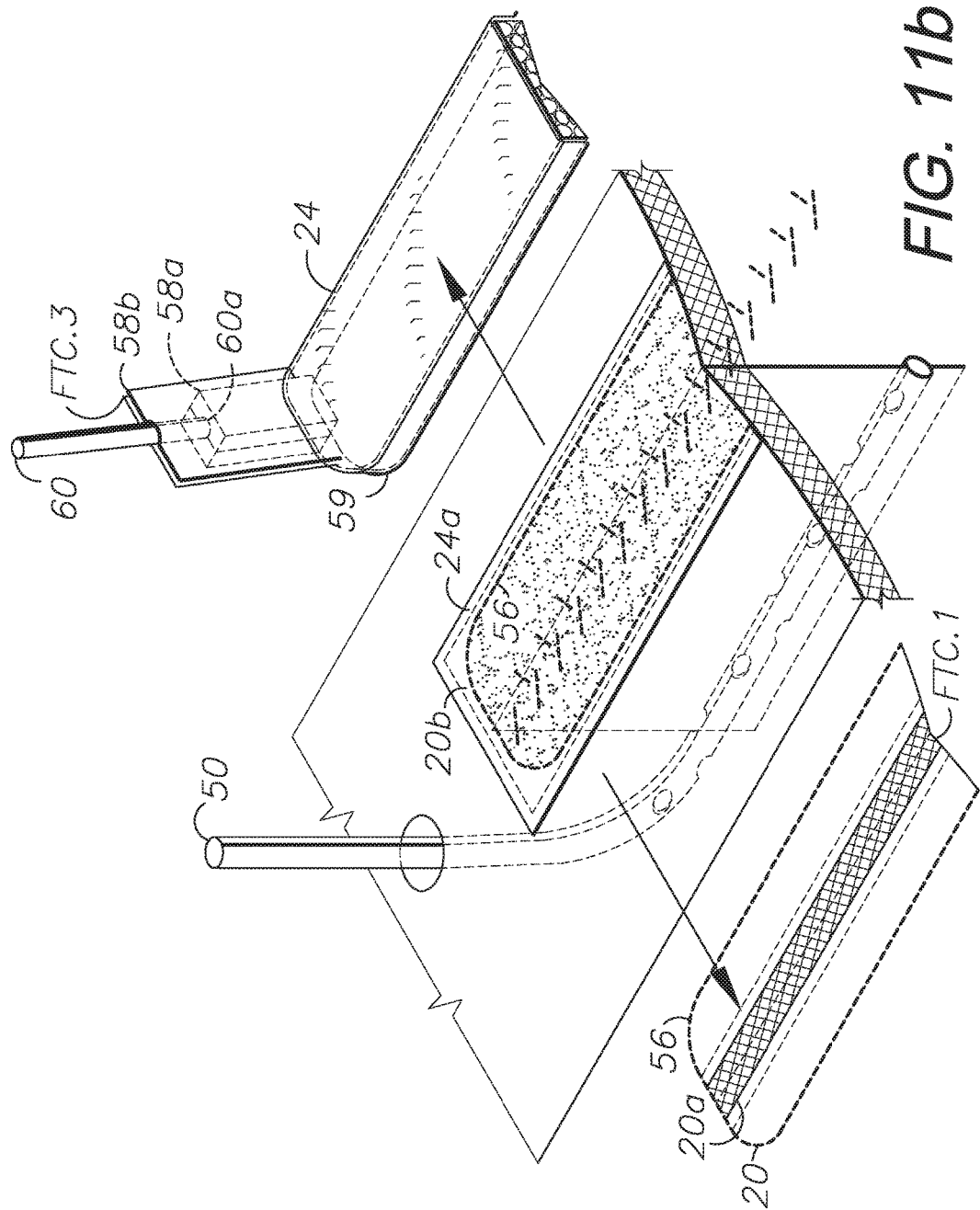
FIG. 11b is a perspective view thereof, showing the patient interface removed along a perforated tear line in the underdrape and a slit line in the overdrape.
Figure 12A:
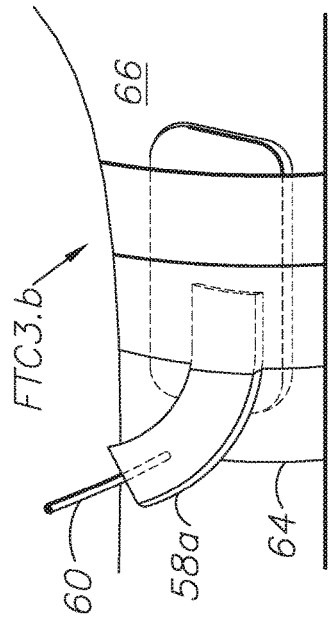
FIGS. 12a-d show alternative embodiment elbow connecting devices FTC.3a-d respectively.
Figure 12B:
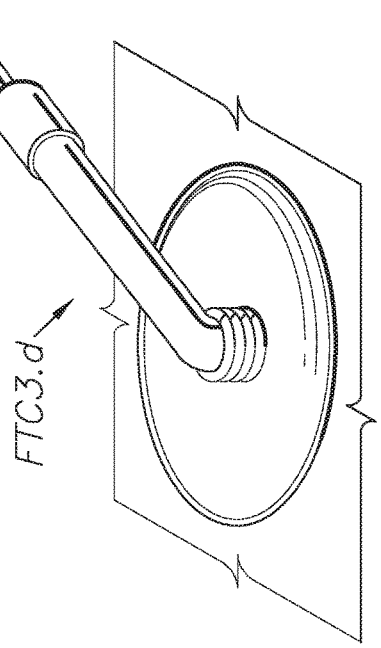
Figure 12C:
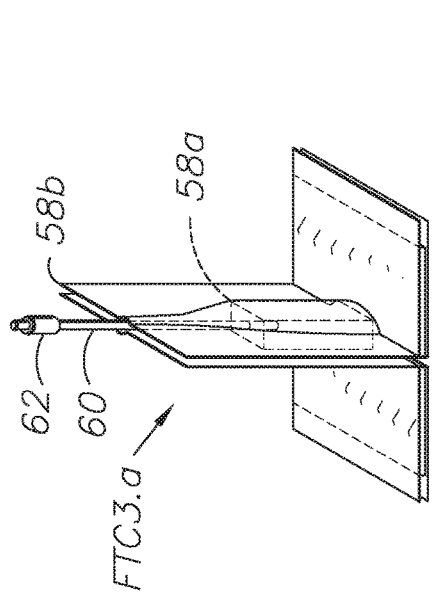
Figure 12D:
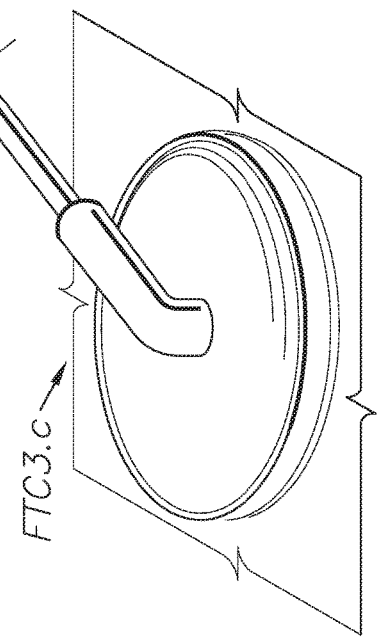

FIG. 11b shows the patient interface 12 removed along underdrape perforated tear lines 56 and slit lines 59 in overdrape 24. It will be appreciated that substantially the entire patient interface 12, except for underdrape and overdrape margins 20b, 24a can thus be removed to provide access to the stitch line 8 and the dermis 42 for visual inspection, evaluation, cleaning, stitch removal, dressing change (e.g., with prepackaged patient interface 12a as shown in FIG. 11c), consideration of further treatment options, etc. For example, the overdrape 24 can be slit to around the perimeter or footprint of FTC.2 to permit removing the same. Preferably FTC.2 is easily releasable from the underdrape 20 and FTC.1 whereby FTC.2 can be grasped and lifted upwardly to facilitate running a scalpel through the overdrape 24 and into a separation between the underside of FTC.2 and the underdrape 20. The FTC.1 can then optionally be removed by tearing the underdrape 20 along its tear lines 56 and removing same as shown in FIG. 11b.

FIG. 11c shows a prepackaged patient interface 12a adapted for initial or "dressing change" application. Optionally, the rayon strip FTC.1 can have the same configuration or "footprint" as the foam sponge FTC.2, thus eliminating the underdrape 20. The prepackaged patient interface 12a can be sterilely packaged to facilitate placement directly on a stitch line 8. Alternatively, the patient interface components can be prepackaged individually or in suitable groups comprising subassemblies of the complete patient interface 12. For example, the underdrape/FTC.1 and the overdrape/FTC.2 subassemblies respectively can be prepackaged individually. Various sizes and component configurations of the patient interface can be prepackaged for application as indicated by particular patient conditions. Preferably, certain sizes and configurations would tend to be relatively "universal" and thus applicable to particular medical procedures, such as TJRs, whereby patient interface inventory can be simplified. Alternatively, the individual components can be assembled in various sizes and configurations for "custom" applications.

FIGS. 12a-d show alternative connecting fluid transfer components FTC.3a-d for connecting FTC.2 to the surface drainage negative pressure source 28. FTC.3a (FIG. 12a) shows a patch connector with a similar construction to FTC.3 and adapted for placement at any location on the overdrape 24. FTC.3a is provided with a Leur lock connector 62. FTC.3b (FIG. 12b) comprises a strip of hydrophobic (PUE) foam material partially covered by an overdrape 64, which can be configured as a wrap around a patient's limb or extremity 66. FTC.3c (FIG. 12c) is an elbow-type connector. FTC.3d (FIG. 12d) is a bellows-type elbow connector, which is adapted to accommodate deflection of the vacuum drain tube 60.

FIGS. 12e,f show an alternative construction of FTC.2a with multiple, removable wedges 57 formed therein and adapted for accommodating articulation, such as joint flexure. The flexibility of FTC.2a can thus be considerably enhanced for purposes of patient comfort, mobility and flexibility. Such wedges can extend transversely and/or longitudinally with respect to FTC.2a. FTC.2a functions in a similar manner with and without the wedges 57 in place or removed.

FIG. 12g shows a modified patient interface 312 with the underdrape 20 placed below FTC.1. This configuration permits removing FTC.1 without disturbing the underdrape 20. FIG. 12h shows a further modified patient interface 412 with FTC.1 having the same configuration or footprint as FTC.2, whereby they can be fabricated and bonded together. In this configuration the underdrape 20 can be omitted.

III. Treatment Method

Figure 13A:
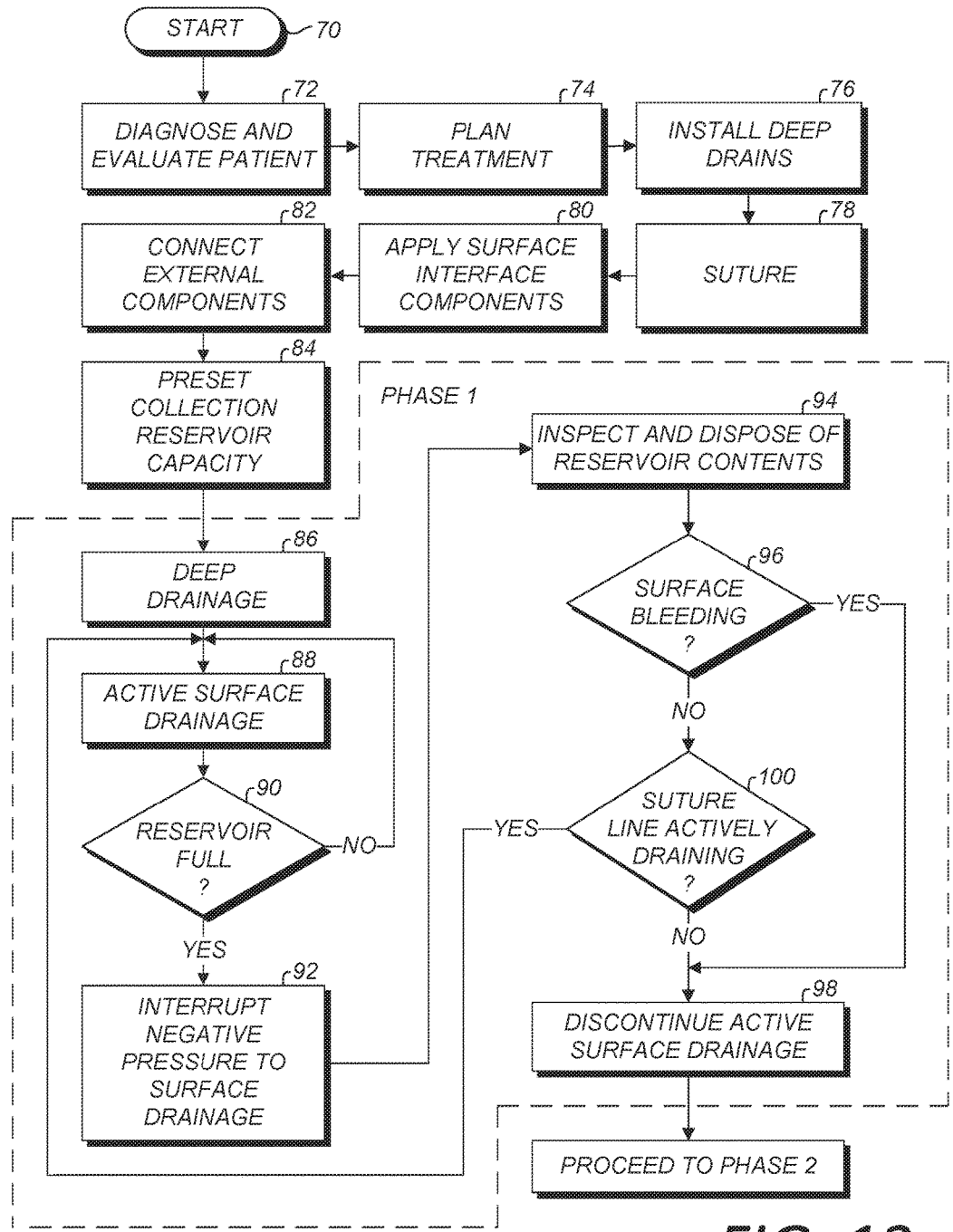
FIGS. 13a-c comprise a flowchart showing a tissue closure treatment method embodying the present invention.
Figure 13B:
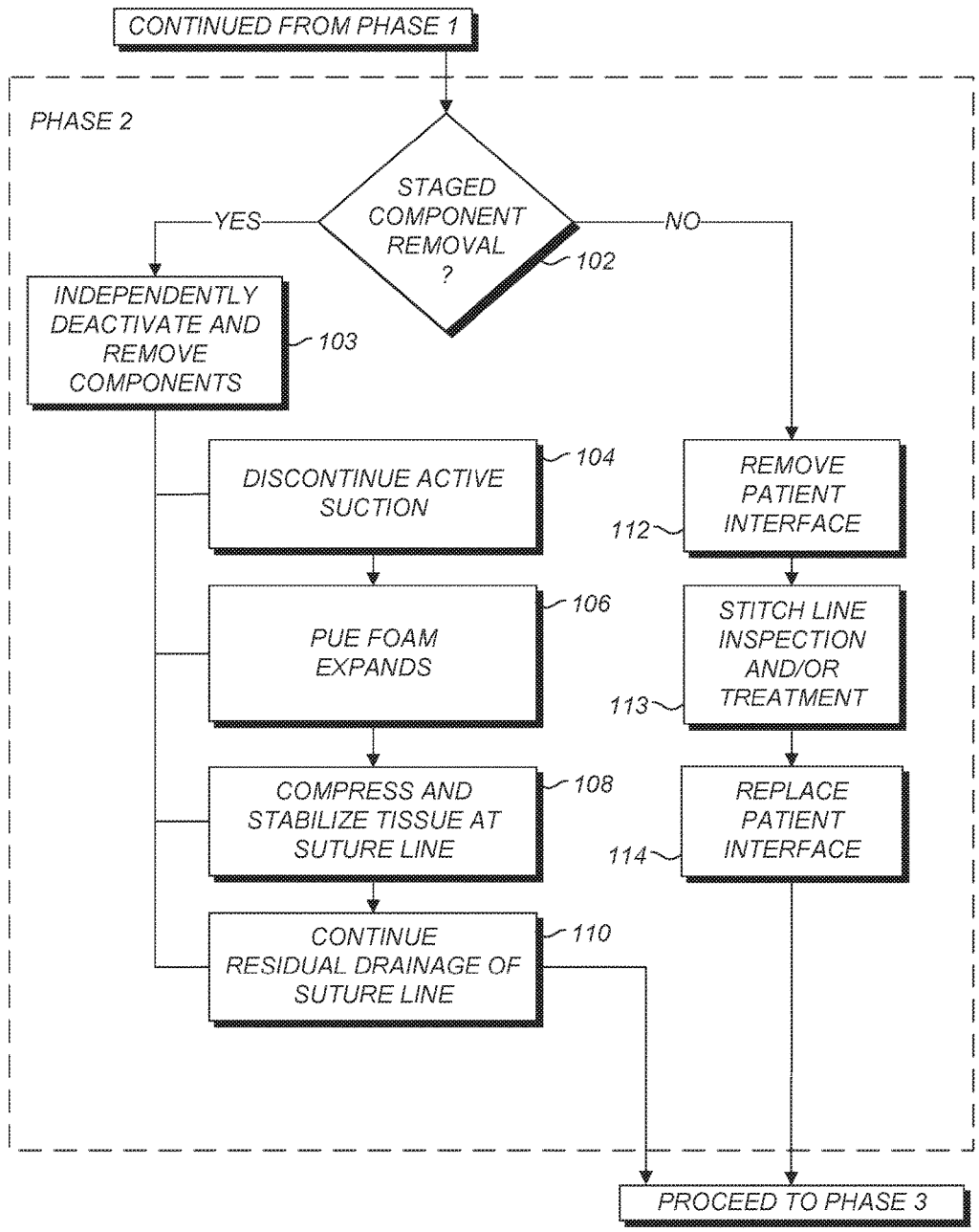
Figure 13C:
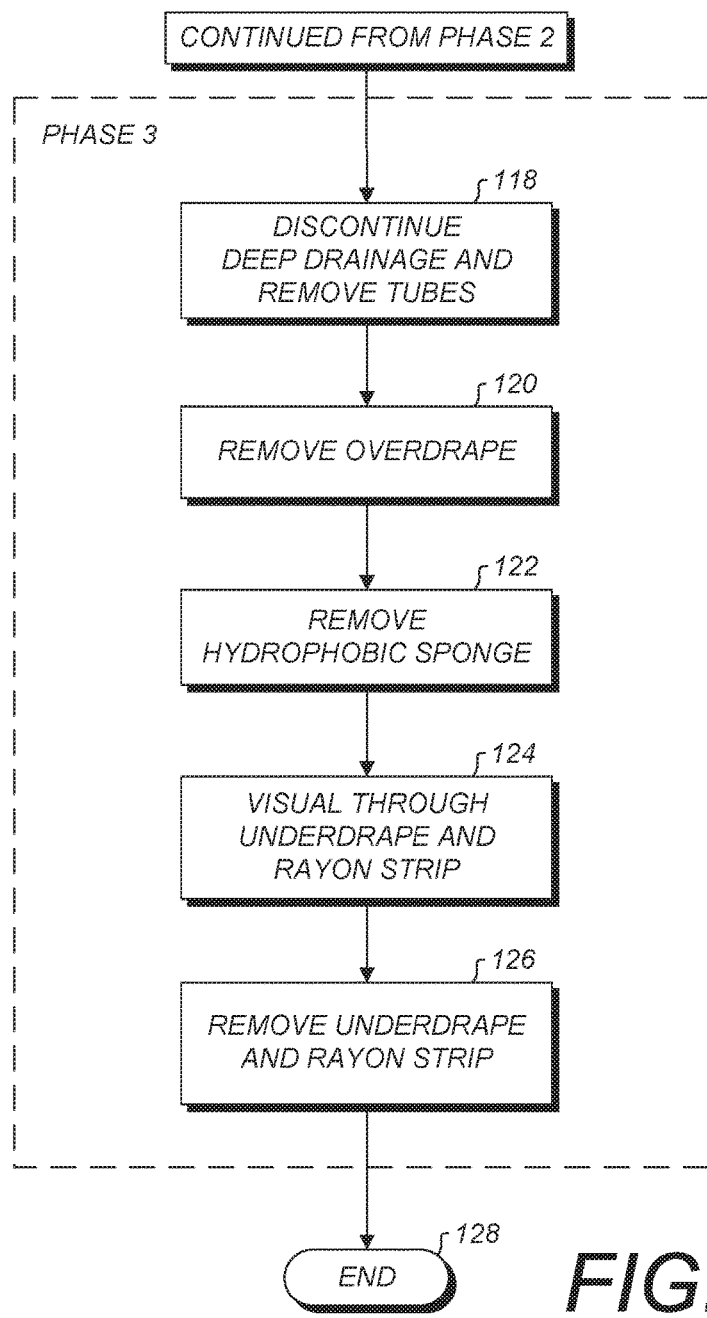

FIGS. 13a-c comprise a flowchart for a method embodying the present invention. From start 70 the method proceeds to patient diagnosis and evaluation at 72 and treatment plan at 74. Deep drains 14 are installed at 76 as necessary, and the incision is sutured at 78. Surface interface components 12 are applied at 80 and connected to the external components (i.e., negative pressure sources 15, 28) at 82. The collection reservoir capacity is preset at 84 based on such factors as nature of wound/incision, blood flow, etc.

Phase 1

Deep drainage occurs at 86 and active surface drainage occurs at 88, both being influenced by the negative pressure sources 15, 28. The negative pressure source 28 causes the PUE foam FTC.2 to partially collapse, which correspondingly draws down the overdrape 24 and exerts a positive, compressive force on the closed wound or incision 6. In the closed environment of the patient interface 12, such force is effectively limited to ambient atmosphere. This limiting control feature protects the patient from excessive force exerted by the patient interface 12. The steady force of up to one atmosphere applied across the closed wound or incision 6 functions similarly to a splint or plaster cast in controlling edema and promoting healing.

A "Reservoir Full" condition is detected at 90 and branches to an interrupt of the surface drainage negative pressure at 92, after which the reservoir contents are inspected and disposed of at 94. If surface bleeding is detected by visual inspection at decision box 96, the method branches to a "Discontinue Active Surface Drainage" step at 98. If the suture line is actively draining at decision box 100, the method loops to the active surface drainage step 88 and continues, otherwise active surface drainage discontinues at 98, i.e. when the wound/incision is neither bleeding nor exuding fluids.

Phase 1 is generally characterized by deep drainage (interactive or passive) and active surface drainage under the influence of manual or powered suction. The normal duration is approximately two to three days, during which time post-operative or post-trauma swelling normally reaches its maximum and begins to recede.

Phase 2

FIG. 13b shows Phase 2 commencing with a "Staged Component Removal?" decision box 102. An affirmative decision leads to independently deactivating and removing components at 103, including discontinuing active suction at 104, which transforms the hydrophobic PUE foam (FTC.2) internal pressure from negative to positive and allows the collapsed FTC.2 to reexpand at 106, potentially increasing surface composite pressure from ambient to positive. Preferably this transition occurs without applying undue pressure to the surface from the decompressed, expanding FTC.2. During Phase 1, negative pressure (i.e., suction/vacuum) tends to compress FTC.2 and correspondingly contracts the overdrape 24, adding to the compression exerted by FTC.2. When the application of negative pressure discontinues, either manually or automatically, FTC.2 re-expands against the constraints of the overdrape 24, and in an equal and opposite reaction presses against the skin 42, particularly along the stitch line 8. FTC.2 can thus automatically transform from ambient to positive pressure simply by discontinuing the application of the vacuum source.

The positive pressure exerted on the skin 42 continues to compress and stabilize tissue along the suture line 8 (step 108) in order to reduce swelling and cooperates with the operation of FTC.1 and FTC.2 to continue drainage by evaporation at the suture line 8 at step 110. A negative determination at decision box 102 leads to interface removal at 112 and, unless treatment is to be terminated, stitch line inspection and treatment at 113 and interface replacement at 114, which can involve all or part of the patient interface 12. The method then proceeds to Phase 3.

Phase 3

FIG. 13c shows Phase 3 of the treatment method wherein deep drainage is discontinued and the tube(s) is removed at 118. The overdrape 24 and FTC.2 are removed at 120, 122 respectively. The underdrape 20 and FTC.1 are preferably configured to permit visual inspection of the suture line 8 therethrough at 124. When the suture line 8 has closed sufficiently, the underdrape 20 and FTC.1 are removed at 126 and the treatment ends at 128. Alternatively and if indicated by the patient's condition, all or part of the interface 12 can be replaced in Phase 3 and treatment continued.

IV. Alternative Embodiment Tissue Closure System 202

Figure 14:
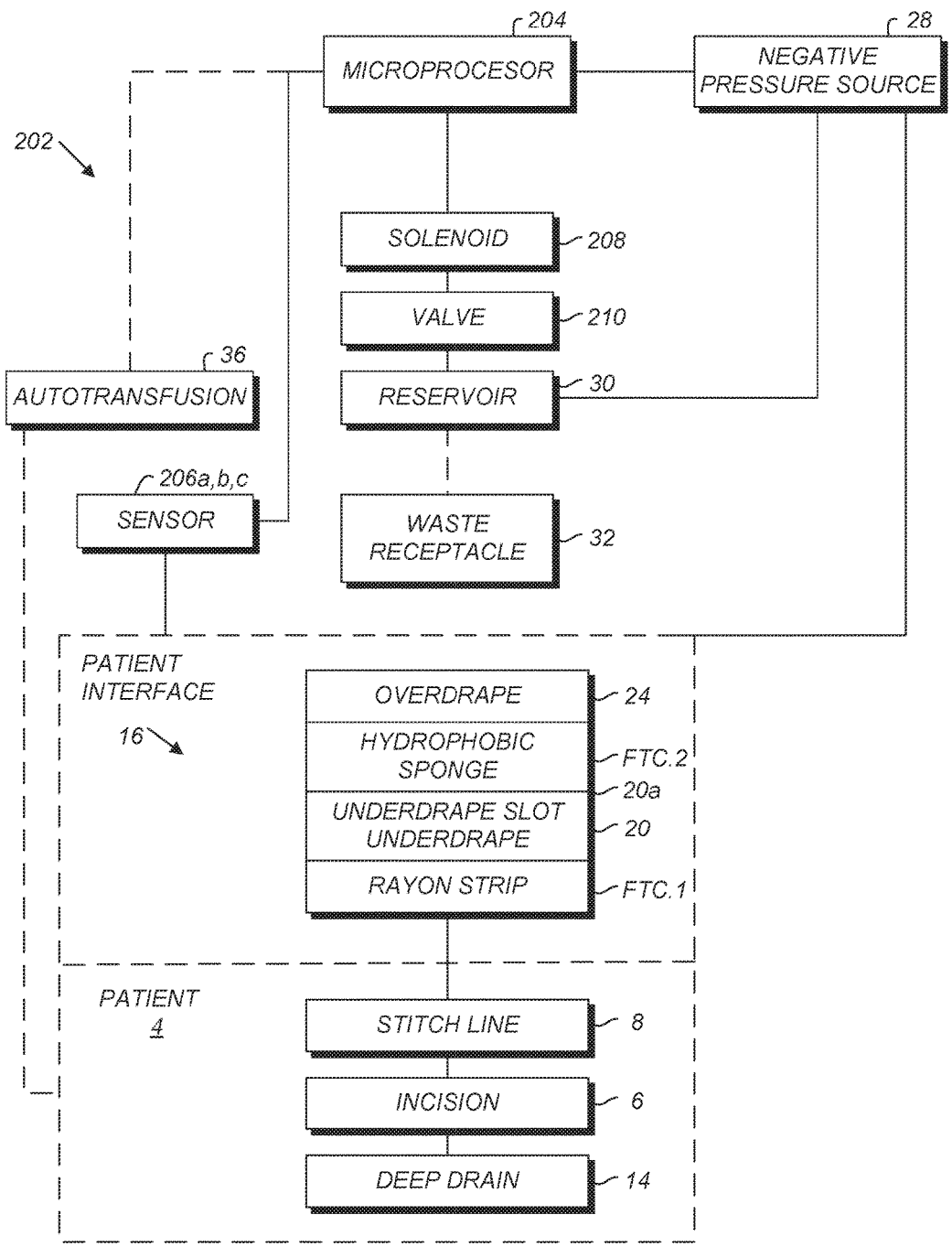
FIG. 14 is a schematic, block diagram of an automated tissue closure treatment system comprising an alternative embodiment of the present invention.

FIG. 14 schematically shows a tissue closure system 202 comprising an alternative embodiment of the present intention, which includes a microprocessor or controller 204, which can be connected to one or more sensors 206 coupled to the patient interface 12 for sensing various conditions associated with the patient 4. The microprocessor 204 can be programmed to operate a solenoid 208 coupled to a valve 210 associated with the reservoir 30 and controlling fluid flow induced by a negative pressure source 228 through its connection to the patient interface 12.

Figure 15:
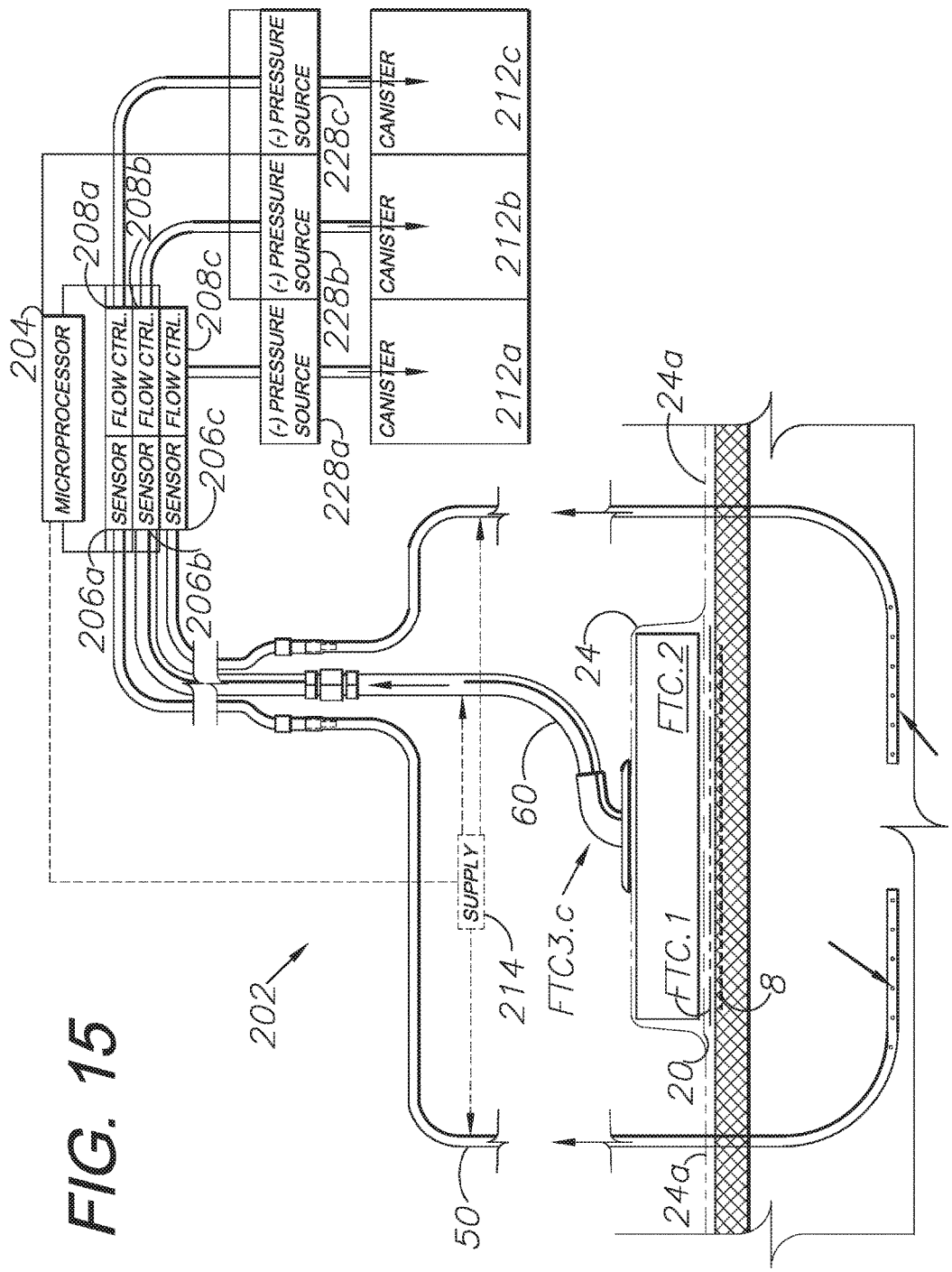
FIG. 15 is a cross-sectional view of the alternative embodiment automated tissue closure treatment system.

FIG. 15 shows the tissue closure system 202 with the microprocessor 204 connected to multiple sensors 206a,b,c each of which is associated with a flow control component, such as a valve, 210a,b,c respectively. Each flow control component 210a,b,c is associated with a respective negative pressure source 228a,b,c, which in turn controls fluid discharge into canisters or reservoirs 212a,b,c respectively. For example, the patient interface 12 can comprise an external patient interface 16 as described above and a pair of deep drainage tubes 50a,b. The patient interface 12 includes an optional supply component 214, which can comprise one or more fluid reservoirs, pumps (manual or powered) and associated controls, which can connect to the microprocessor 204 for system control. The supply component 214 optionally takes to one or more of the tubes 50, 60 for delivering fluid to the patient through the deep drainage tubes 50 or through the external patient interface 16. Such fluids can comprise, for example, antibiotics, and aesthetics, irrigating agents, growth factor, and any other fluid beneficial in promoting healing, countering infection and improving patient comfort.

Figure 16:
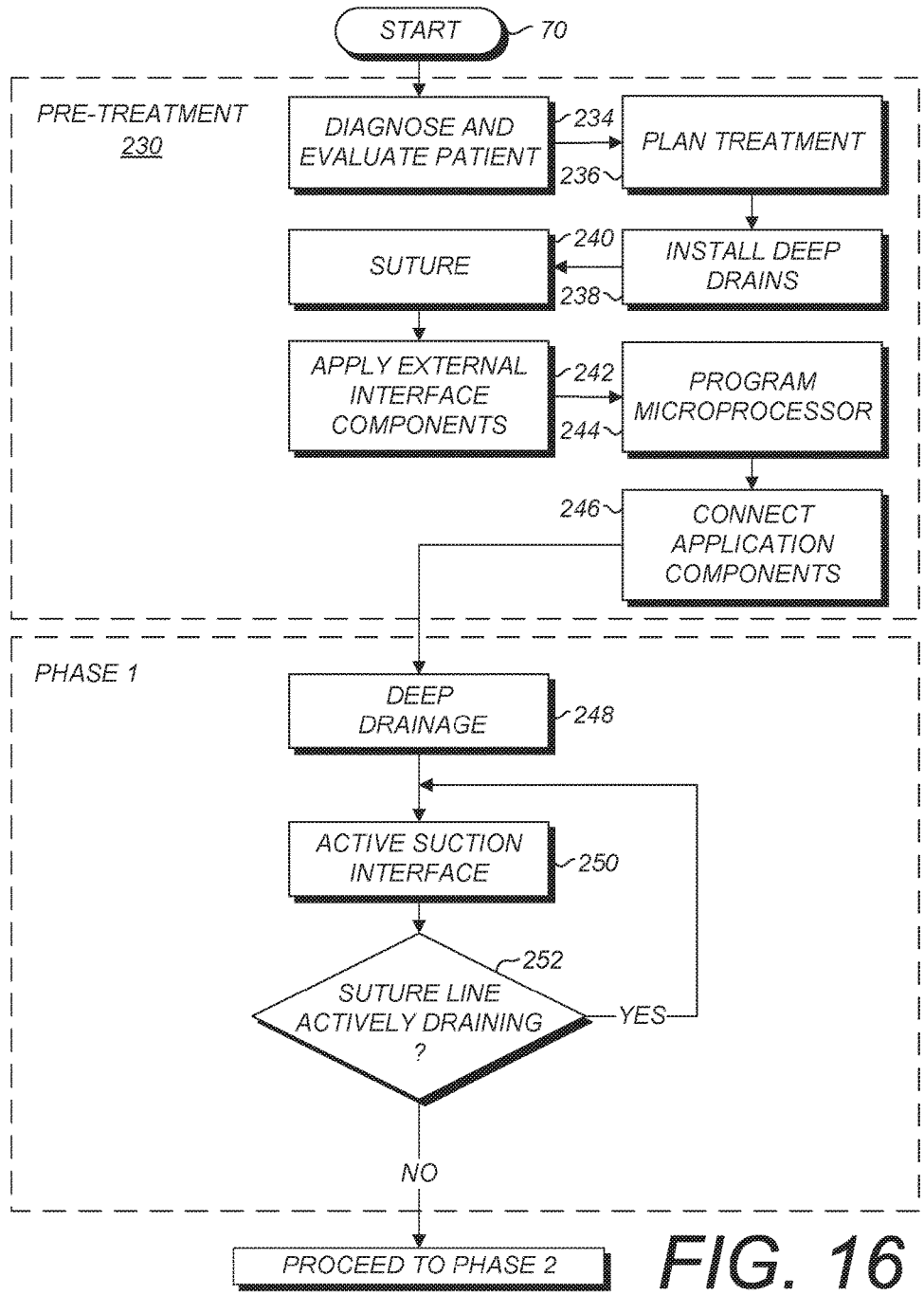
FIG. 16 is a partial flowchart of an alternative embodiment automated tissue closure treatment method embodying the present invention.
Figure 17:
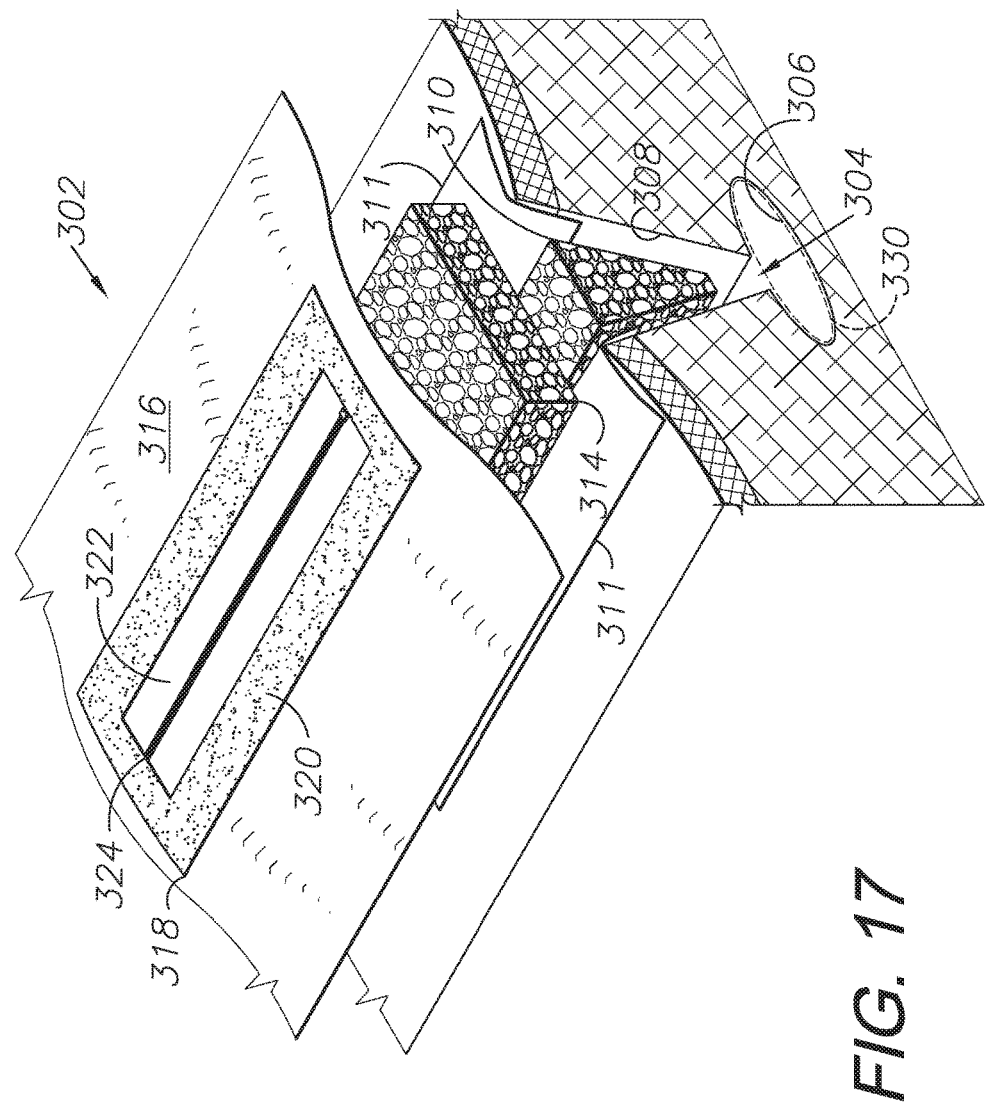
FIG. 17 is a fragmentary, perspective view of a tissue closure treatment system comprising an alternative embodiment of the present invention, with a reclosable access panel.
Figure 18:
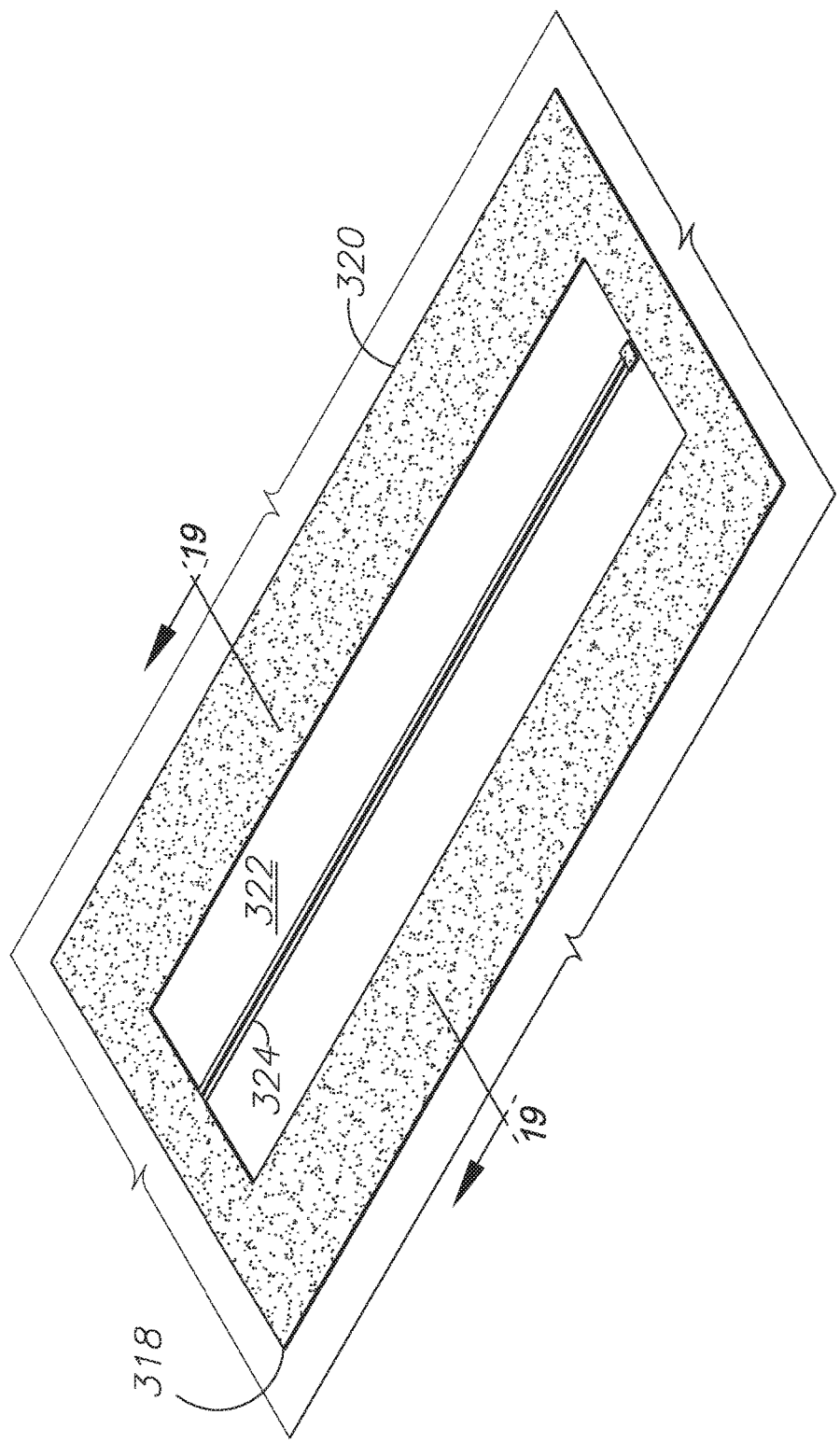
FIG. 18 is a perspective view of the reclosable access panel.
Figure 21:
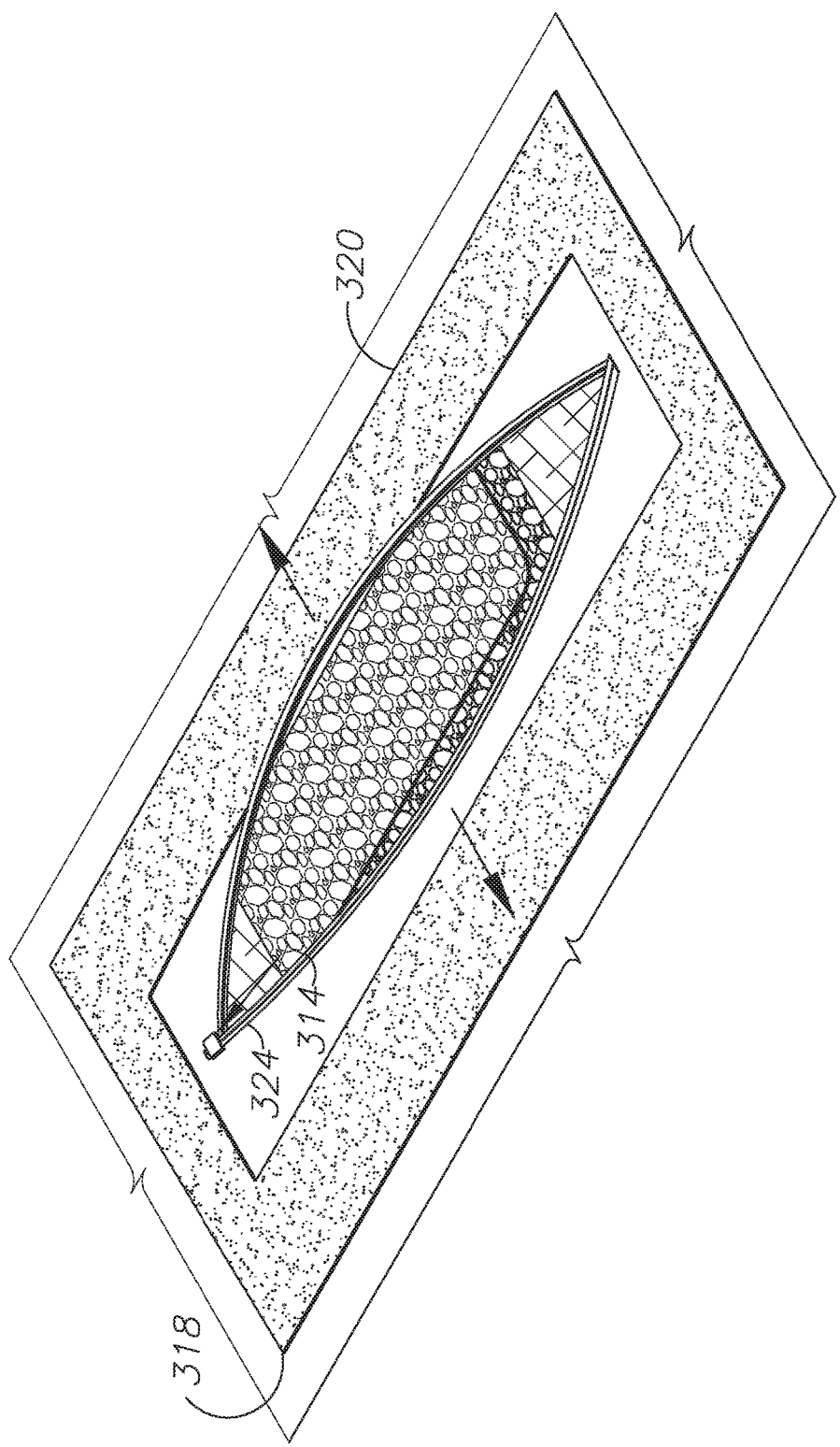
FIG. 21 is a perspective view of the tissue closure system, showing the seal strip open.
Figure 22:
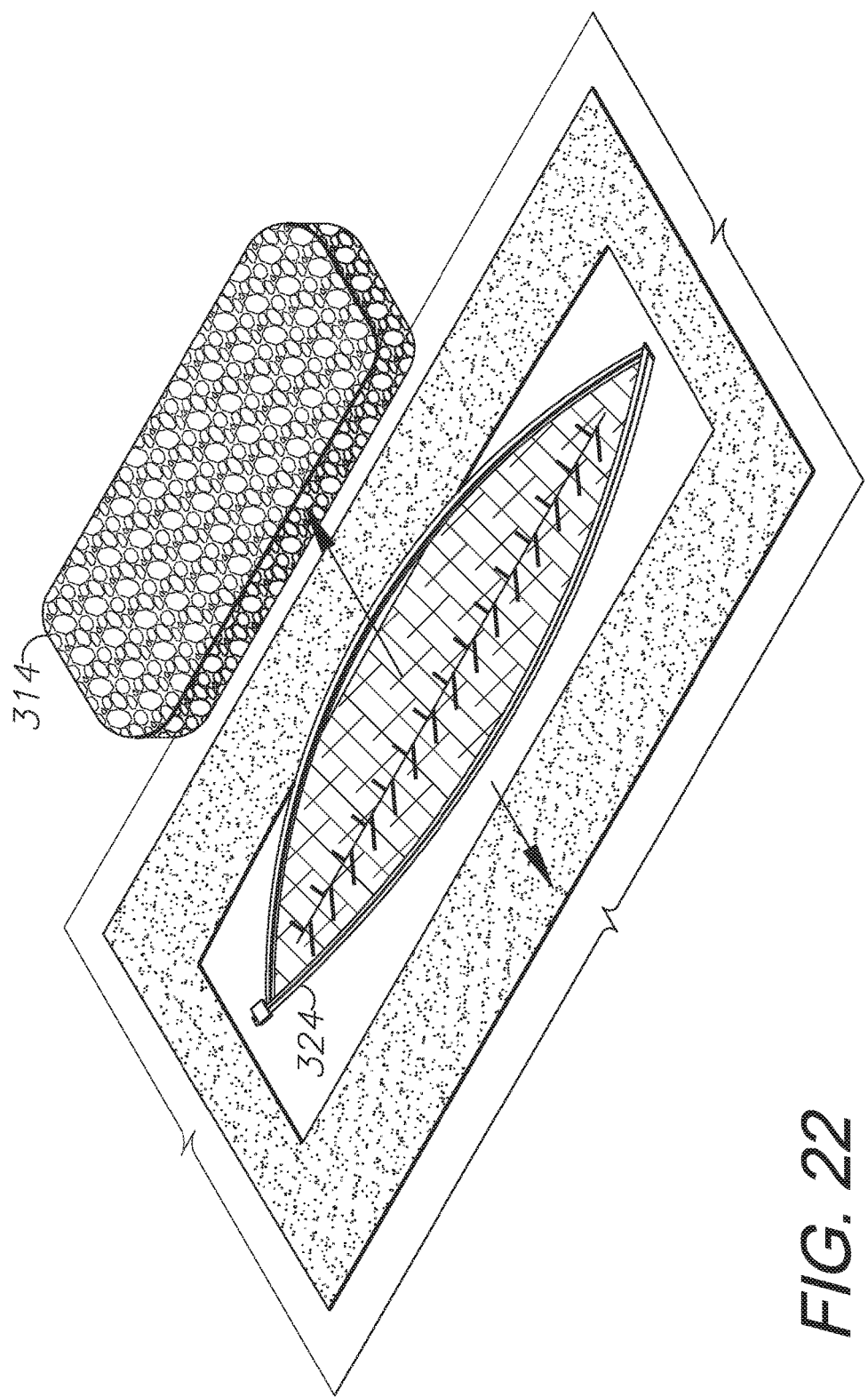
FIG. 22 is a perspective view of the tissue closure system, showing the seal strip open and a foam piece removed.

The methodology of the treatment with the alternative embodiment tissue closure system 202 is shown in FIG. 16 and generally involves modified pretreatment 230 and Phase 1 procedures. From "Start" the method proceeds to a diagnosis/evaluation step 234, a treatment plan step 236, deep drain installation 238, suturing at 240, external interface component application 242, microprocessor programming 244 and connection of the application components at 246, such as connection of the tubing. Phase 1 commences with deep drainage at 248, active suction interface at 250 and a "Suture Line Actively Draining?" decision box 252. If the suture line is actively draining, the method loops back to the active suction interface step 250, otherwise (negative determination at 252) it proceeds to Phase 2.

V. Applications

Without limitation on the generality of useful applications of the tissue closure systems 2 and 202 of the present invention, the following partial list represents potential patient conditions and procedures, which might indicate application of the present invention.

Over closed tissue separations, such as surgical incisions.

Over joints where the incision is subject to movement and stretching, such as arthrotomy, reconstructive procedures, cosmetic procedures, flaps, scar revisions, Total Joint Replacement (TJR) procedures, i.e., hip, knee, elbow, shoulder and foot.

Any wound in an area of thick or unstable subcutaneous tissue, where splinting of skin and subcutaneous tissue might reduce dehiscence of deep sutures.

Wounds over reconstructive procedures in which irregular cavities are created. These include resection of tumors, implants, bone, and other tissues. Changes in length and geometry of limbs, and changes in size, position, and contour of bones and other deep structures.

Wounds in which elimination and prevention of dead space is important.

Treatment of hematomas and seromas.

Amputation stumps.

Abdominal, thoracic, flank, and other wounds in which splinting of the wound might assist closing and mobilizing the patient during the postoperative interval.

Wounds in areas of fragile or sensitive skin, where repeated removal and replacement of tape or other adhesives might produce pain, irritation, or blistering of skin in the vicinity of the wound. Also where dressing changes might produce shear or displacement of tissue so as to compromise primary wound healing.

Wounds in cases where the patient wishes to bathe before the skin has healed sufficiently to allow protection from contamination with bath or shower water.

Wounds subject to contamination with feces, urine, and other body fluids.

Pediatric, geriatric, psychiatric, and neurologic patients and other patients likely to disturb dressings and wounds.

Patients with multiple consultants and care givers, where repeated inspection of the wound might compromise healing.

Deep closure and surface sutures and staples.

Any clean surgical or traumatic incision, open, or fully or partially closed by sutures, or where the skin edges can be apposed to a gap no wider than the width of the negative pressure zone of the dressing, i.e. where the maximum separation is less than or equal to the width of FTC.1 (rayon strip).

In cosmetic and reconstructive surgery, the systems and methods of the present invention can control and conceal the effects of early bleeding, exudation, ecchymosis, and edema of the wound.

In surgery on the limbs, where compression and drainage by this method might eliminate or reduce the need for circumferential compressive wrapping.

Tissue separations that are prone to protracted drainage, such as hip and knee incisions, and tissue separations in patients with health conditions, such as diabetes, that tend to inhibit healing. Shortened hospital stays might result from swelling reduction and control of drainage.

VI. Case Studies

General concept: sequential surface application of foam material (FTC.2) to surgical site and other wounds. Air-drying at the suture line is facilitated by the rayon strip (FTC.1).

Phase 1: deep drainage (drain tube(s)), active or passive; active suction applied to surface PUE foam (placed on top of surgical incision, drains bleeding and exudate from suture line); active suction compresses PUE foam, thus applying positive compression to the entire dissection field; adhesive-lined film underdrape with an MVTR of 3-800 on skin underlying PUE foam; rayon (or other suitable porous wicking material) strip on suture line; similar type of adhesive film overdrape (MVTR of 3-800) overlying PUE foam material.

Duration: approximately 2-3 days, i.e. effective time for active drainage from incision/stitch line to cease and for suture line to dry and heal.

Phase 2: Remove active suction by cutting off (elbow) connector and leave FTC.2 in place. Released from suction, FTC.2 expands against the overdrape and exerts positive pressure differential on the operation site. May maintain continued mild compression throughout Phase 2; residual drainage function through rayon strip and into FTC.2 provides continued drying of suture line. Deep drain tubes remain in place during Phase 2 for active deep drainage.

Duration: approximately three days, i.e. days 3-6 after operation.

Phase 3: remove overdrape and FTC.2; leave underdrape and rayon strip in place; visually observe wound healing progress; transparency desirable.

Duration: several (e.g., up to three) weeks.

Clinical trial confirmation: Closure of surgical site in upper chest area in patient with severe healing problems showed excellent results and rapid wound healing.

Subcuticular (subepidermal) sutures avoid conflict with rayon strip and need for early suture removal, or pressure on skin sutures beneath compressive black sponge.

Option: use pressure transducer for interface pressure mapping of wound site and automate control and monitor pressures, flow, etc.

VII. Alternative Embodiment Tissue Closure System 302

A tissue closure system 302 comprising an alternative embodiment of the present invention is shown in FIGS. 17-22. The system 302 is adapted for closing a wound 304 with an undermined area 306 just above the fascia and an upper tissue separation 308 located primarily in the dermis and in the subcutaneous layer. A wedge-shaped internal fluid transfer component (foam piece) 310 is located in the tissue separation area 308 and is installed between side drapes 311 located on either side of the wound 304. An external fluid transfer component (foam piece) 314 is placed on top of the internal component 310 and the side drapes 311, and is covered by an outer drape 316. An optional innermost foam piece 330 can be located in and sized to fit the undermined area 306 and can transfer fluid and gradient forces to and from the internal foam piece 310.

A reclosable access panel 318 is placed over an opening formed in the outer drape 316 and includes an adhesive-coated perimeter 320 surrounding an adhesive-free center area 322 with a reclosable seal strip 324 extending longitudinally down the centerline thereof. The seal strip 324 includes a rib or bead 326, which is releasably captured in a channel 328 (FIG. 20).

In operation, the reclosable access panel 318 is adhesively secured around its perimeter 322 to the outer drape 316 and provides access to the foam pieces 310, 314 of the dressing system 302. For example, the foam pieces 310, 314 can be changed (FIGS. 21 and 22), treatments can be applied and wound healing progress can be visually monitored.

VIII. Alternative External Dressing 402

FIGS. 23-27 show an external dressing 402, which can be premanufactured or preassembled and used for various wound treatment and closure applications. The dressing 402 includes a foam piece 404 partially enclosed in a rayon covering 406, which includes an open top 408 secured to an upper perimeter 410 of the foam piece 404, for example, by sutures, staples, adhesive or some other suitable mechanical fastener as shown at 411. The dressing 402 is preferably preassembled with an outer drape 414 including a foam-covering central portion 416 and a perimeter, patient-contact skirt portion 418. A tucked margin 420 is formed at the intersection of the drape portions 416, 418 and partially underlies the foam piece 404 in order to protect the skin and prevent the formation of low-pressure, vacuum voids around the edge of the foam piece 404 whereat blistering could otherwise occur. In operation, the dressing 402 can be easily changed by cutting around the margin 420, removing the foam piece 404 and the drape outer portion 416. The wound can thus be inspected, cleaned, debrided, treated, etc. and a new dressing 402 put in place. The patient-contact skirt portion 418 of the original dressing can remain in place.

Figure 23:
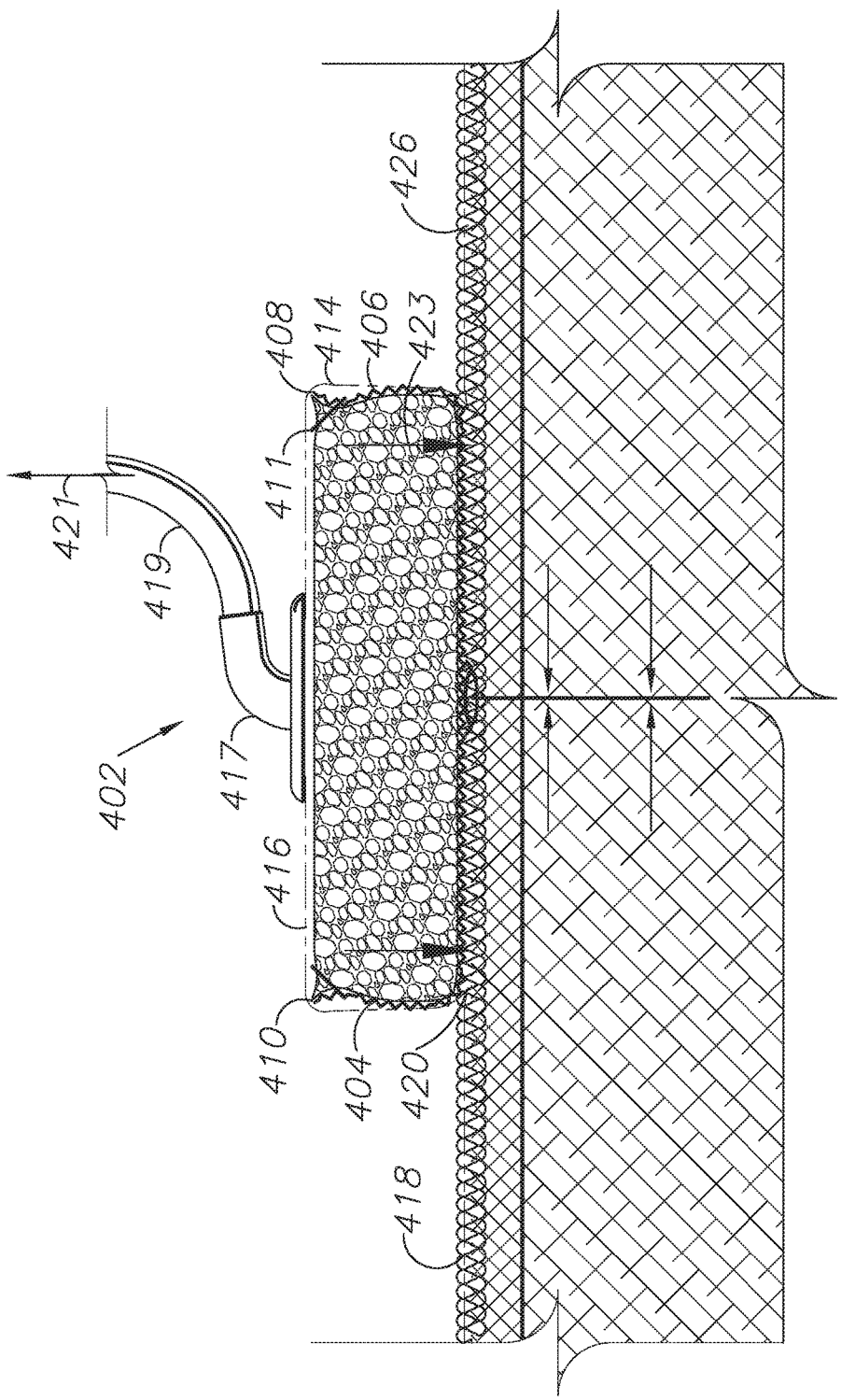
FIG. 23 is a cross-sectional view of an external dressing assembly, which comprises an alternative embodiment of the present invention.

FIG. 23 shows a fluid flow (discharge) directional arrow 421 from an elbow coupling 417 and a discharge tube 419. Alternatively, fluid could be injected into the dressing 402 through the tube 419 and the coupling 417. Hydraulic/pneumatic compressive force arrows 423 are shown in FIG. 23 and represent the downward (i.e. into patient) forces, which can be established by compressing the foam piece 404 under suction and then releasing the negative pressure differential, thus transitioning the dressing to a positive pressure differential. In a positive pressure differential mode of operation, the dressing 402 controls edema by pressing the foam piece 404 against the tissue adjacent to the wound. There are many potential medical benefits from controlling edema in this manner. For example, healing is promoted, scar tissue is minimized and patient discomfort can be reduced.

Figure 24:
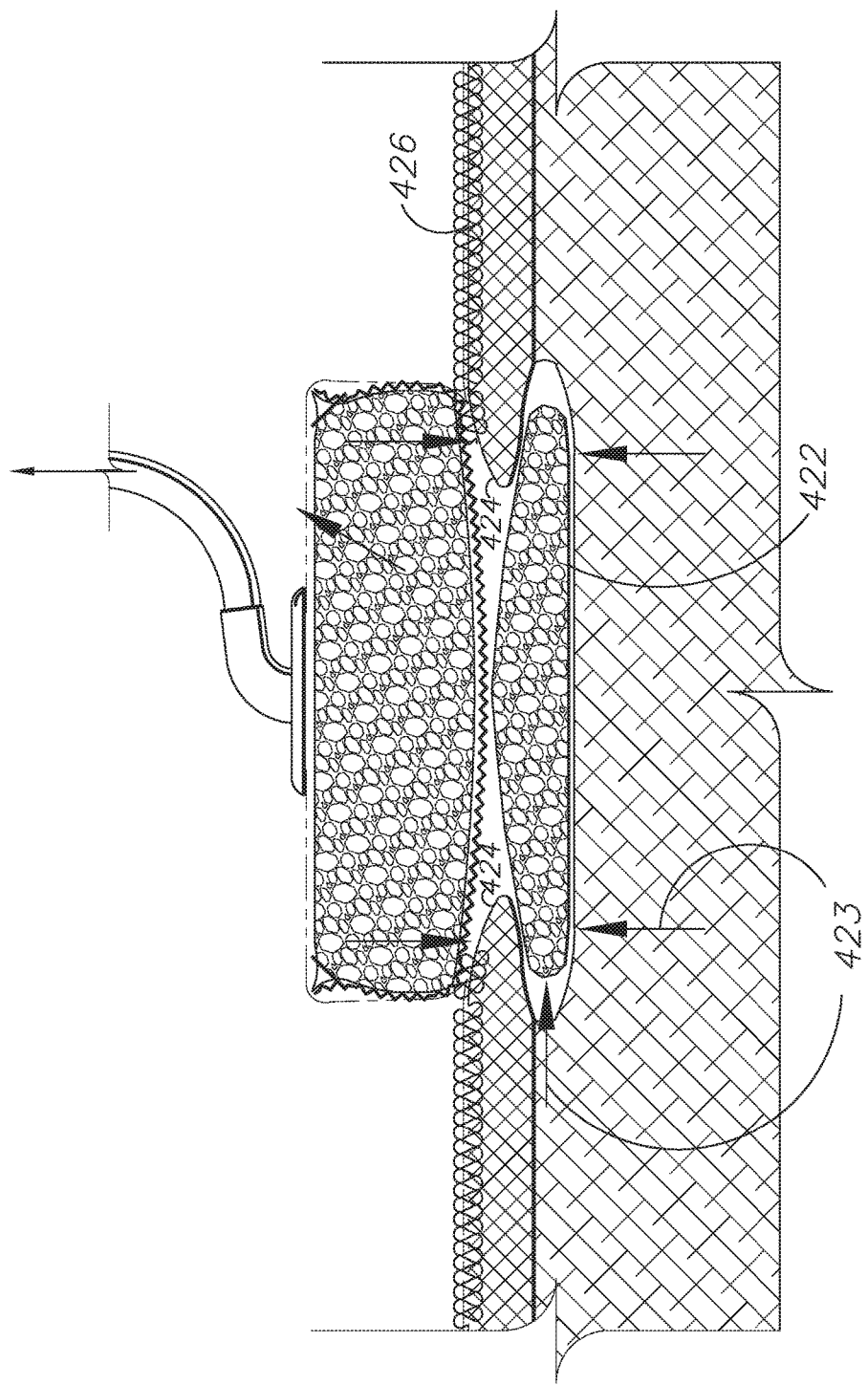
FIG. 24 is a cross-sectional view of an alternative embodiment tissue closure system with internal and external foam pieces.

FIG. 24 shows the external dressing 402 used in conjunction with an internal foam piece 422, which is located below the dermis at the top of the subcutaneous layer. The internal foam piece 422 is adapted for applying a pressure differential within the subcutaneous layer whereby tissue growth and closure are promoted. The inside/outside configuration of the dressing system shown in FIG. 24 can rehabilitate and make pliable a wound edge 424 that has contracted and become hard, immobile and edematous by applying pressure differentials across the external and internal foam pieces 404, 422, such as compression (positive pressure differential) for edema control.

Figure 25:
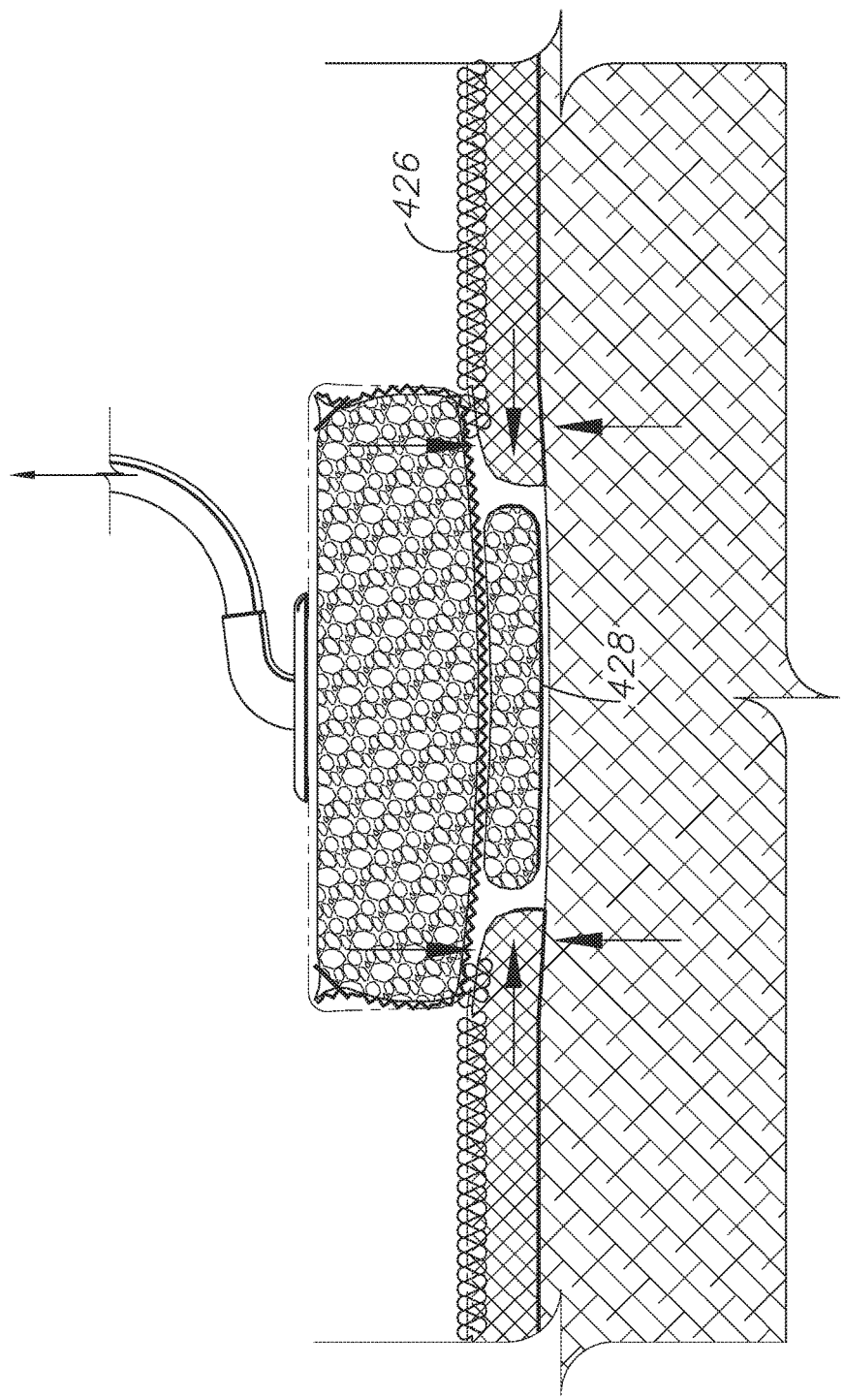
FIG. 25 is a cross-sectional view of the system shown in FIG. 24, showing the progressive healing of tissue in the wound.
Figure 26:
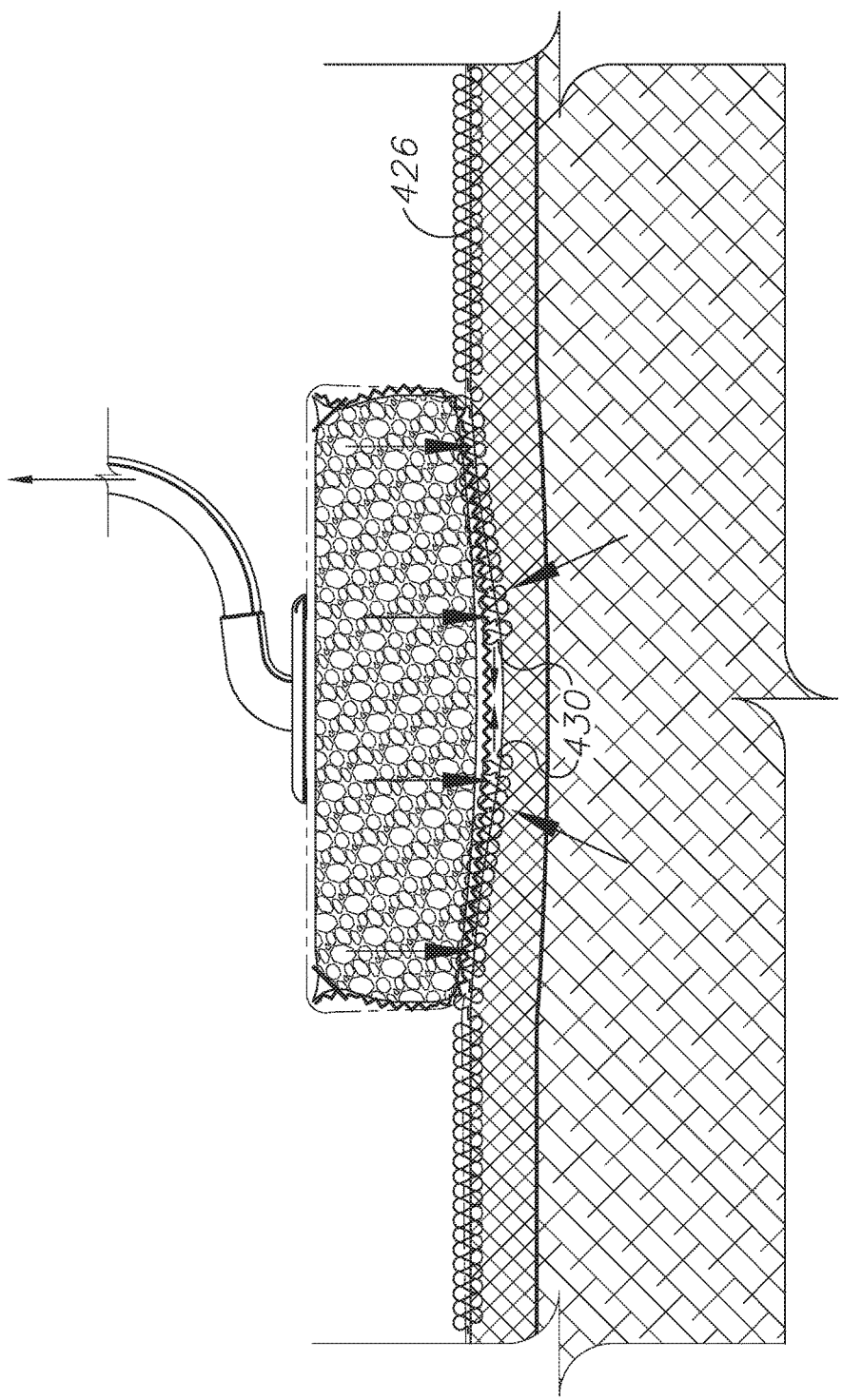
FIG. 26 is a cross-sectional view of the system shown in FIG. 24, showing the reepithelialization of the wound.
Figure 27:
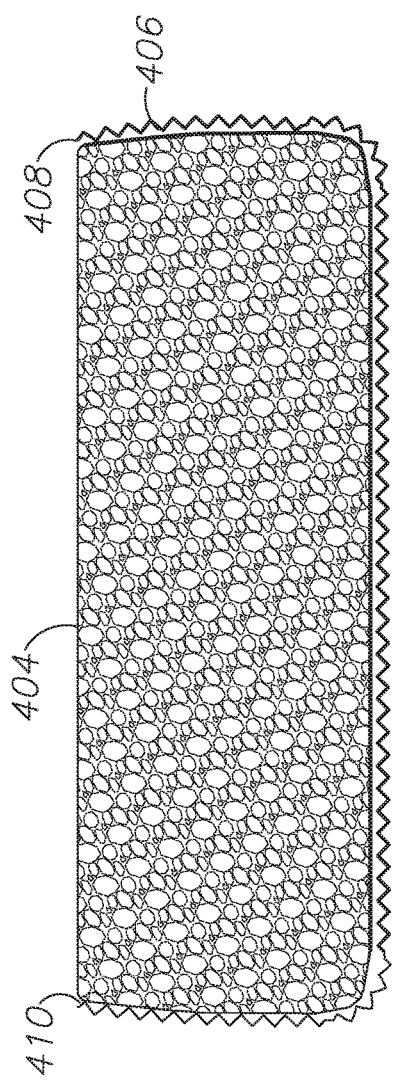
FIG. 27 is a cross-sectional view of a foam piece partially enclosed in rayon.

FIG. 25 shows the wound confined to the dermis 426 with another internal foam piece 428 in place. The subcutaneous layer is substantially healed. FIG. 26 shows the external foam piece 404 in place alone for drawing the wound edges 430 together at the epidermis. FIG. 27 shows the external foam piece 404 covered on the sides and bottom by the rayon covering 406, leaving an open top 408.

IX. Alternative Embodiment Dressing System 502

Figure 28:
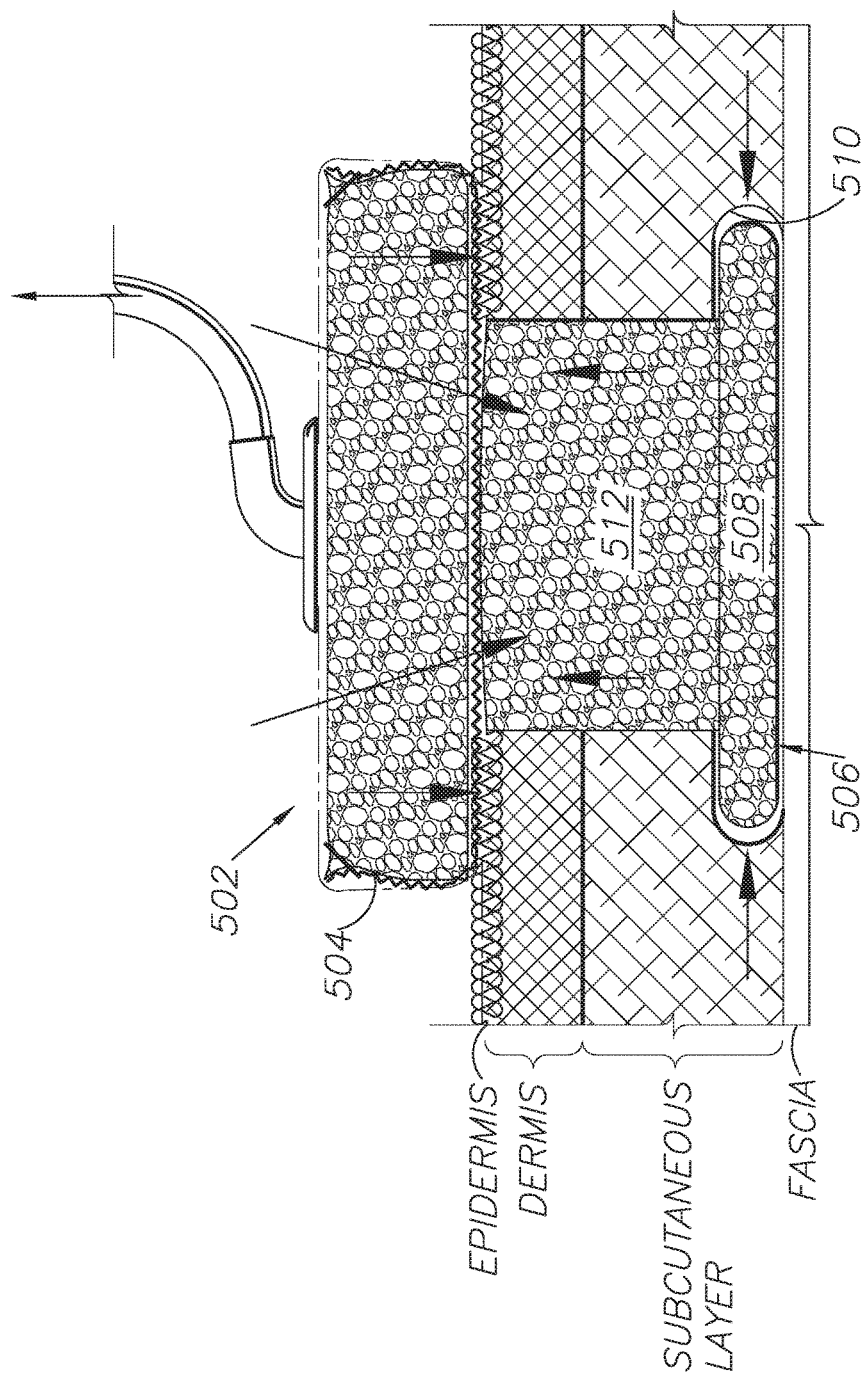
FIG. 28 is a cross-sectional view of an alternative embodiment tissue closure system, with an external foam piece and an internal foam piece assembly.

FIG. 28 shows yet another alternative embodiment internal/external dressing system configuration 502 with an external foam piece 504 similar to the foam piece 404 described above and an internal foam assembly 506 located in the dermis and in the subcutaneous layer. The assembly 506 consists of a proximate internal foam piece 508, which can be located at the bottom of the subcutaneous layer on top of the fascia in an undermined cavity 510 formed by the wound, and a distal internal foam piece 412 located primarily in the dermis and the subcutaneous layer portions of the wound between the external foam piece 504 and the proximate internal foam piece 508.

The dressing system configuration 502 can be configured and reconfigured as necessary to accommodate various wound configurations in various stages of healing. For example, the proximate internal foam piece 508 can be removed when the undermined cavity 510 closes. Likewise, the distal internal foam piece 512 can be removed when the subcutaneous layer and the dermis have healed. Moreover, the foam pieces 504, 508 and 512 can be replaced with different sizes of foam pieces as necessary in connection with dressing changes and as the wound configuration changes. Such sizes and configurations can be chosen to optimize the beneficial effects of pressure gradients (both positive and negative), fluid control, edema control, antibacterial measures, irrigation and other treatment protocols. Still further, the access panel 318 described above can be used in conjunction with the dressing system 502 in order to provide access to the foam pieces thereof and to the wound itself.

Figure 29:
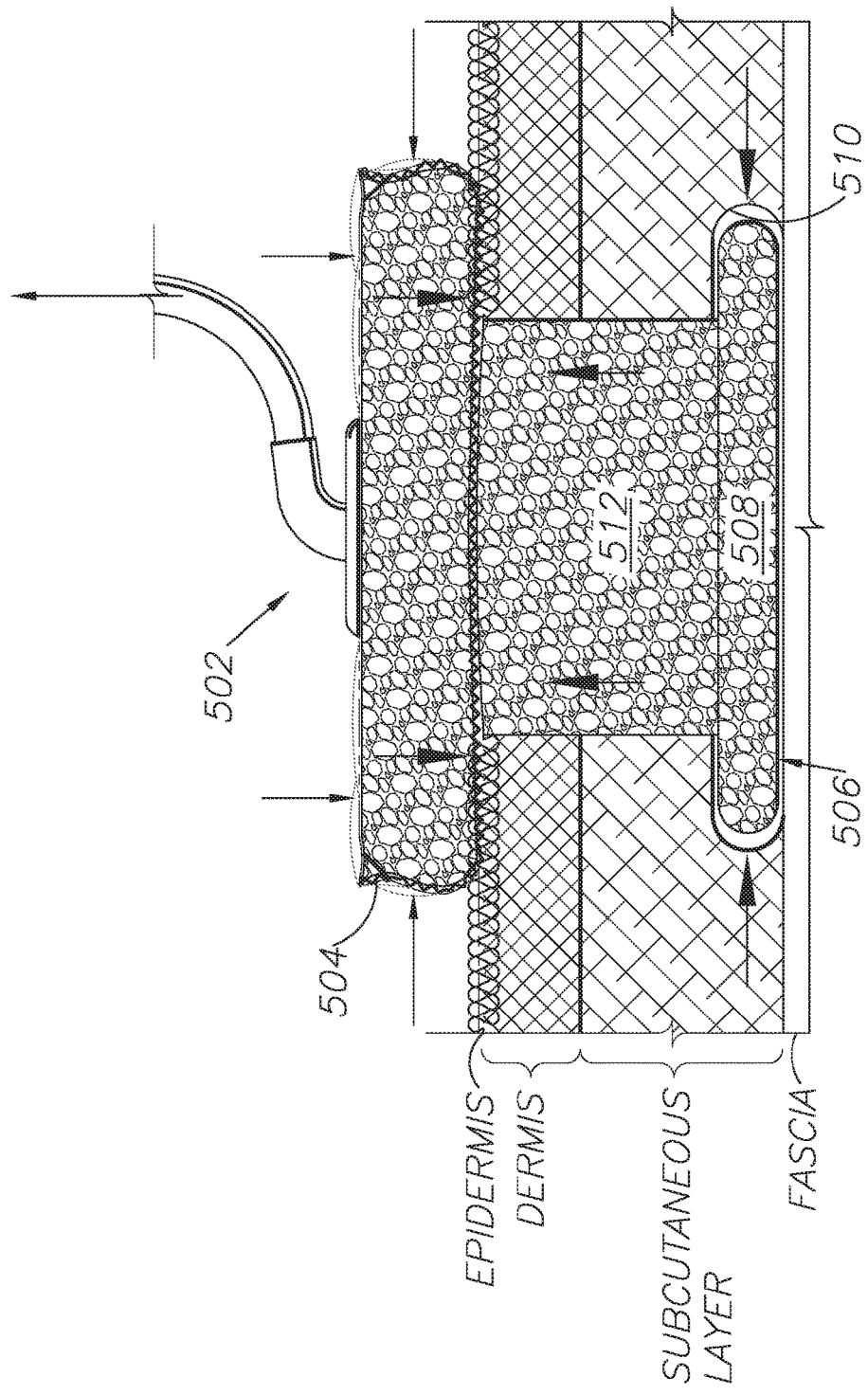
FIG. 29 is a cross-sectional view thereof, shown partially collapsed under ambient atmospheric pressure.
Figure 30:
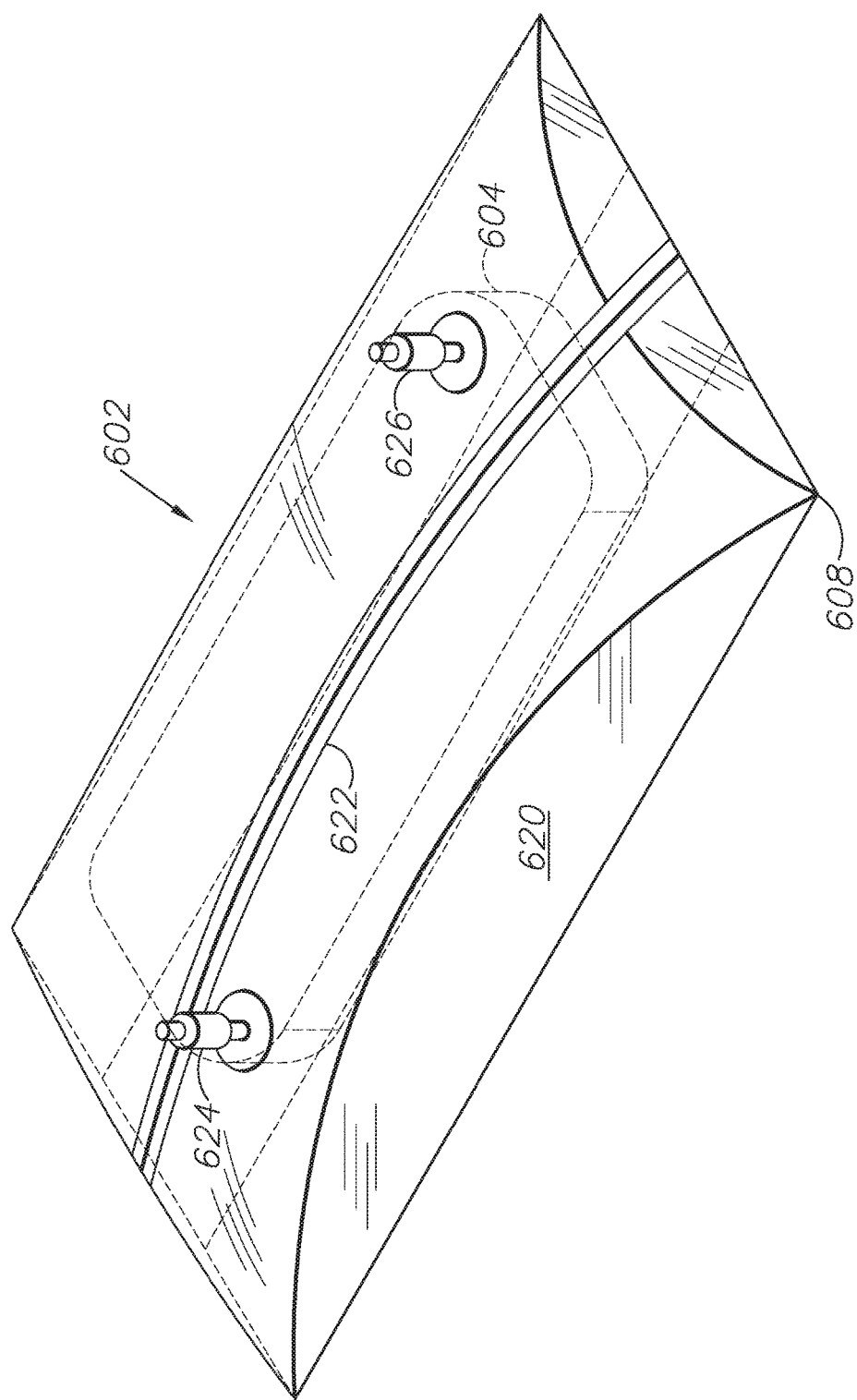
FIG. 30 is a perspective view of an alternative construction dressing with a reclosable seal strip and fluid access ports.

FIG. 29 shows the internal/external dressing system 502 compressed under the vacuum effects of an external vacuum source with the drape 316 drawn tightly down on the compressed outer foam piece 504. Thus compressed, the system 502 is adapted to transfer positive pressure differential, compressive forces to the area of the wound.

X. Alternative Embodiment Dressing Assembly 602

FIGS. 30-37 show a reclosable, preassembled external dressing assembly 602 comprising an alternative embodiment of the present invention. The dressing assembly 602 includes a foam piece 604, which can be completely covered in rayon 606 or some other suitable material with the desired absorbent and/or wicking capabilities. The foam piece 604 also includes a core 605 comprising a suitable material, such as polyurethane, hydrophobic foam. Alternatively, other foam materials with hydrophobic or hydrophilic properties can be utilized. Various sizes and shapes of the foam piece 604 can also be employed, including cutting and trimming it to size during the course of a medical procedure.

Figure 31:
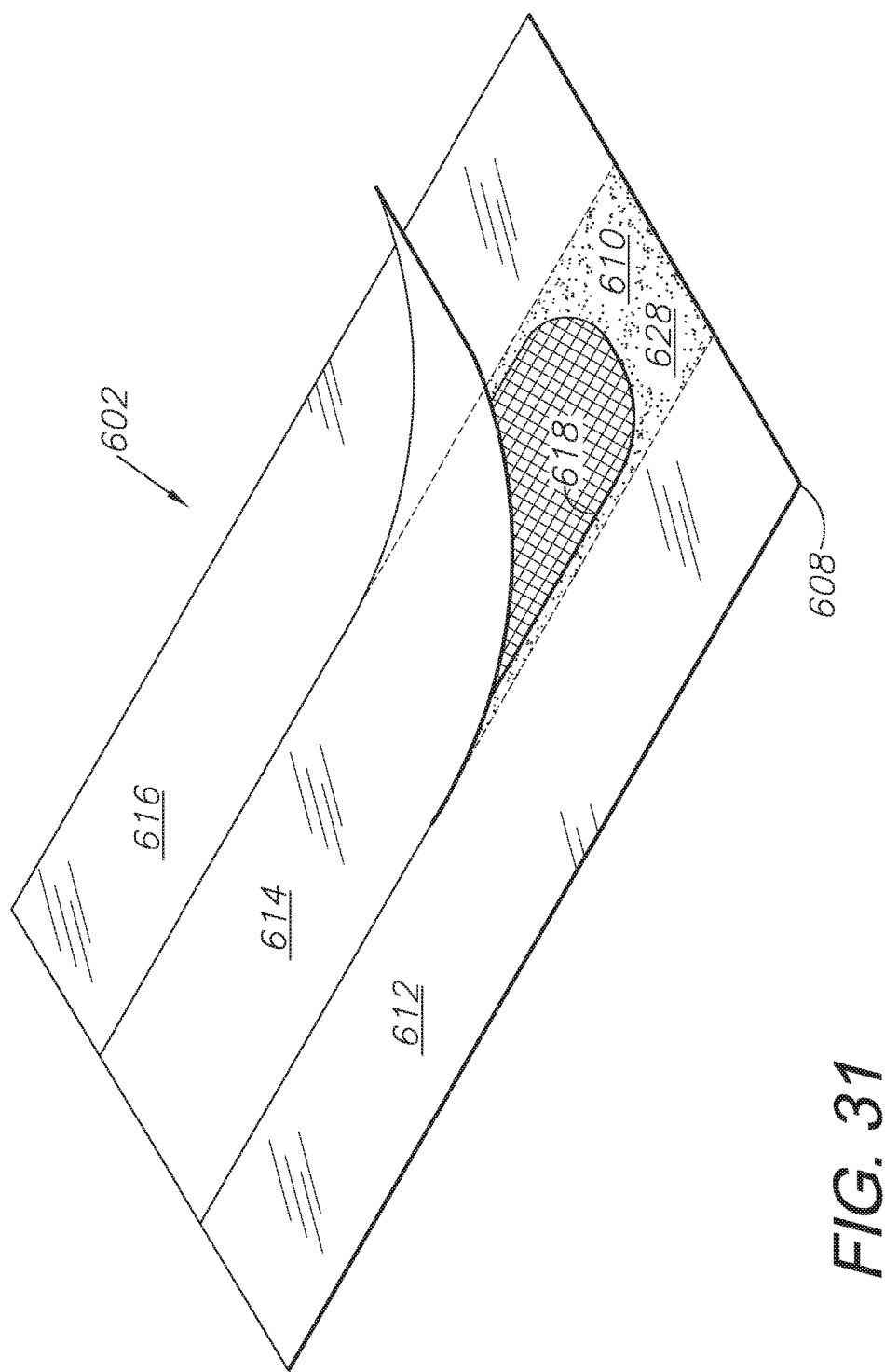
FIG. 31 is a perspective view of the underside of the dressing, showing a middle backing strip being removed.

The foam piece 604 is removably placed in a reclosable sheath 608 including a bottom panel 610 selectively covered by removable, adhesive backing strips 612, 614 and 616 forming a central opening 618. As shown in FIG. 31, a central opening 618 in the bottom panel 610 is initially covered by the center backing strip 614. Removing the center backing strip 614 exposes the foam piece 604 through the opening 618. The reclosable sheath 608 also includes a top panel 620 with a reclosable seal strip 622 extending from end-to-end and generally longitudinally centered. The seal strip 622 can be similar in construction to the reclosable seal strip 324 described above. The top panel 620 also includes fluid ports 324, 326, which can comprise, for example, Leur lock connectors or some other suitable fluid connection device.

The sheath 608 can comprise polyethylene or some other suitable material chosen on the basis of performance criteria such as permeability, flexibility, biocompatibility and antibacterial properties. Various permeable and semi-permeable materials are commonly used as skin drapes in medical applications where healing can be promoted by exposure to air circulation. The sheath 608 can be formed from such materials for applications where continuous vacuum suction is available and the dressing 602 is not required to be airtight.

According to an embodiment of the method of the present invention, a dressing assembly 602 can be premanufactured, or custom-assembled from suitable components for particular applications. In a premanufactured version, the dressing 602 is preferably presterilized and packaged in sterile packaging.

Figure 32:
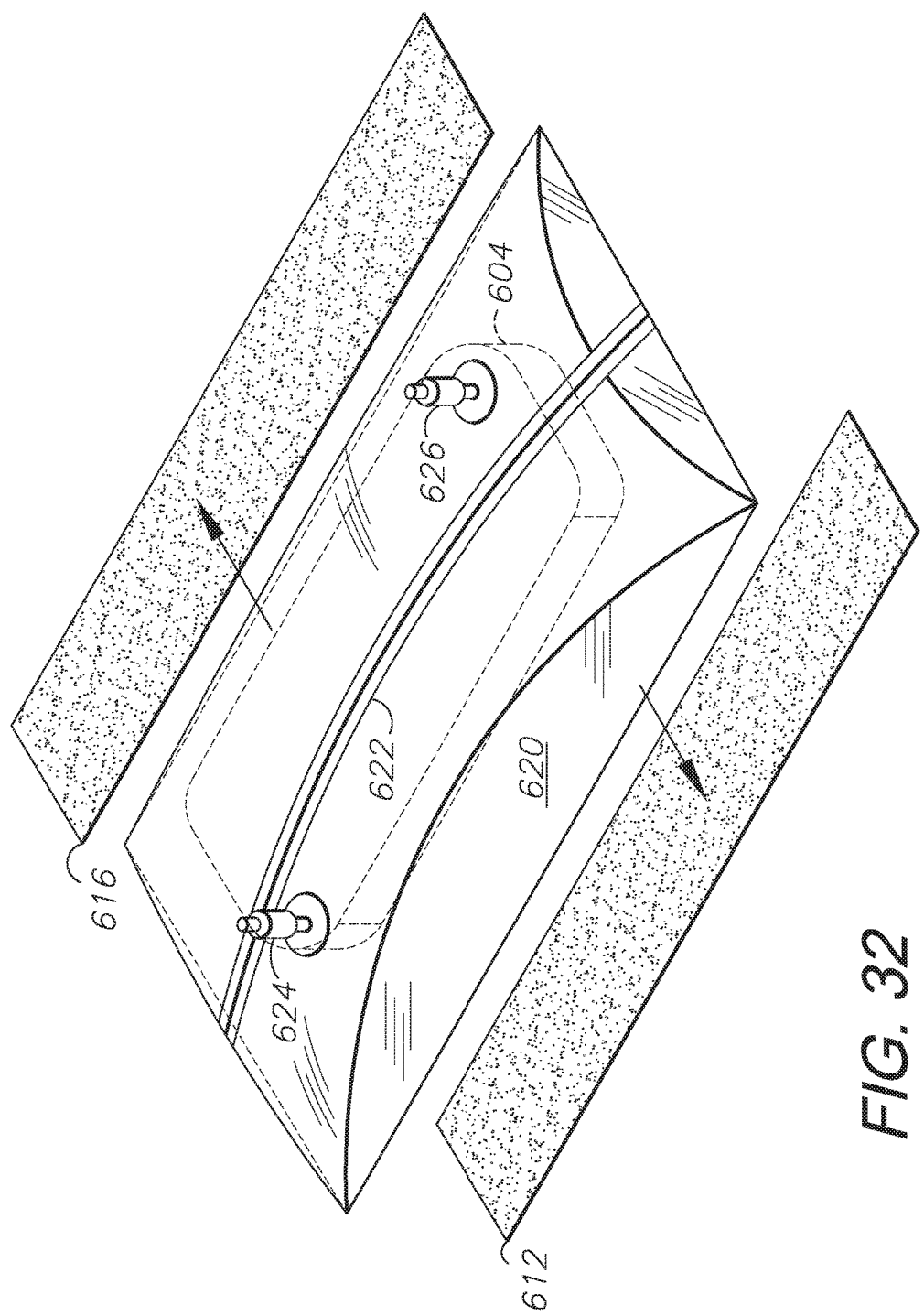
FIG. 32 is a perspective view of the dressing, showing side backing strips being removed.
Figure 33:
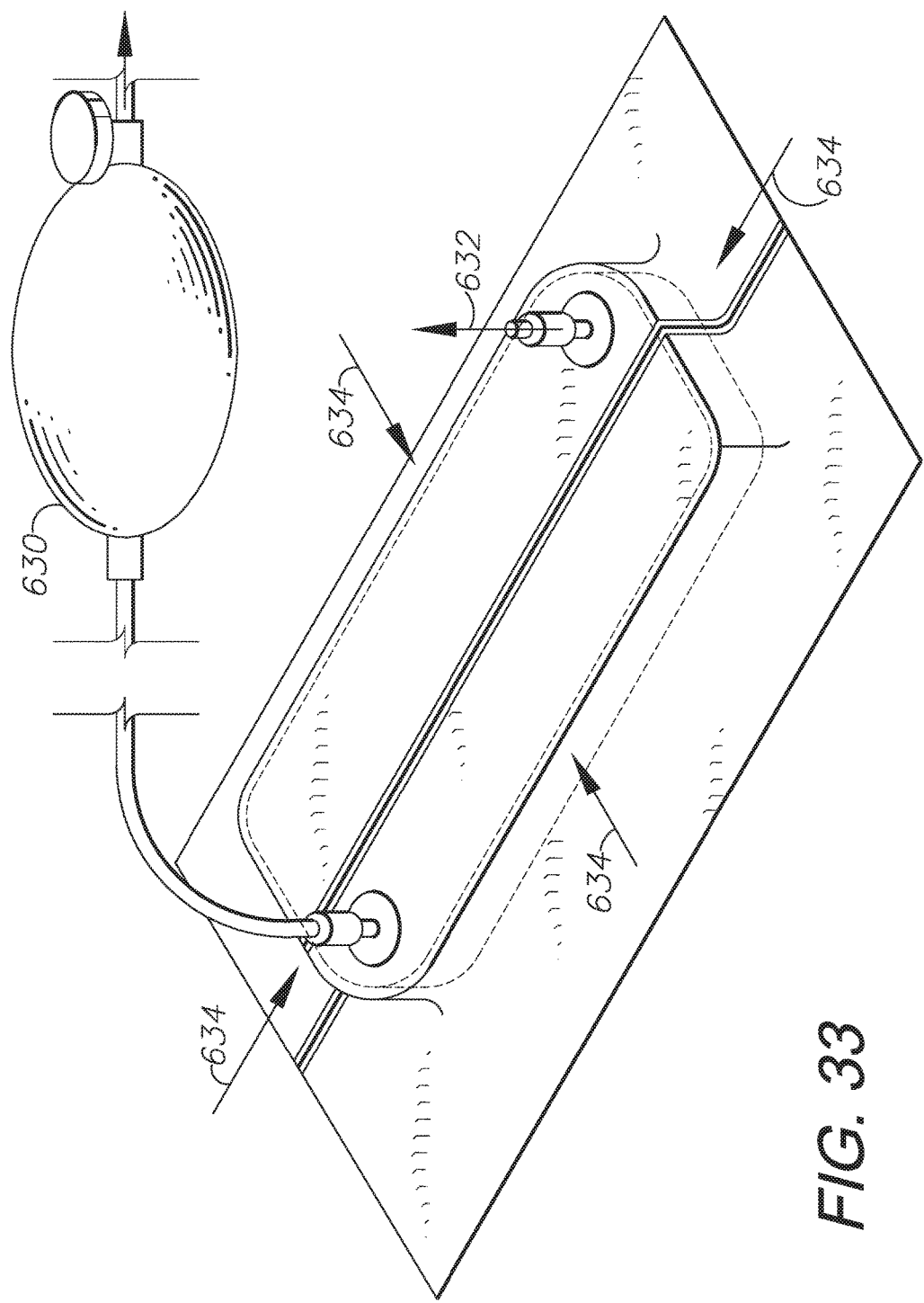
FIG. 33 is a perspective view of the dressing, shown with a squeeze bulb evacuator attached to a fluid port thereof.
Figure 36:
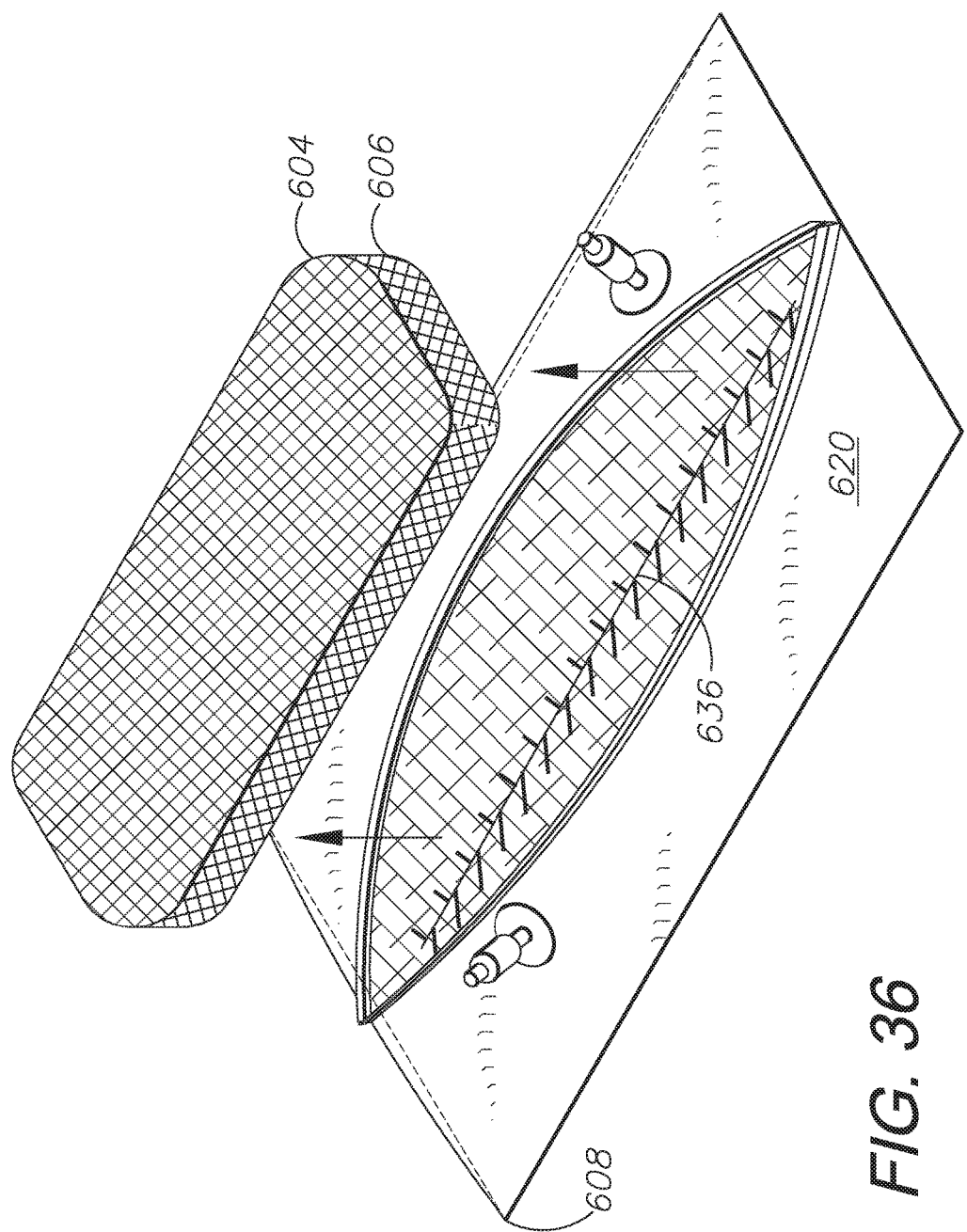
FIG. 36 is a perspective view of the dressing, shown with the foam piece removed.

A common application of the dressing 602 is on a recently-closed surgical incision for controlling bleeding and other fluid exudate. For example, the dressing 602 can be placed on the patient with its bottom panel opening 618 located over a stitch line 636 (FIG. 36). The center backing strip 614 is peeled from the bottom panel 610 to expose the opening 618 and the adhesive 628 on the bottom panel 610 (FIG. 33). The opening 618 provides a fluid transfer, which can also be provided by constructing the sheath bottom panel 610 from a permeable material, or by providing other passage configurations therethrough. The dressing 602 can then be placed on the patient, with the bottom panel adhesive providing temporary fixation. The side backing strips 612, 616 can then be removed, as shown in FIG. 32, and the bottom panel 610 completely secured to the patient.

The fluid ports 624, 626 are adapted for either extraction or infusion of fluids, or both, depending on the particular treatment methodology. For extraction purposes a vacuum source can be attached to one or both of the ports 624, 626, and can comprise a mechanical, powered pressure differential source, such as wall suction. Alternatively, hand-operated mechanical suction can be provided, such as a suction bulb 630 (FIG. 33) or a Hemovac device available from Zimmer Corp. of Warsaw, Ind. Such hand-operated suction devices can accommodate patient mobility and tend to be relatively simple to operate. Powered suction and fluid pump devices can be preprogrammed to provide intermittent and alternating suction and infusion, and to automatically respond to patient condition feedback signals. As shown in FIG. 33, the application of a negative pressure differential (suction) collapses the sheath 608 onto the foam piece 604. The various dynamic fluid forces and fluid movement effects described above can thus be brought into operation and controlled.

Figure 34:
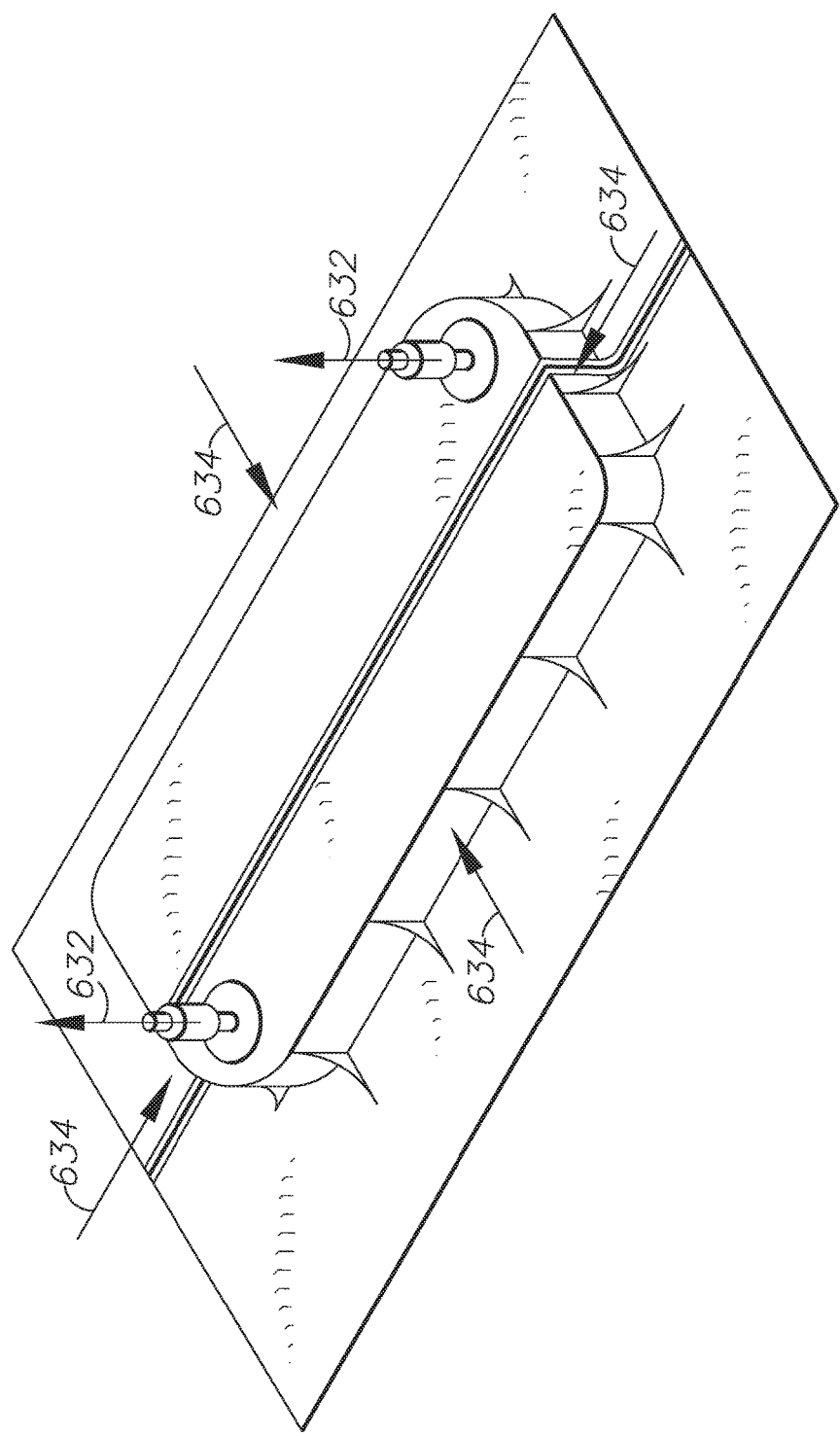
FIG. 34 is a perspective view of the dressing, shown partially-collapsed under atmospheric pressure.

FIG. 34 shows the sheath 608 further collapsing on the foam piece 604 as a result of evacuation from both of the fluid ports 24, as indicated by the fluid flow arrows 632. The ambient air pressure force arrows 634 show the application of this force, which tends to collapse the sheath 608 onto the foam piece 604.

Figure 35:
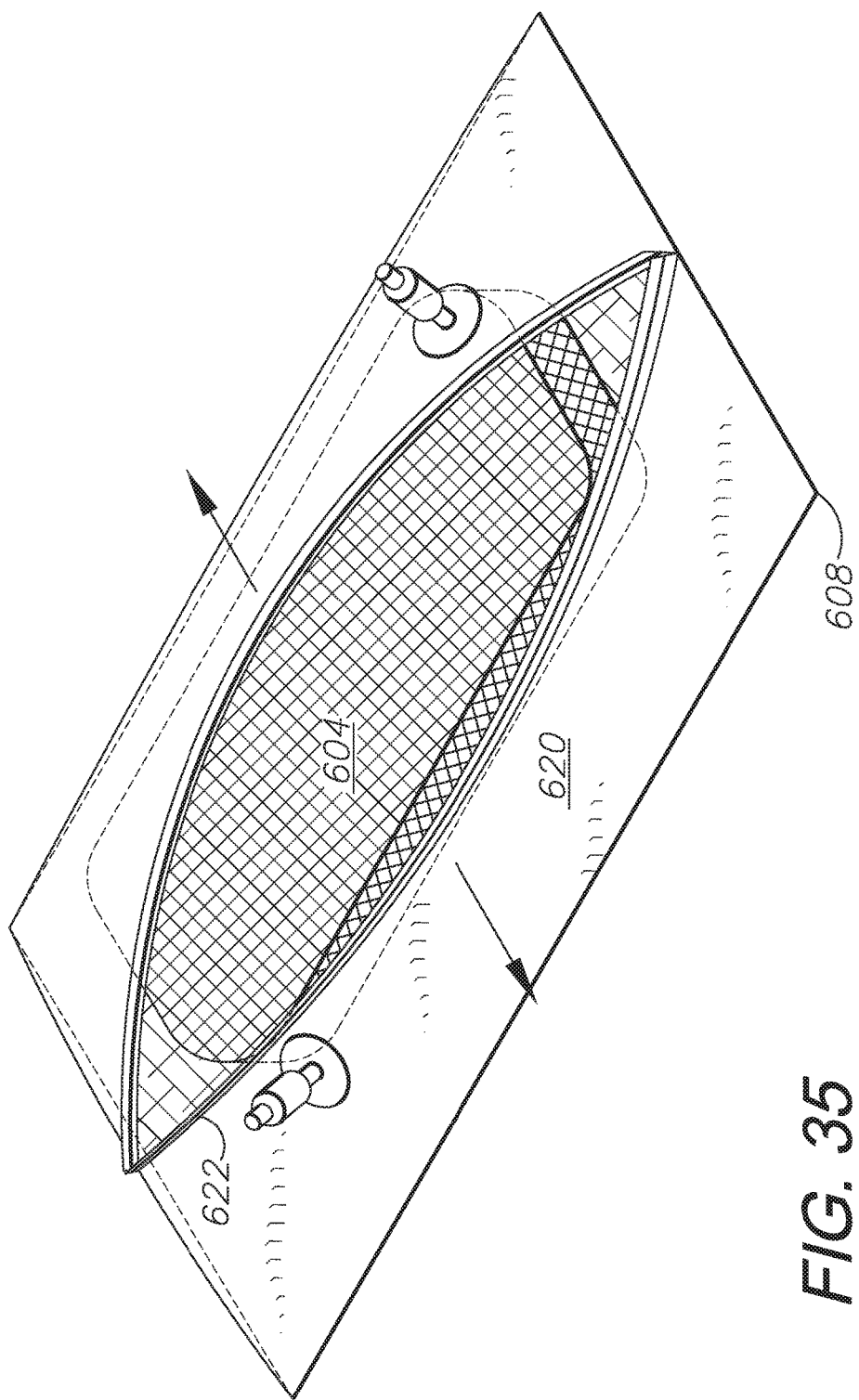
FIG. 35 is a perspective view of the dressing, shown with the seal strip open.
Figure 37:
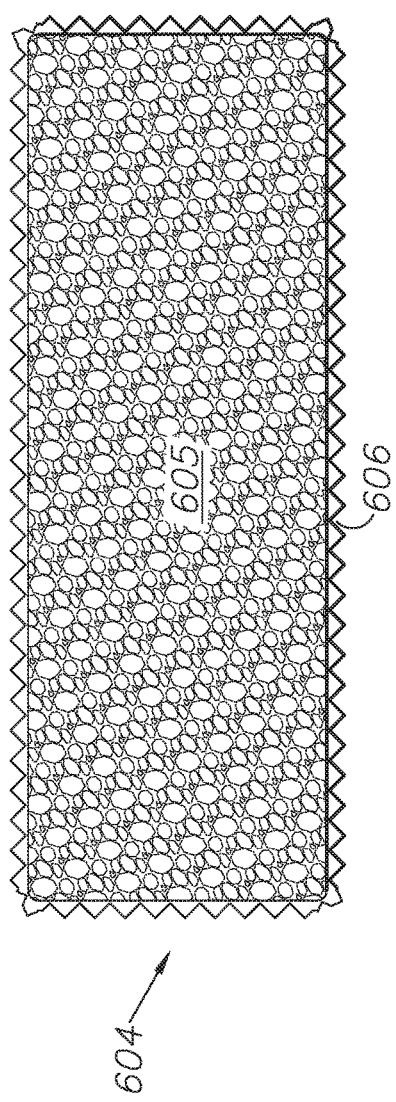
FIG. 37 is a cross-sectional view of a foam piece fully-enclosed in rayon.

FIG. 35 shows opening the seal strip 622 for access to the interior of the dressing 602. The foam piece 604 can then be removed, as shown in FIG. 36, whereby the stitch line 636 can be visually inspected and/or treated. The foam piece 604 can be flipped over or replaced, as necessary. FIG. 37 shows a cross-section of the foam piece 604, which can be completely covered in rayon or some other suitable wicking material 606 in order to accommodate placement of either side against the stitch line 636.

XI. Alternative Embodiment Dressing Assembly 702

Figure 38:
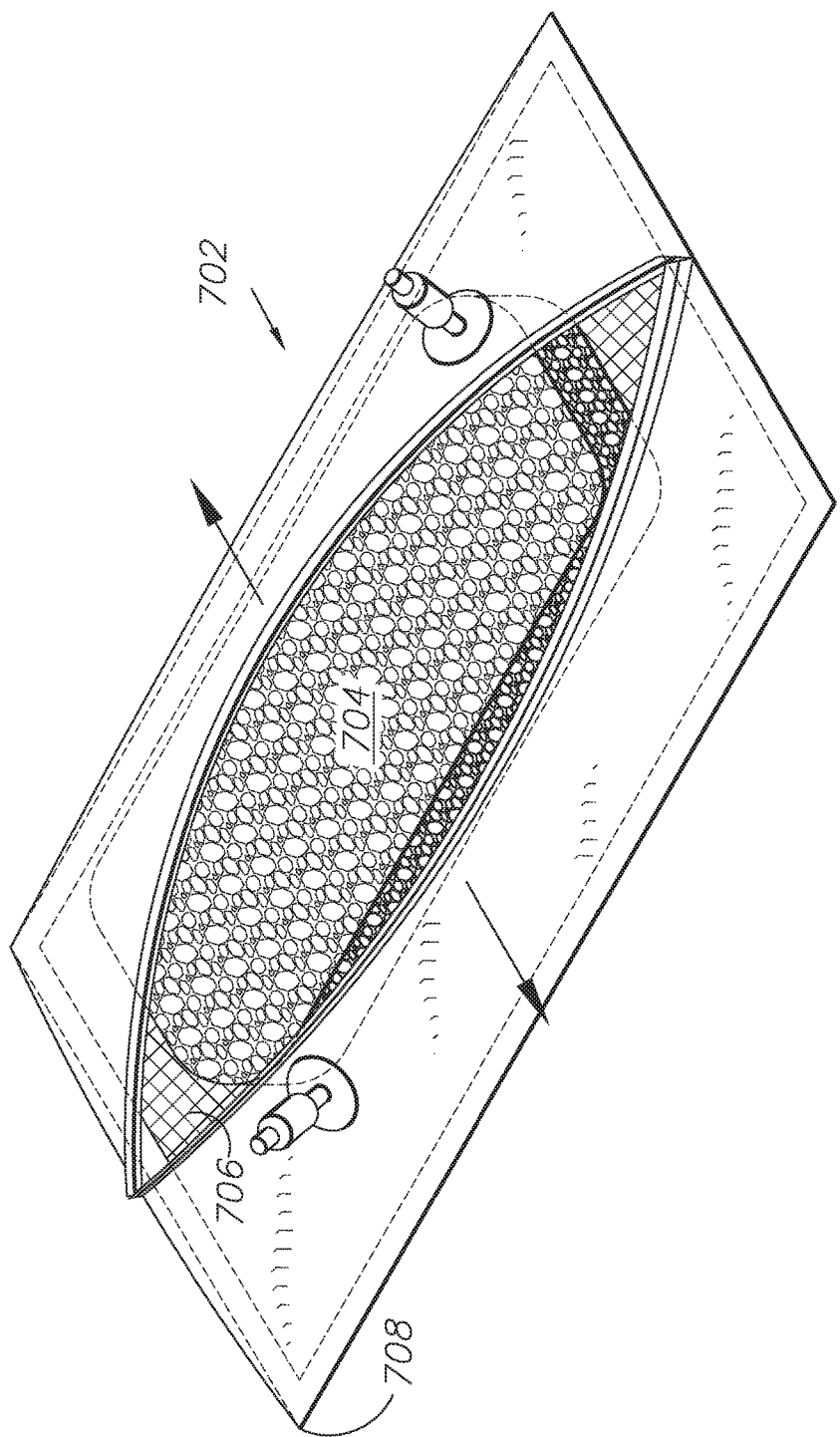
FIG. 38 is a perspective view of an alternative embodiment dressing with a separate liner and foam piece.
Figure 39:
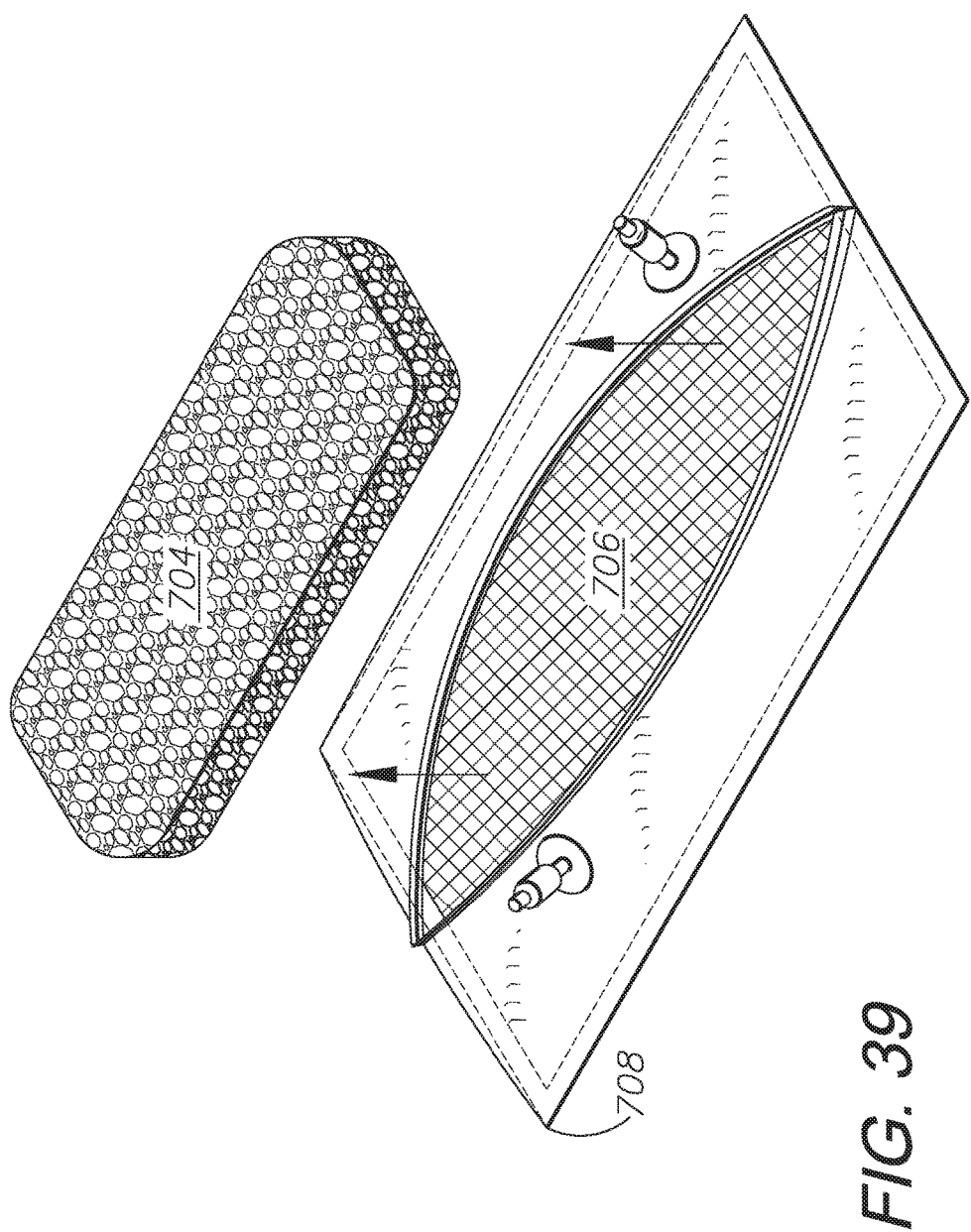
FIG. 39 is a perspective view of the dressing, shown with the foam piece for moved.
Figure 40:
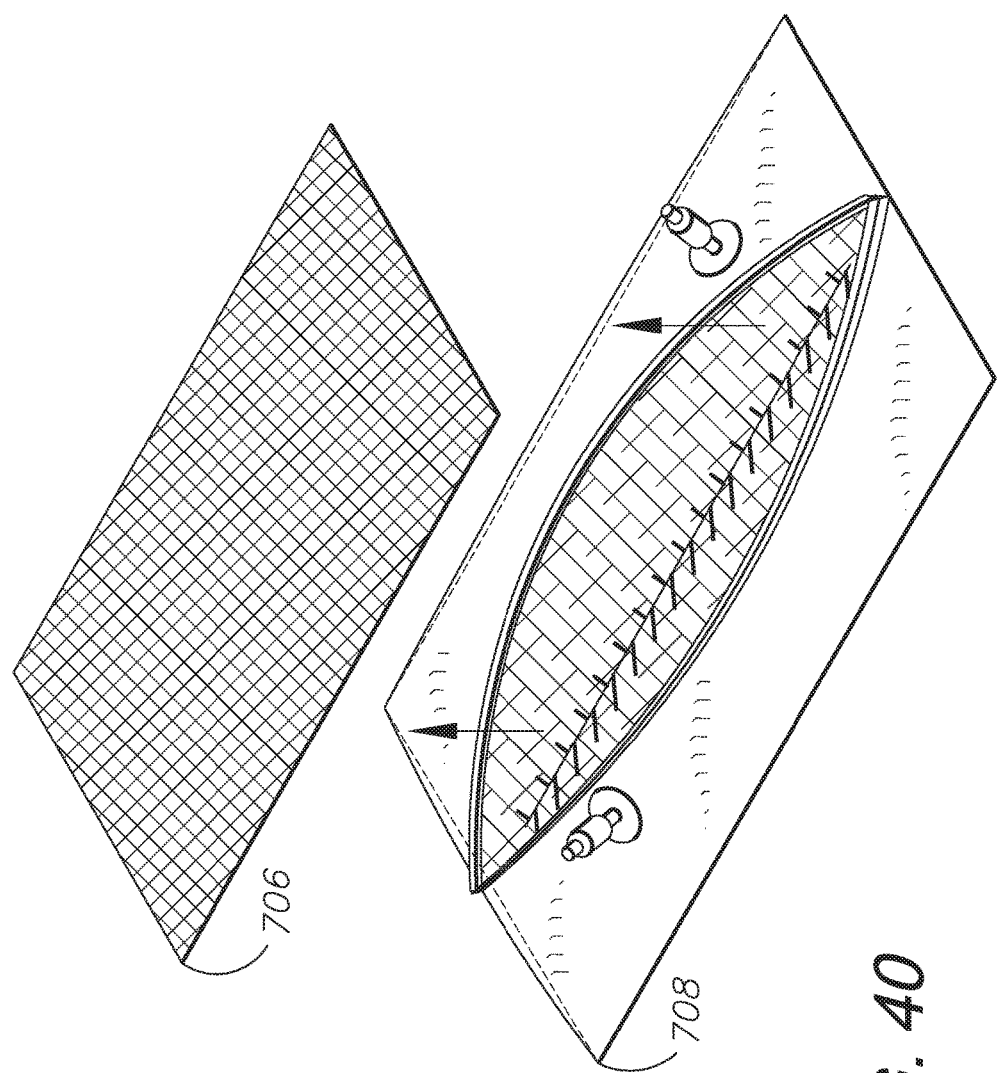
FIG. 40 is a perspective view of the dressing, shown with the liner removed.

FIGS. 38-40 show a dressing assembly 702 comprising an alternative embodiment of the present invention and including a foam piece 704 comprising any suitable hydrophobic or hydrophilic foam material. The foam piece 704 is selectively and removably located in a sheath 708, which can be similar to the sheath 608 described above. A liner 706 can comprise a piece of rayon or some other suitable material adapted to wick fluid from the stitch line 636 into the foam piece 704, and further adapted to isolate the patient from direct contact with the foam piece 704. The liner 706 can be sized to lay flat against the bottom panel of the sheath 708.

In operation, the dressing assembly 702 is adapted to utilize readily available components, such as the foam piece 704 and the liner 706, in a dressing adapted for wound inspection, wound treatment and component change procedures, all without having to remove the sheath or disturb its adhesive attachment to the patient. FIG. 39 shows removing the foam piece 704, which can be flipped over for reuse or replaced. FIG. 40 shows removing the liner 706, which can also be easily replaced. With the liner 706 removed, the stitch line 636 is exposed for stitch removal, inspection, treatment, irrigation and other procedures. The sheath 708 can then be reclosed and vacuum-assisted and/or other treatment can resume.

XII. Alternative Embodiment Dressing Assembly 802

Figure 41:
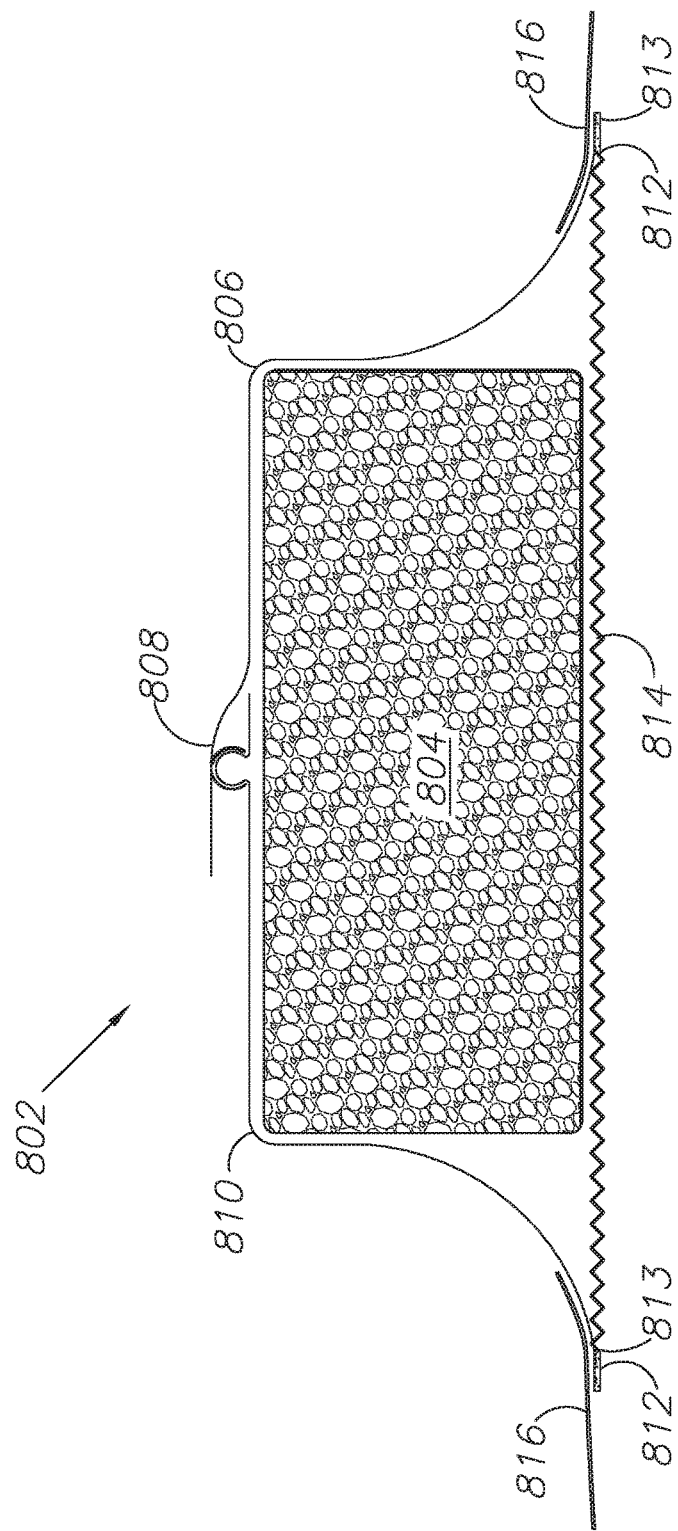
FIG. 41 is a cross-sectional view of an alternative embodiment dressing with a sheath bottom panel comprising a wicking material.
Figure 42:
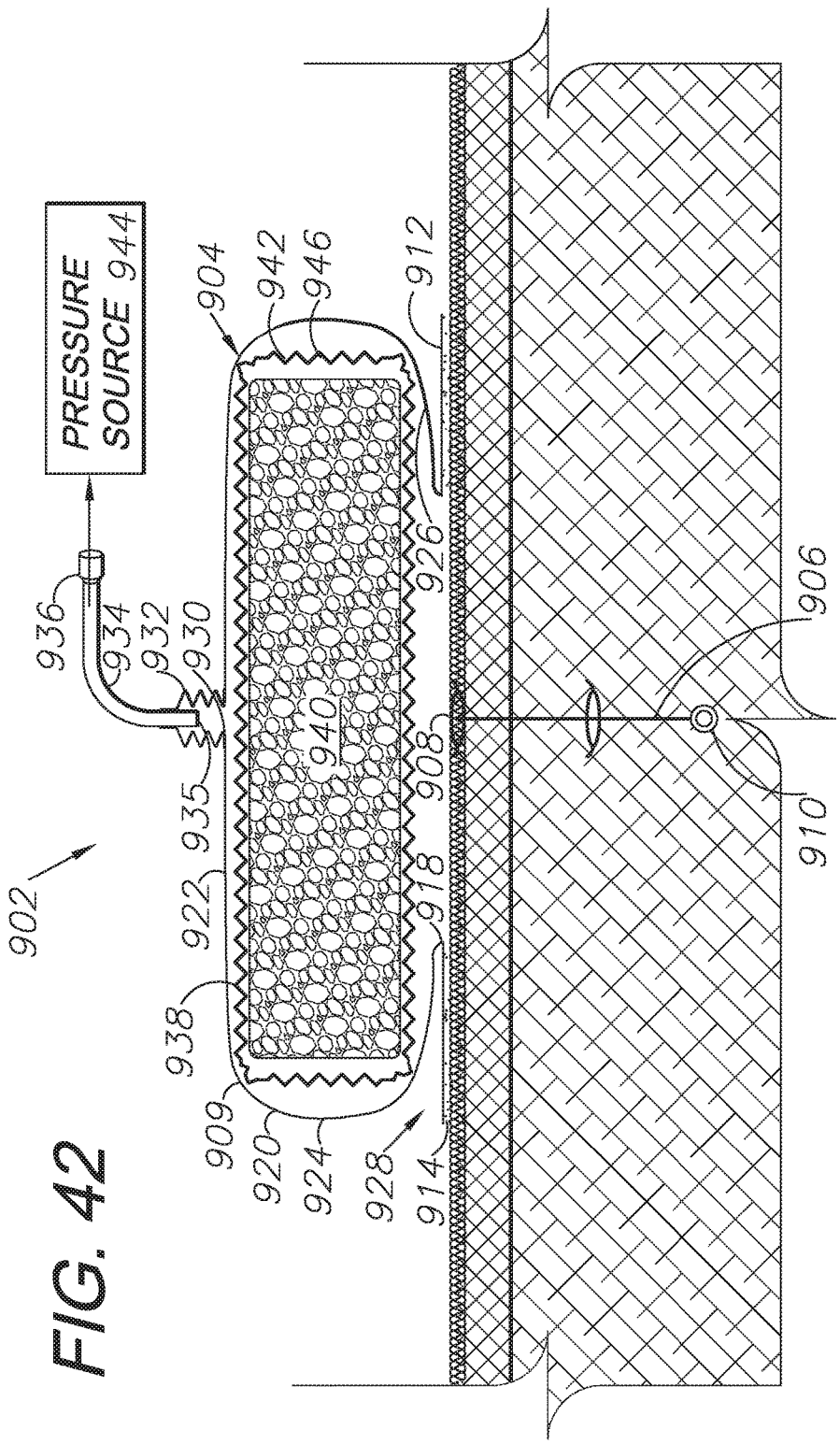
FIG. 42 is a cross-sectional view of an alternative embodiment dressing system with a covered foam-core transfer element.

A dressing assembly 802 comprising an alternative embodiment of the present invention is shown in FIG. 41 and includes a foam piece 804 in a sheath 806 adapted for opening and closing through a reclosable seal strip 808. The sheath 806 includes an upper drape portion 810, which can comprise a suitable semi-permeable or impervious drape material. The sheath 806 includes a perimeter 812, which can be provided with an optional adhesive perimeter seal 813 adapted for providing a relatively fluid-tight seal around the sheath 806. The perimeter seal 813 can be relatively narrow in order to minimize patient discomfort, skin maceration, etc. A bottom panel 814 comprises a suitable wicking material, such as rayon, and extends to the sheath perimeter 812. The materials comprising the dressing 802 can be chosen for permeability or occlusiveness, biocompatibility, hydrophobic or hydrophilic reaction to liquids, bacteriastatic and antimicrobial properties, and other performance-related properties and criteria.

In operation, the dressing 802 is placed on the patient over a wound or stitch line. The perimeter adhesive 813 can provide temporary fixation and sealing. A strip of tape 816 can be placed over the sheath perimeter 812 for securing the sheath 806 in place. Fluid is transferred through the wicking material layer 814 to the foam piece 804 for evacuation through suitable fluid connectors, as described above, which can be attached to a vacuum source. Moreover, the dressing 802 is adapted for providing a positive pressure gradient, also as described above. The seal strip 808 permits access to the foam piece 804 for flipping over or changing, as indicated.

The foam piece 804, the drape upper portion 810 and the wicking material layer 814 can be assembled for independent movement whereby the only attachment among these components occurs around the perimeter 812 where the drape upper portion 810 is connected to the wicking material layer 814. Such independent freedom of movement permits the dressing assembly 802 to reconfigure itself and conform to the patient and various applied forces, such as pressure gradients. The individual components can thus expand and contract independently of each other without distorting the other components or interfering with the performance and comfort of the dressing assembly 802.

XIII Alternative Embodiment Dressing System 902

A dressing system 902 comprising another alternative aspect or embodiment of the present invention is shown in FIGS. 42-46 and includes a dressing 904 adapted for controlling the application of positive, compressive forces and/or negative, suction forces to a patient with an incision-type tissue separation 906. Without limitation of the generality of useful applications of the system 902, the incision 906 can comprise a surgical incision, which can optionally be closed with stitches 908 or other suitable wound-closure procedures, including staples, adhesives, tapes, etc. The incision 906 can include a closed suction drainage tube 910 in the base of the incision, which can be brought to the skin surface through a stab incision, using well-known surgical procedures.

The dressing 904 includes a dressing cover 909 with an optional perimeter base ring 912, which comprises a semi-permeable material with a layer of skin-compatible adhesive 914 applied to a lower face thereof. Prior to application of the dressing 904, the base ring adhesive 914 mounts a release paper backing 916 (FIG. 45) with a release tab 917 (FIG. 44). The base ring 912 defines a central, proximal opening 918, through which the dressing 904 is downwardly open. A cover superstructure 920 includes a distal panel 922, a perimeter 924 generally defining a folding, collapsible edge, and a proximal return ring 926 secured to the base ring 912 around the central opening 918 at another folding, collapsible edge. The base and return rings 912, 926 thus form an invaginated, double-thickness base structure 928 adapted to expand and collapse. A distal cover opening 930 is formed in the distal panel 922 and communicates with a flexible, bellows-shaped collapsible sheath 932, which in turn mounts a length of rigid tubing 934 terminating distally in a connector 936 comprising, for example, a needle-free, leur lock hub or other suitable tubing connection/closure device, such as an air valve. The tubing 934 includes a proximal end 935 communicating with the interior of the dressing cover 909.

An optional transfer assembly or element 938 is positioned within the cover 909 and is exposed through the central opening 918 thereof. The transfer assembly 938 optionally includes a compressible, reticulated core 940, which can comprise, for example, polyurethane ether foam material chosen for its hydrophobic, resilient and memory performance characteristics. The transfer assembly 938 also includes a porous, flexible liner 942 comprising a material such as Owens® rayon surgical dressing with liquid-wicking properties and biocompatibility for direct contact with patients' skin.

Without limitation on the generality of useful applications of the dressing system 902, post-operative incision dressing applications are particularly well-suited for same. The dressing 904 can be preassembled and sterile-packaged for opening under sterile conditions, such as those typically maintained in operating rooms. The central opening 918 can be sized to accommodate the tissue separation 906 with sufficient overlap whereby the perimeter base ring adhesive 914 adheres to healthy skin around the area of the tissue separation 906 and beyond the area of underlying internal operative dissection. Multiple dressings 904 can be placed end-to-end (FIG. 46) or side-by-side in order to effectively cover relatively long incisions 950. In such multiple dressing applications, the stitch line 950 can be covered with an intervening barrier layer strip 948 at locations where the adhesive-coated base ring crosses same for purposes of patient comfort. The barrier layer strips 948 can comprise, for example: Xeroform® gauze available from Integrity Medical Devices, Inc. of Elwood, N.J.; Vaseline® gauze; or straps of Owens® rayon.

The base ring adhesive 914 preferably forms a relatively fluid-tight engagement around the treatment area. Optionally, the base ring 912 can comprise a suitable semi-permeable membrane material, with suitable breathability characteristics for enhancing patient comfort and avoiding maceration in the contact areas. A suitable differential pressure source 944 is coupled to the tubing connector 936. Without limitation, the pressure source 944 can comprise automated and manual pressure sources. For example, automated wall suction is commonly available in operating rooms and elsewhere in health-care facilities.

For post-operative incision dressings, operating room wall suction can be attached to the connector 936, the dressing 904 evacuated, and the wall suction disconnected whereby the connector 936 seals the system. It will be appreciated that a "steady-state" condition of equilibrium can be achieved with positive, ambient air pressure acting externally on the dressing cover 909 and the transfer assembly 938 compressed internally, and thus exerting compressive forces on the incision 906 and the surrounding area via compressive force arrows 939 (FIG. 43).

For example, FIG. 43 shows the dressing 904 collapsed with the rayon dressing liner 942 extending beyond the polyurethane ether foam core 940 and forming a double-thickness liner perimeter 946 located within the double-folded cover perimeter 924. In this configuration any liquid exudate from the incision 906 is effectively transferred by wicking action of the rayon liner 942 away from the incision 906 via fluid transfer arrows 941. Serosanguineous fluid emissions can be expected from an incision line for a short period, commonly a day or two, after an operation. The wicking action of the rayon liner 942, coupled with the slight ambient air circulation admitted through the semi-permeable base ring 912, cooperate to maintain the incision 906 and the healthy skin around it relatively dry in order to avoid maceration. The pressure differential provided by components of the dressing 904 can also contribute to extraction and removal of wound exudates, in cooperation with the wicking action described above. With the dressing 904 in its compressed configuration (FIG. 43), the tubing proximal end 935 can engage and be pushed into the transfer element 938 for direct fluid transfer therebetween.

The evacuated dressing 904 provides a number of medical incision-closure and healing benefits. The stabilizing and fixating effects on the incision and the surrounding tissue resulting from the forces applied by the dressing 904 tend to promote contact healing, as opposed to gap healing or healing wherein opposing edges are sliding and moving one on the other. Moreover, edema and ecchymosis control are accomplished by exerting positive pressure, compressive force via the compressive force arrows 939 in the compressed core 940, which tends to resume its pre-compression shape and volume as pressure is released within the dressing 904. Thus, the effects of restricted or controlled leakage, for example around the base ring 912, tend to be offset by the controlled expansion of the core 940. The limited air movement through the dressing 904 can be beneficial for controlling internal moisture, reducing maceration, etc.

The system 902 is adapted for adjustment and replacement as necessary in the course of closing and healing an incision. Additional air displacement can be applied via the connector 936 from automated or manual sources. Wall suction, mechanized pumps and other automated sources can be applied. Manual vacuum sources include: squeeze-type bulbs (630 in FIG. 33); (Snyder) Hemovac® evacuators available from Zimmer, Inc. of Warsaw, Ind.; and vacuum tubes. Inspection of the incision 906 can be accomplished by making an L-shaped cut in the dressing cover superstructure 920 and extracting or lifting the transfer assembly 938, thereby exposing the incision 906. The transfer assembly 938 can be flipped over or replaced. The dressing 904 can then be resealed by applying a replacement portion of the cover 909, whereafter the dressing 904 can be evacuated as described above. After treatment is completed, the cover superstructure 920 can be cut away and the transfer assembly 938 can be discarded. The base ring 912 can be peeled away from the skin, or simply left in place until the adhesive 914 releases.

The stabilizing, fixating and closing forces associated with the dressing 904 tend to facilitate healing by maintaining separated tissue portions in contact with each other, and by controlling and/or eliminating lateral movement of the tissue, which can prevent healing. The positive pressure, compressive force components associated with the forces in the dressing 902 tend to close the tissue separation 906 and retain the opposing tissue edges in fixed contact with each other whereby healing is promoted. Various other dynamic forces tending to displace the wound edges relative to each other can be effectively resisted.

XIV. Alternative Embodiment External Dressings 1002, 1012

Figure 47:
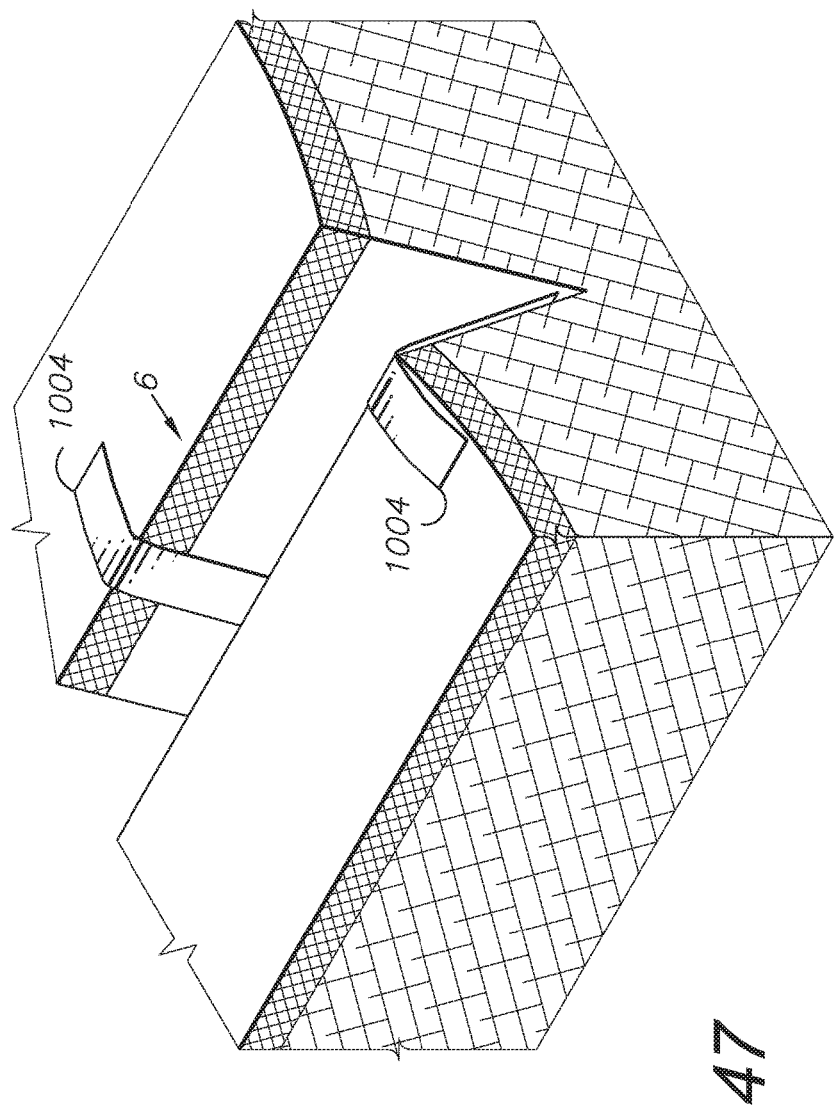
FIG. 47 is a perspective view of a wound with drain strips installed in preparation for closure.
Figure 48:
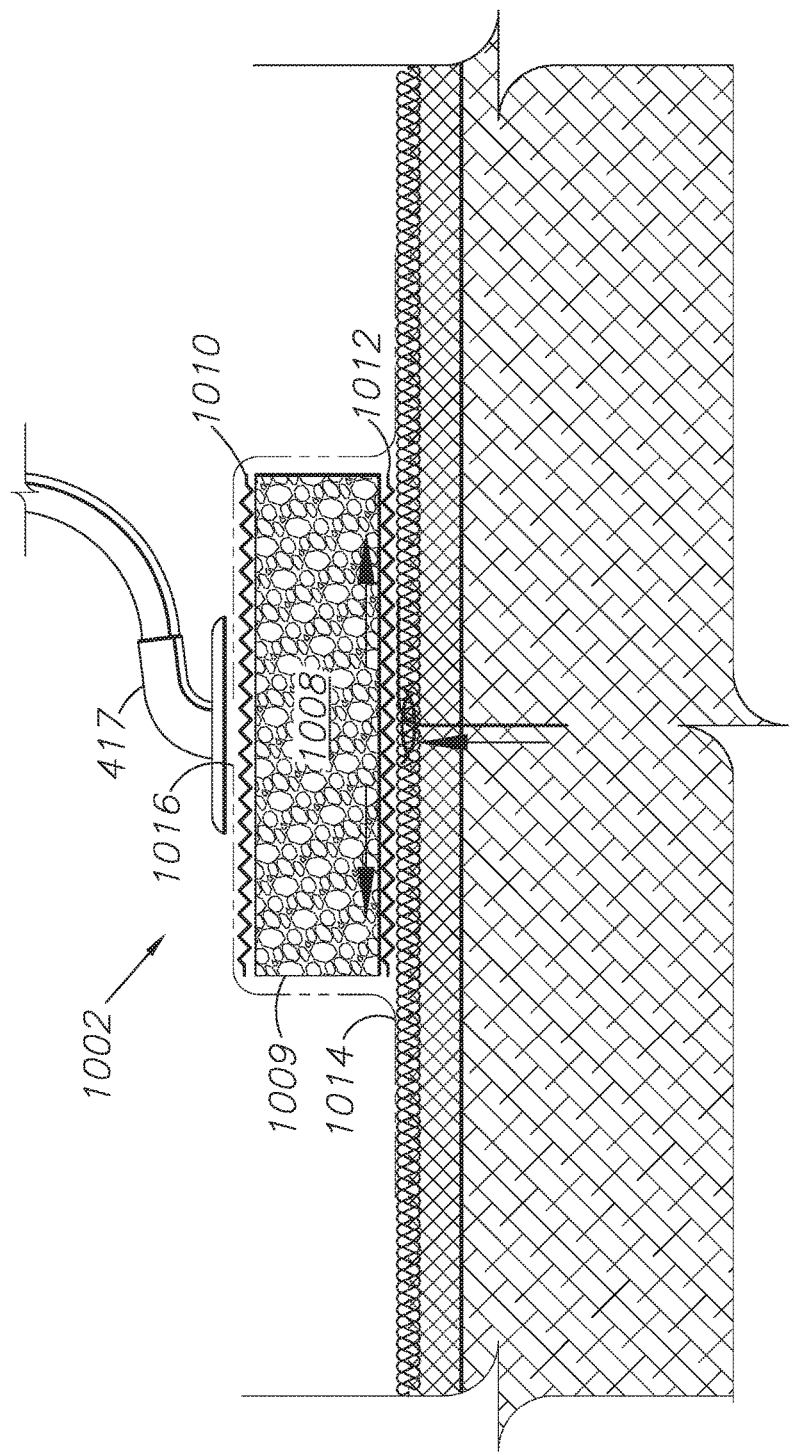
FIG. 48 is a cross-sectional view of a dressing comprising an alternative embodiment of the present invention with upper and lower rayon layers.
Figure 49:
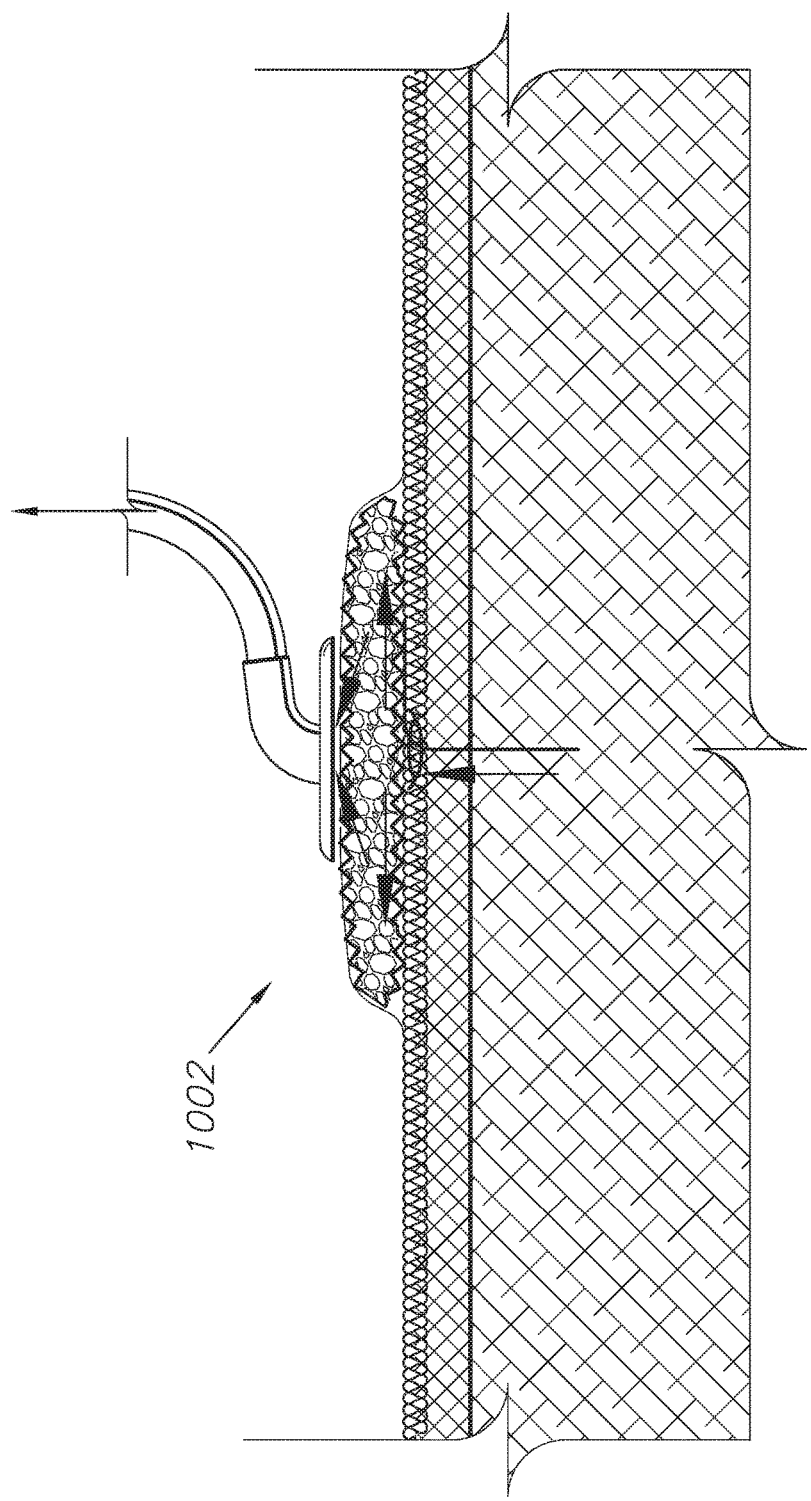
FIG. 49 is a cross-sectional view thereof, with the dressing compressed.

FIGS. 47-49 show another alternative embodiment external dressing 1002. As shown in FIG. 47, a wound 6 can be prepared by placing optional drain strips 1004 between the wound edges and folding the strip distal ends over on the adjacent skin surface. The use of such strips is well-known. A latex version, which is referred to as a Penrose drain, is available from Davol Inc. of Cranston, R.I. A silastic version, which is referred to as a Swanson incision drain, is available from Wright Medical Technology, Inc. of Arlington, Tenn. Alternative deep-wound devices for extracting fluid include drain tubes, such as those described above, and other devices. Alternatively, such drain devices can be omitted from incisions that do not require enhanced drainage. Moreover, the drain strips 1004 can be placed over a strip of liquid transfer liner, such as rayon, "veil" dressing or liner, "N-terface" liner, etc. to increase efficiency and prevent skin maceration.

FIG. 48 shows the dressing 1002, which includes a fluid transfer component 1006 with a reticulated foam core or block 1008 (e.g. polyurethane-ether as described above) with a surface 1009 and distal/upper and proximal/lower wicking material (e.g., rayon or other suitable wicking material) layers 1010, 1012, which can optionally be bonded to or placed loose on the core 1008. A membrane drape 1014 is placed over the fluid transfer component 1006 and releasably adhered to healthy skin adjacent to the incision 6. An elbow coupling 417 is placed over an opening 1016 forming a discharge port in the membrane drape 1014. The coupling 417 is attached to a suction or negative pressure source, also as described above. Upon activation of the negative pressure source, fluid movement tends to be concentrated laterally (horizontally) along the bottom wicking layer 1012 towards the perimeter of the fluid transfer component 1006. The pressure differential between the fluid transfer component 1006 and the ambient atmosphere compresses the core 1008 as shown in FIG. 49. For example, compression in the range of approximately 20% to 80% is feasible. The rayon layers 1010, 1012 are thus drawn into closer proximity, particularly around the perimeter of the fluid transfer component 1006, whereby fluid transfer therebetween is facilitated. Still further, the upper rayon layer 1010 tends to draw laterally inwardly under negative pressure, whereas the lower rayon layer 1012, because of being placed on the skin, tends to retain its original shape and size. The upper rayon layer 110, which is less compressible than the foam core 1008, thus tends to deflect downwardly around its perimeter edges, further facilitating fluid flow to the upper rayon layer 1010 and to the discharge coupling 417. The exposed perimeter edges of the core 1008 facilitate air movement into the core 1008, e.g. through the membrane 1014, which can comprise a semi-permeable material.

Figure 50:
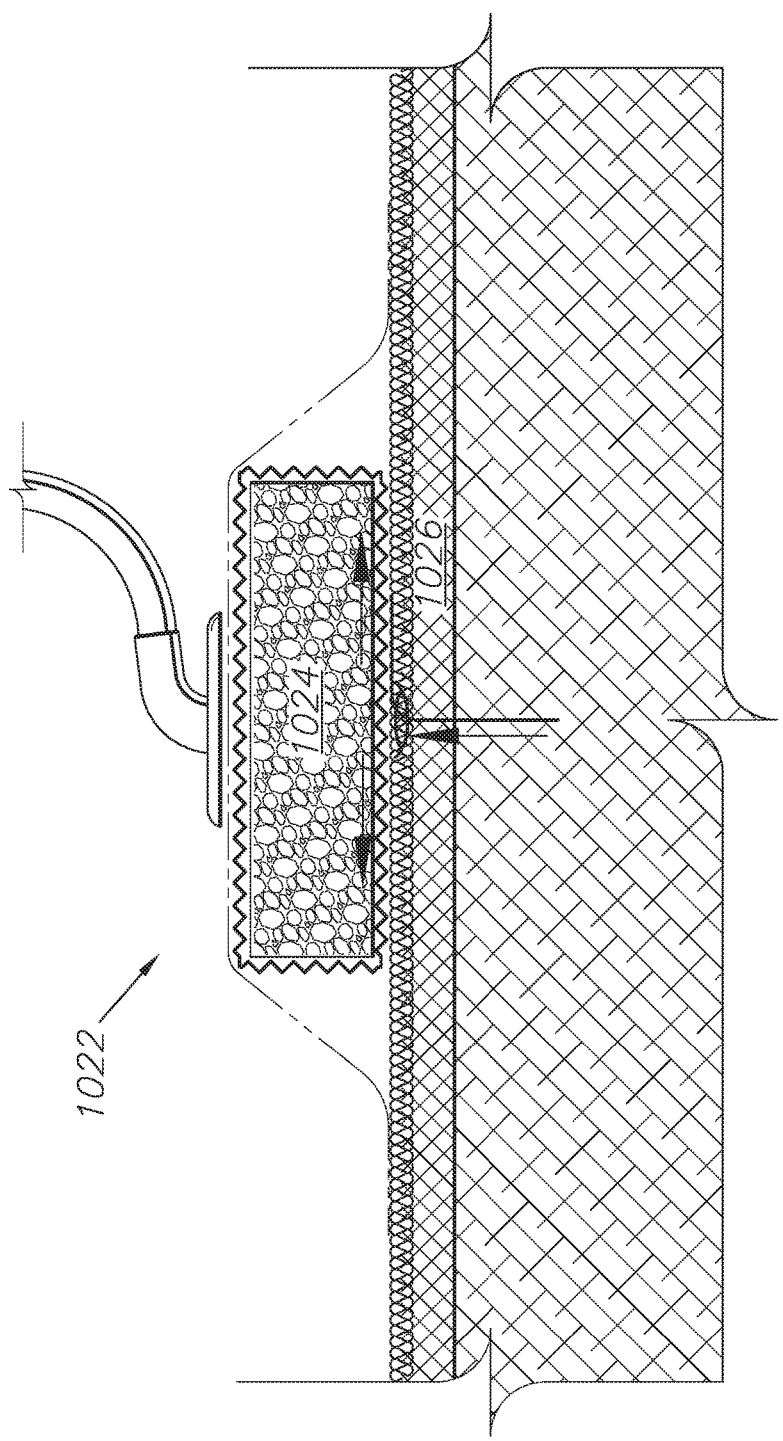
FIG. 50 is a cross-sectional view of a dressing comprising an alternative embodiment of the present invention with a rayon cover enclosing a reticulated foam core.
Figure 51:
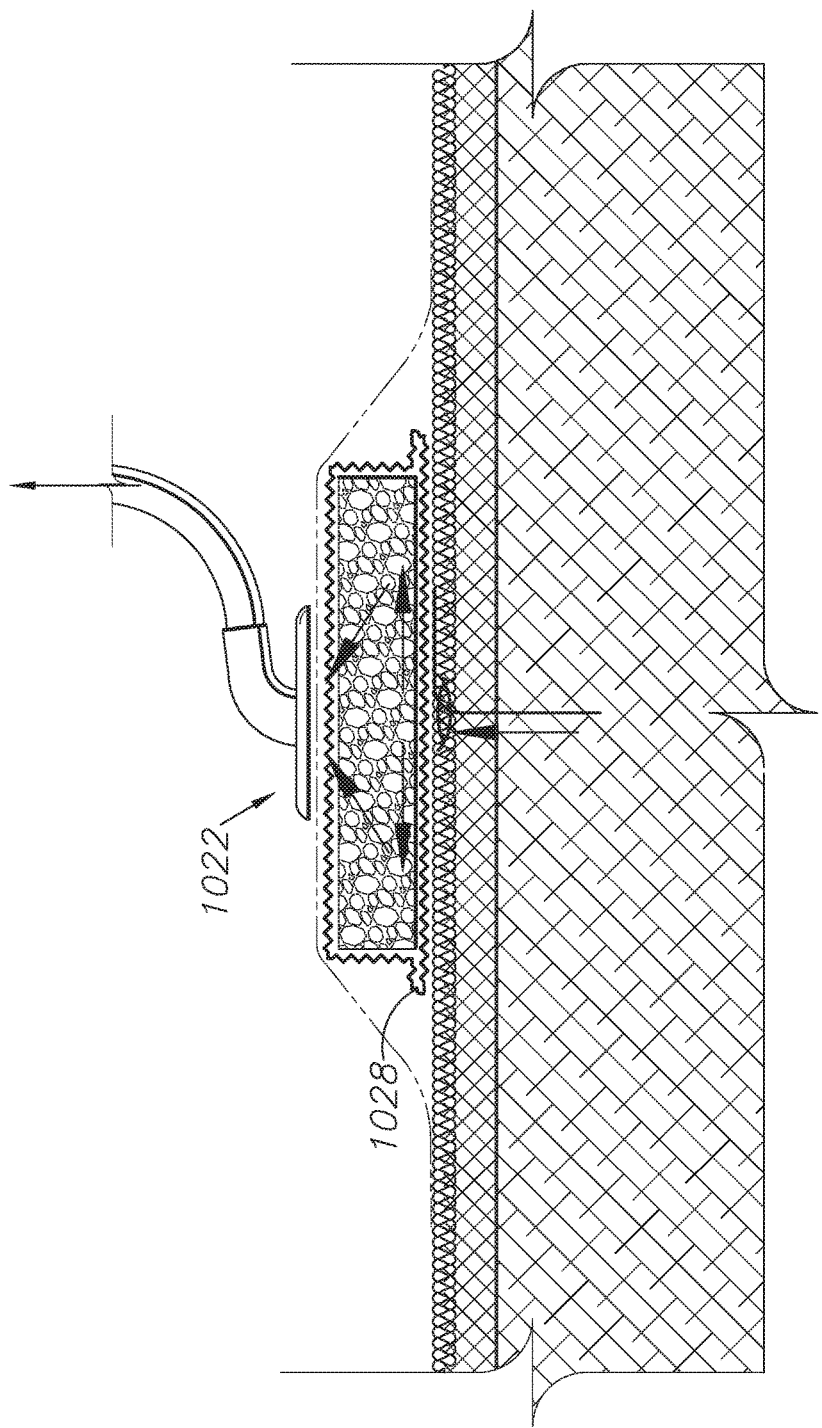
FIG. 51 is a cross-sectional view thereof, with the dressing compressed.

FIGS. 50 and 51 show another alternative embodiment dressing assembly 1022 with a foam core 1024 fully enclosed in a wicking material (e.g. rayon or other suitable wicking material) layer 1026. FIG. 51 shows the dressing 1022 after negative suction pressure is applied, which can cause the rayon layer 1026 to buckle or bunch adjacent to the lower portions of the core perimeter edges, thereby providing an extended, buckled wicking material double-layer rim 1028. The rim 1028 can provide an additional interface with the patient's skin, thereby avoiding or reducing pressure-related problems such as shearing force blistering. The rim 1028 can provide another benefit in the form of enhanced airflow for the drying mode of skin maturation, which is a requirement of a long-term (three days to three weeks) postoperative dressing.

Yet another alternative embodiment dressing system comprises the use of the dressing assembly 1012 during an initial heavy exudative phase, which typically occurs approximately 48-72 hours after a surgery. The dressing 1002 can thereafter be removed and the rayon-enclosed dressing assembly 1022 applied for the long-term (typically about three days to three weeks) postoperative transudative phase. Alternatively, a rayon wicking material layer alone can be applied to continue wicking-assisted fluid drainage of transudate. The tissues are thus stabilized for critical early collagen strength gain and for removing transudate, thereby allowing for "sealing" of the incision 6 and the drain sites, and promoting drying the skin surface.

Figure 52:
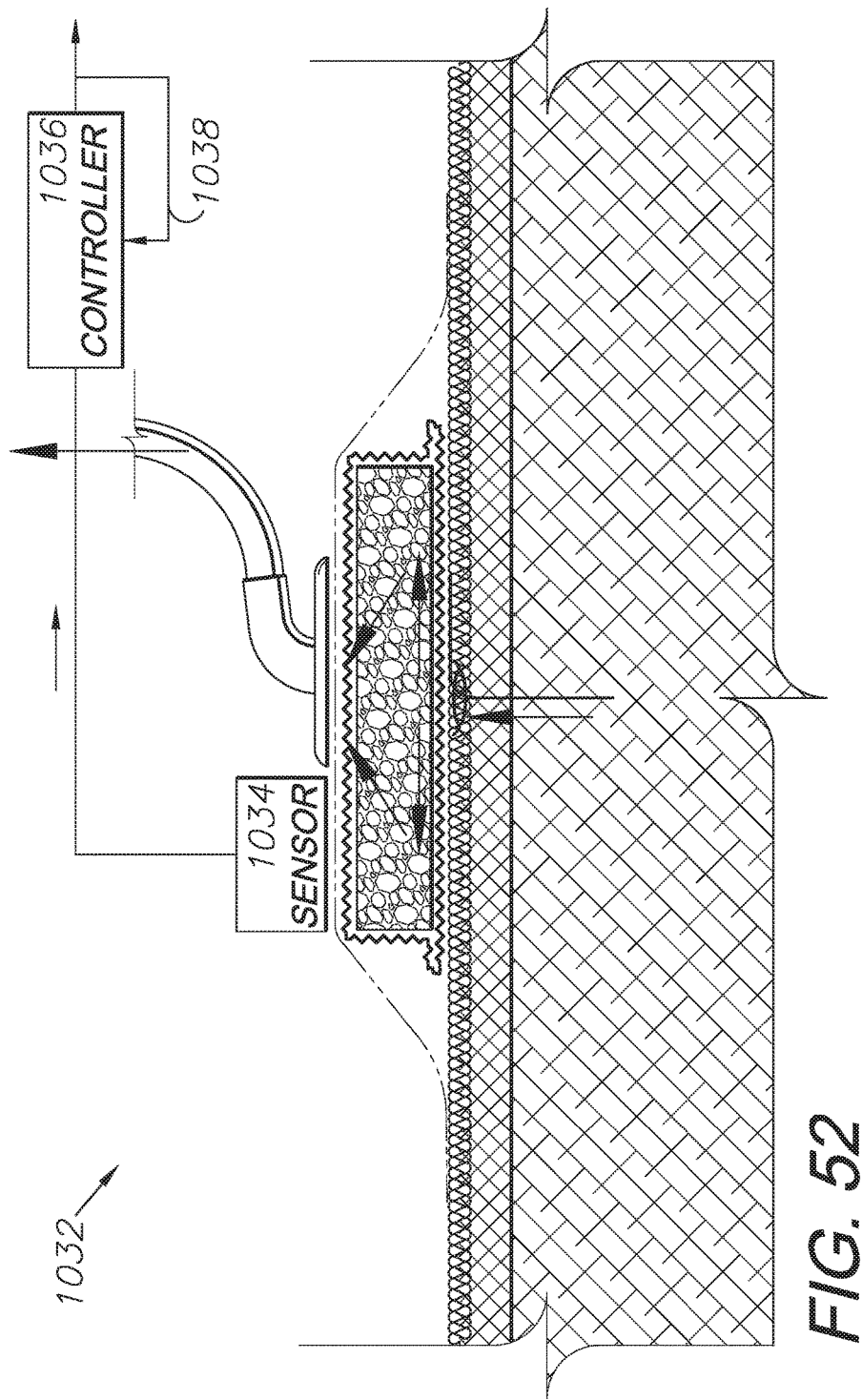
FIG. 52 is a cross-sectional view of a dressing comprising an alternative embodiment of the present invention with a sensor connected to a controller.

FIG. 52 shows yet another embodiment of the wound dressing 1032 with a sensor 1034 in communication with the dressing 1032 and providing an input signal to a controller 1036, which can include a feedback loop 1038 for controlling various operating parameters of a system including the wound dressing 1032. For example, hemoglobin levels can be monitored, as well as pressures, fluid flows, temperatures, patient conditions and various exudate and transudate characteristics.

Figure 53:
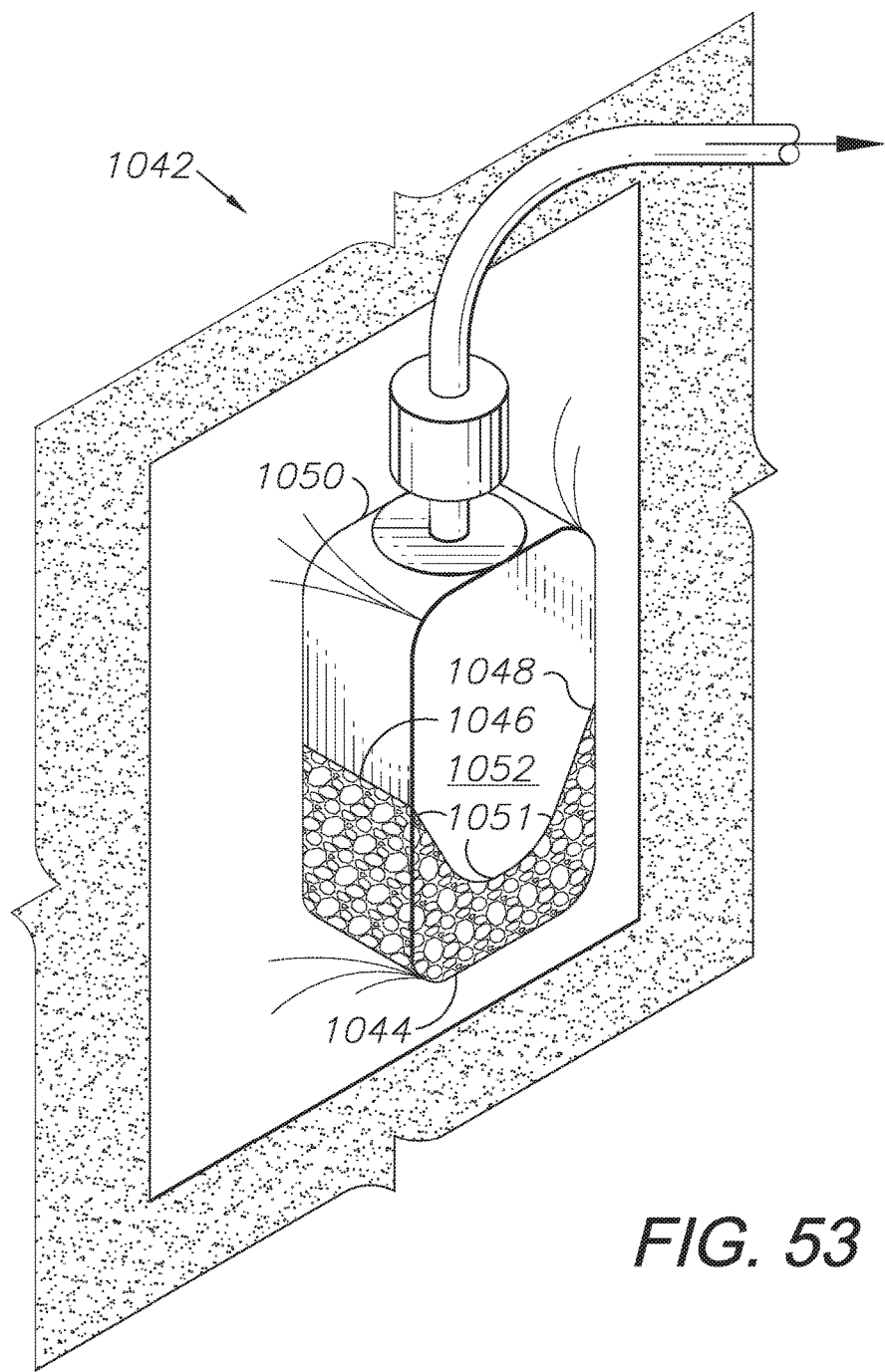
FIG. 53 is a perspective view of an experimental model of the dressing for observing fluid flow therethrough.

FIG. 53 shows an experimental model 1042 of the dressing, which is oriented vertically to model fluid flow in the system. The fluid tends to be present in the areas which are shown at the bottom 1044 and along the sides 1046, 1048 of the reticulated polyurethane foam core 1050 and define a fluid transfer zone 1051. An air entrapment zone 1052, i.e. top and center of the foam core 1050, tends to trap air whereby the fluid tends to be drawn towards the outside edges. The polyurethane ether reticulated foam material thus tends to trap air interiorly and move liquid exteriorly. In this configuration, the break point for the ability to move liquid to the discharge elbow 417 occurs at a liquid volume equal to approximately 10% of the volume of the non-compressed foam core 1050. Liquid absorption in the reticulated foam can be enhanced by coating its passages with protein.

Table I shows the compression effect of the reticulated polyurethane ether foam material under various negative pressure levels.

TABLE I

COMPRESSION EFFECT

|  | VOLUME (CC) | % COMPRESSION |
|---|---|---|
| FOAM BLOCK (DRY) | 283.34 | 15 |
| WITH FILM DRAPE | 258.91 | 68 |
| WITH 50 mm Hg VAC | 58.94 | 73 |
| 100 mm | 49.96 | 73 |
| 150 | 42.41 | 77 |
| BACK TO 100 | 47.71 | 74 |
| AIR RE-EQUILIBRATION | 133.95 | 28 |

Figure 54:
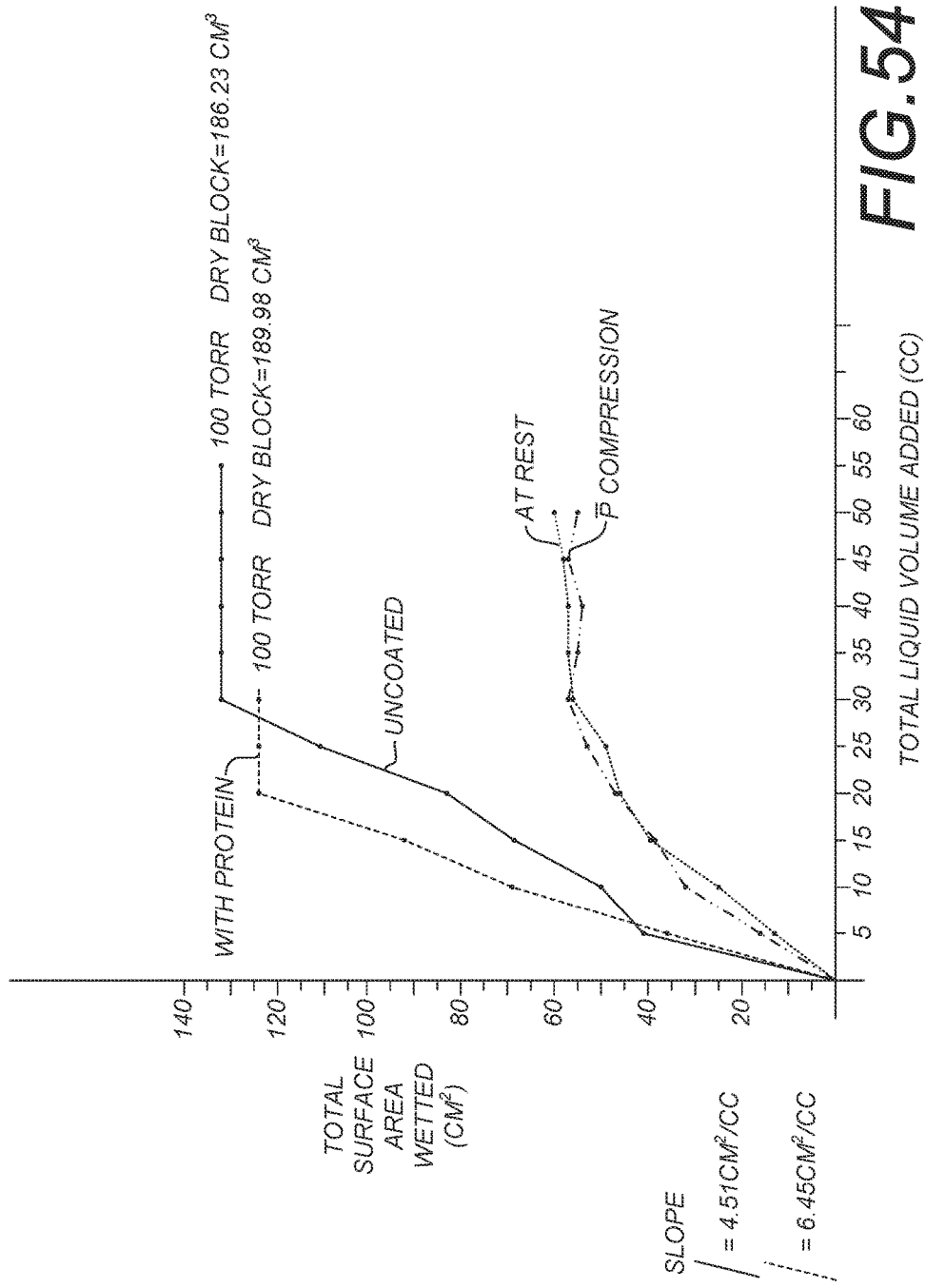
FIG. 54 is a graph showing wetted surface area of the reticulated foam core with respect to liquid volume for different conditions.

FIG. 54 shows the total wetted surface area of the reticulated polyurethane foam as a function of total liquid volume added at different pressures, with both uncoated and protein-coated foam conditions.

Figure 55:
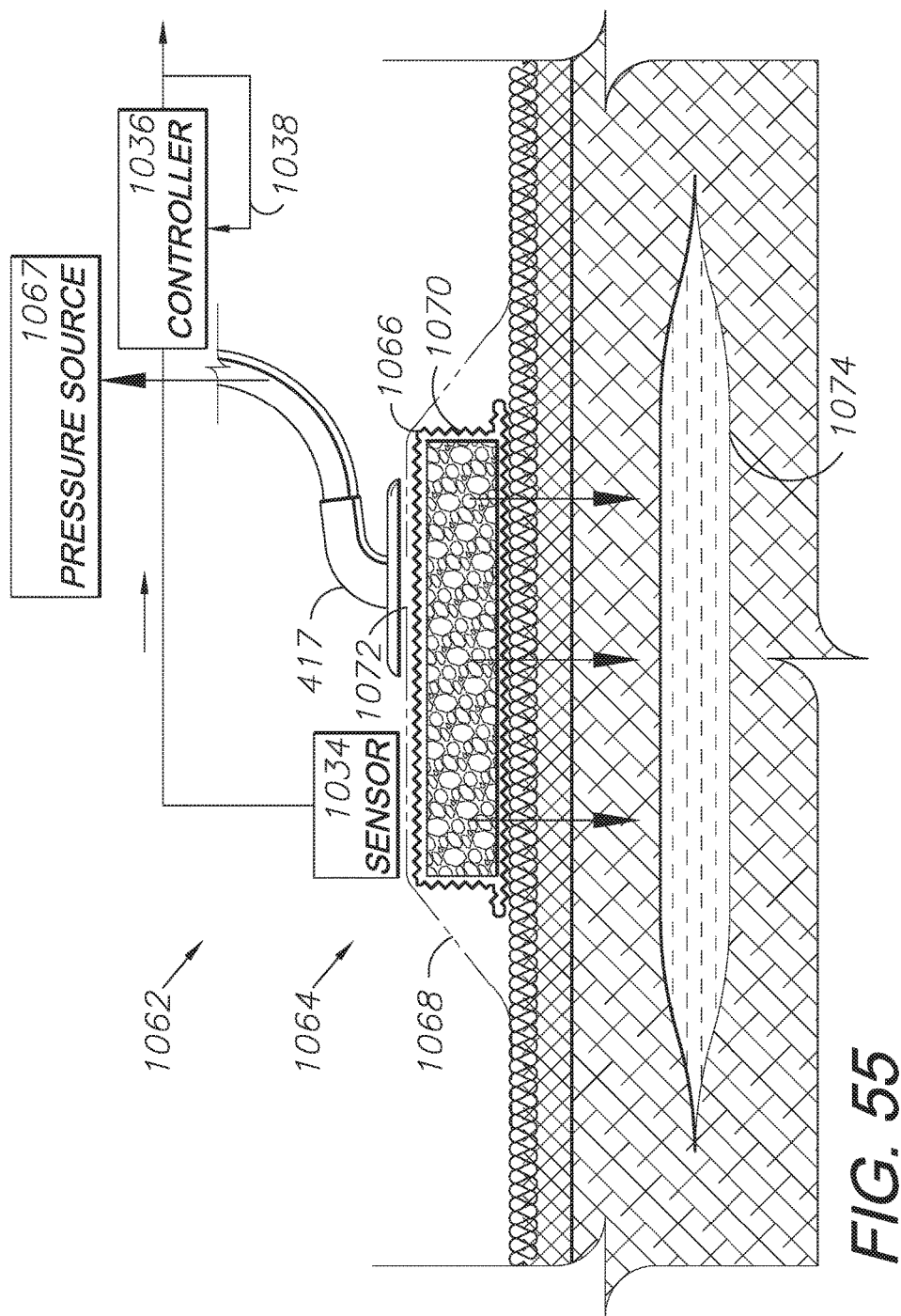
FIG. 55 is a cross-sectional view of a hemostat comprising an alternative embodiment of the present invention.

FIG. 55 shows an active, positive pressure hemostat 1062 comprising an alternative embodiment of the present invention and including a patient interface 1064 with a transfer component 1066 for placement against a patient and an overdrape 1068 placed thereover and fastened to the surrounding skin. The transfer component 1066 can include an optional liner or cover 1070 for direct engagement with the patient's skin if the material comprising a core 1069 is incompatible with direct skin contact. The transfer component 1066 communicates with a pressure source 1067 via an elbow coupling 417 over an opening or discharge port 1072 in the overdrape 1068. Applying negative pressure to the transfer component 1066 results in a positive pressure being applied to the patient's skin via the transfer component 1066. The hemostat 1062 is adapted for providing localized compression to speed resorption of free fluid edema. Applications can include subdermal hemorrhages (e.g. 1074) and free edema resorption in body cavities, internal organs and joints. Other applications can also utilize the active pressure hemostasis device 1062, including poultice-type applications for enhancing absorption of surface-applied pharmaceuticals. As shown, the sensor 1034 and the controller 1036 can monitor various operating parameters for providing automated control, particularly in connection with varying positive pressures exerted by the transfer component 1066.

For example, visible, thermal and infrared indications of subdermal conditions can be detected by the sensor 1034, which outputs corresponding signals for input to the controller 1036. Pressure can be cycled as appropriate, and terminated upon certain predetermined conditions being achieved, e.g. resorption of the free edema corresponding to achieving the treatment objectives.

It is to be understood that while certain embodiments and/or aspects of the invention have been shown and described, the invention is not limited thereto and encompasses various other embodiments and aspects. For example, various other suitable materials can be used in place of those described above. Configurations can also be adapted as needed to accommodate particular applications. Still further, various control systems can be provided and preprogrammed to automatically respond appropriately to different operating conditions. Still further, the systems and methods described above can be combined with various other treatment protocols, pharmaceuticals and devices.

XV. Alternative Embodiment External Dressing Systems

Figure 56:
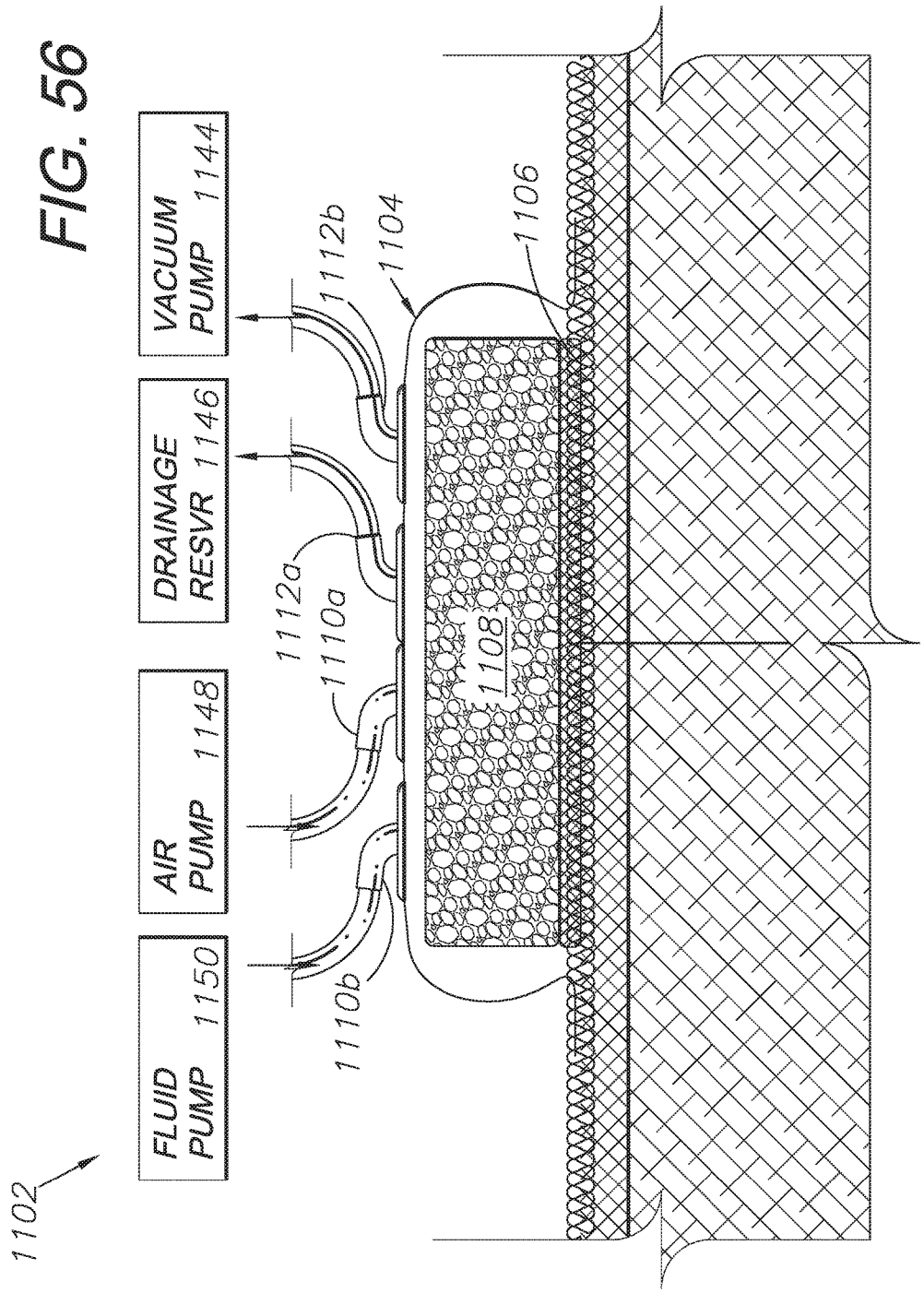
FIG. 56 is a cross-sectional view of a wound dressing system comprising yet another alternative embodiment of the present invention.
Figure 57:
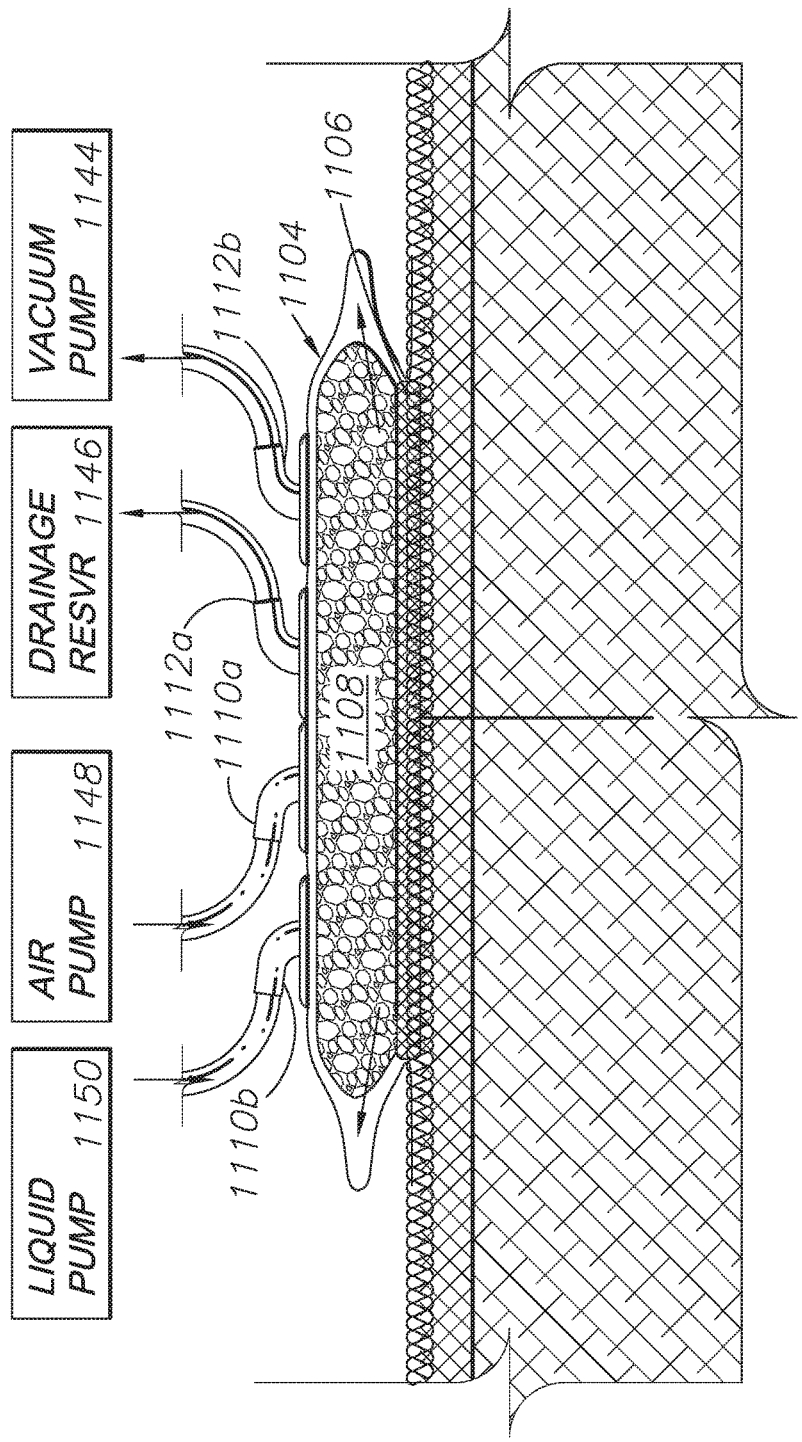
FIG. 57 is a cross-sectional view thereof, shown in a compressed configuration with negative pressure applied.
Figure 58:
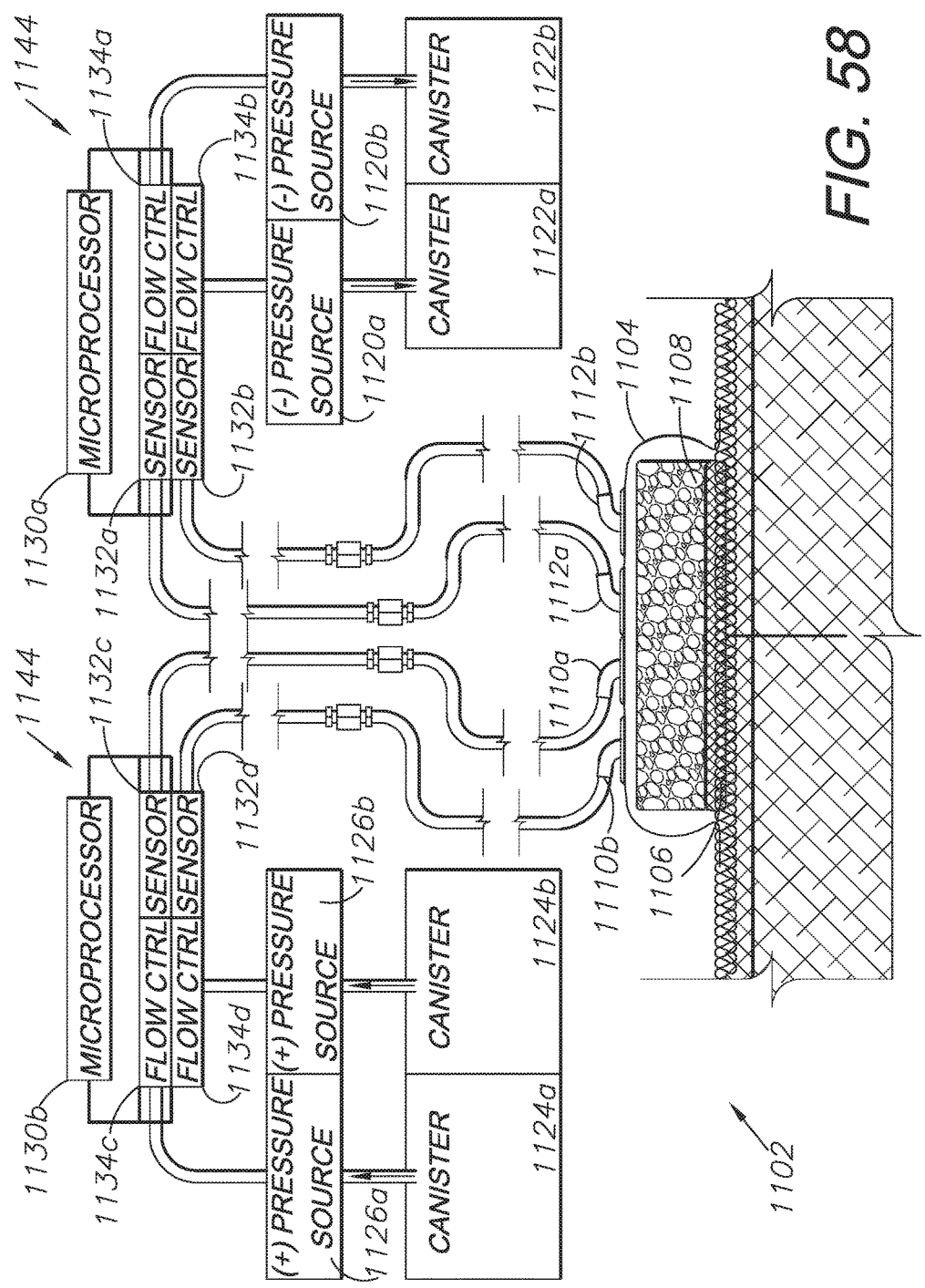
FIG. 58 is another cross-sectional view thereof, showing external components connected to the alternative embodiment wound dressing system.

FIGS. 56-58 show another alternative embodiment external wound dressing system 1102. As shown in FIG. 56, a wound 6 can be prepared by placing a fresh external dressing 1102 onto said wound. Said dressing 1102 promotes healing at three levels of the wound repair continuum: healing (epithelialization) of an open wound, stability of a freshy, recently epithelized but not matured wound, and maintenance of a mature or intact epithelium without breakdown under a dressing. This dressing device 1102 has the unique advantage that it can be applied for a short period of time (days) or left in place without changing for up to six weeks. This is possible because the wound removes old air and liquid from the wound-site and introduces fresh air and liquid to the wound-site to expedite the healing process.

The critical elements for this dressing include a cover layer 1104, a surface-contact layer 1106, a compression core 1108, at least one port 1112b and a vacuum pump 1144. Additional preferred elements include additional ports 1110a,b, 1112a, a drainage reservoir 1146, an air pump 1148, and a liquid pump 1150.

The surface contact layer 1106 is the only layer to directly come into contact with the patient's skin 42. This component must have a weave or pore size small enough to prevent vascular or granulation in-growth so that epithelial migration can proceed beneath it. It should be smooth at a cellular level to minimize deformation and enhance the property of streaming for accelerated epithelial migration. Additionally, this layer must be usable both short term (i.e. changeable without stripping off the underlying early epithelium) and left long term without changing to allow for additional fluid exchange of air passage and water vapor removal to allow drying for epithelial maturation. The preferred embodiment of said surface contact layer 1106 therefore is a material that can wick or move liquids both laterally along and perpendicularly through the thin hydrophobic material of the compression core 1108 located atop said contact layer 1106, while also allowing air to be pulled into or along said contact layer 1106 so that moisture vapor may be pulled out of the layer for epithelium drying. Generally such a material will include the family of closely woven hydrophobic fibers such as nylons, rayons, 'parachute silk' and the available veil and interface dressings and wound contact layers.

The compression core 1108 sits atop said surface contact layer 1106 and these two layers perform the primary tasks associated with this embodiment of an external dressing system 1102. The compression core 1108 must participate in the reciprocal strategy with the contact layer 1106 for fluid management. If the strategy is to pass the exudate and moisture through the contact layer for absorption or removal above, it, than this layer must be capable of that. If the strategy is to move the liquid laterally, than this layer must be capable of dealing with that. This layer must be able to enhance the passive ability of the dressing system to maintain adequate moisture retention in early healing to ensure moist wound healing at the surface and avoid desiccation and then be able to enhance air passage and drying to ensure maturation and drying without moisture retention as healing progresses.

As demonstrated by comparing FIGS. 56 and 57, the unique primary function of the compression core 1108 is to uniformly transfer compression or positive pressure to the wound-site. This layer must be able to distribute vacuum pressure and then transfer it to the surface contact layer 1106. The core 1108 must be able to collapse, without an intervening inter-space, against the surface contact layer 1106, and it must be flexible and able to return to its original size and shape when vacuum pressure is removed. The preferred embodiment for this material is an open-cell hydrophobic foam material which will maximize the above-listed desirable characteristics of said compression core 1108. This material can be integrated with the surface contact layer 1106 in any manner that achieves the moisture management end-points. Other materials may be used instead, such as hydrophobic foam or hodrophilic fiber matrix pads, but these materials are not best suited to fulfill the above requirements.

A cover layer 1104 is present to contain the other components including the compression core 1108 and the surface contact layer 1106. The cover layer 1104 must be of such thinness and flexibility that it can be collapsed completely over the underlying compression core 1108 to transfer atmospheric pressure to all areas of the soft tissue press. The preferred characteristics of the cover layer 1104 include transparency, ability to be used with a medical grade adhesive appropriate for long-term use on intact skin, and a degree of stretch to decrease the lateral traction and blister force on skin in long-term usage, and significant moisture-vapor permeability to prevent masceration of the wound-site.

In a preferred embodiment, numerous ports 1110a,b, 1112a,b are connected to said cover layer 1104, along with at least one mechanical vacuum pump 1144. FIGS. 56-58 demonstrate four ports, two being input ports 1110a,b, and two being exhaust ports 1112a,b. This is the preferred embodiment, but any number of ports can realistically be used. These ports transfer materials to or from the compression core 1108 and provide either positive or negative pressure to the wound-site. The system must have at least an exhaust port 1112b to evacuate air to create a vacuum press force or positive compression force through the cover layer 1104. This pressure is caused by an attached vacuum pump 1144. In a preferred option, an additional exhaust port 1112a is attached to evacuate liquid drainage and moisture from the compression core 1108 and move it to a drainage reservoir 1146 for disposal. The same vacuum pump 1144 can be used to draw out both liquid and air.

A preferred embodiment would additionally have a liquid input port 1110a and an air input port 1110b for the introduction of fresh air and liquid into the compression core 1108 and the surface contact layer 1106. Said liquid and air inputs are provided by an air pump 1148 and a liquid pump 1150 provided with positive pressure. The introduced air induces drying to the epithelial and helps to remove liquid from the wound-site by turning it into vapor to be removed by the vacuum pump 1144. Liquid may be introduced via the liquid input port 1112a for rinsing or introducing dissolved medications and various pharmacologics or beneficial gases or vapors to the wound-site for increased healing speed. An adjustable or controllable air inlet valve and/or computerized flow controller is used to minimize air inflow and enhance the vacuum press effect, moist wound healing process, and exudates extraction. Said valve or flow controller could then be loosened to increase air-flow to promote epithelial drying during maturation.

FIG. 58 shows the connections between said input and output ports 1110a,b, 1112a,b, and the mechanical vacuum pumps 1144. Said vacuum pumps are divided into several components, including a microprocessor 1130, flow sensor 1132, flow control 1134, and either a negative pressure source 1120 or a positive pressure source 1126. Cannisters 1122, 1124 are provided for either containing liquids or gasses to be introduced to the wound-site or for disposal of liquids or gasses removed from said wound site. The liquid input port 1112a is connected to its own flow controller 1134c, sensor 1132c, positive pressure source 1126a, and canister 1124a containing liquids to be introduced to the wound site. Likewise the air input port 1112b is connected to its own flow controller 1134d, sensor 1132d, positive pressure source 1126b, and canister 1124b containing dry air to be applied to the wound site. A separate microprocessor 1130b is used to control these systems from the negative pressure source systems. The exhaust ports 1110a,b also are connected to individual components for removing air and moisture from the compression core 1108, and negative pressure sources 1120a,b for providing the vacuum pressure necessary for compressing said compression core 1108.

The above mentioned components of said external dressing system 1102 combine their separate functions into an integrated system. The preferred embodiment of said system is preassembled and packaged in a range of sizes corresponding to average incision lengths or operative or wound sites known conditions so that the package can be simply opened and applied. Components should also be available separately for customized application.

Figure 59:
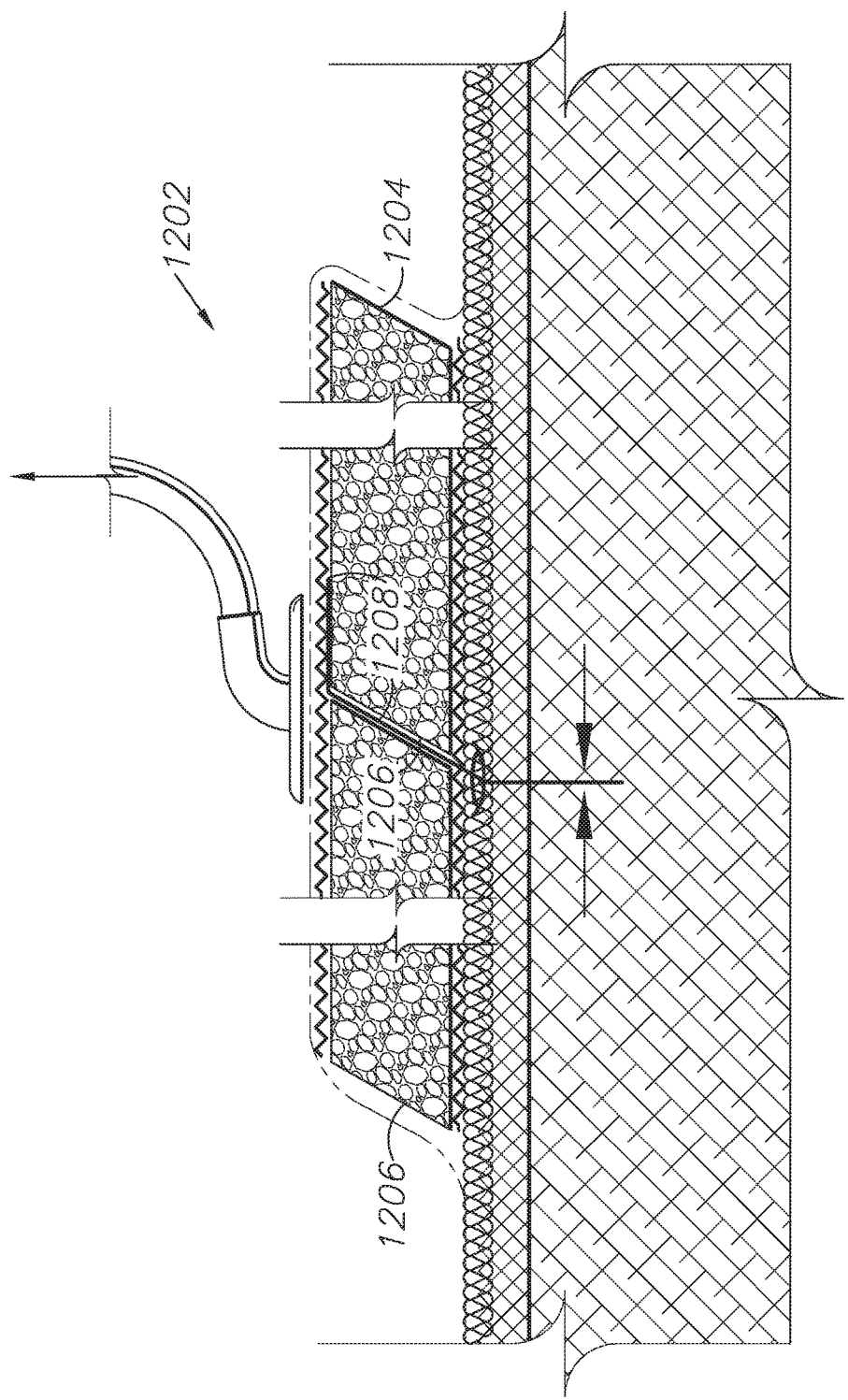
FIG. 59 is a cross-sectional view of a wound dressing system comprising yet another alternative embodiment of the present invention.

FIG. 59 shows yet another alternative embodiment external wound dressing and closure system 1202 with modified foam pieces 1204, which function, inter alia, as fluid transfer components in the system 1202. Each foam piece 1204 includes beveled or angle-cut ends 1206. The foam piece 1204 sides can also be beveled or angle-cut. The foam piece 1204 presents increased surface area at the ends 1206 for enhanced fluid transfer, wicking action and fluid management. Such greater surface area tends to increase the effectiveness of the dressing 1202. Moreover, the foam pieces 1204 are easily customizable and can be cut to desired lengths for particular incisional management applications.

Optionally, a wicking strip 1208 can be placed in the tissue closure over the incision and extended between the foam piece ends 1206 and terminated distally in proximity to a cover(s) over the dressing 1202.

XVI. Bio-Reactor Embodiment

A surface device of the negative pressure variety is sized to be well beyond the boundaries of the bio-reactor to be implanted. For example, if the bio-reactor is 1 in.×1 in.

square, the surface dressing may be 4 in.×4 in. square. But it is to be recognized that there can be a wide variation in these proportions.

First the bio-reactor is implanted—ideally from a distant approach site removing the percutaneous approach from beneath the surface portion of the device. Rolled implantable devices of permanent and biodegradable materials have been previously described so that implantation and addition of cells and solutions can be carried out by needle or catheter, left permanently or removed after instillation. An incision and surgical placement can of course also be utilized.

The dressing of one or more layers of finely woven (minimal interstices size) fabric or of gels or colloid or closely compressed smooth foam with minimal, if any, pore size is placed on the skin. This is covered by a material that serves as manifold and compressible core that produces the closely held compression of the contact layer to the skin. Reticulated open-cell foam is the most commonly used material. This is covered by a drape that either has minimal or a low vapor transmission rate so that a small vacuum source can easily exceed it and produce a continuous collapse of this dressing and the desired compression effect.

This combination of implanted bio-reactor and overlying surface compression device produces a zone with enhanced fluid dynamics that enhances the rates of activity in the bio-reactor. The bio-reactor can be utilized in connection with the wound dressing and incisional management systems and methods described above.

XVII. Further Alternative Embodiments

This principle can be applied not only at skin and underlying surface but internally with internal visceral placement of the bio-reactor and visceral surface placement of the compressive device. Examples would include internal liver implantation of the bio-reactor and surface placement of the compressive device—vacuum being achieved, and internal solutions addition to the implant being achieved by tubing led through the skin surface and controlled exterior to the body. Of course the entire system could be designed to be implanted and self-contained. The implantation and removal process could all be done laparoscopically with minimal incisions.

This same process could be applied to intramural intestinal implantation, or any other hollow viscera, and serosal or external visceral surface compression device. The same approach can be applied to any solid viscera such as spleen and kidney. It can also be applied to muscle and muscular organs such as the heart, fascial linings and any intramuscular implantation.

It is to be understood that the invention can be embodied in various forms, and is not to be limited to the examples discussed above. The range of components and configurations which can be utilized in the practice of the present invention is virtually unlimited.

Having thus described the disclosed subject matter, what is claimed as new and desired to be secured by Letters Patent is:

1. A dressing for promoting healing of a closed, incisional wound with opposed wound edges including:
   a foam core having a perimeter and upper and lower surfaces;
   a fabric wick covering the foam core;
   an overdrape draped over the wick-covered foam core and configured for placement over a patient's skin and around the wound;
   a drain in the overdrape;
   a vacuum configured for applying negative pressure to the wound site, the vacuum connected to the overdrape drain;
   the wick configured for spreading patient fluid from the wound around and through the foam core;
   the vacuum configured for removing patient fluid from the wick and out of the dressing through the drain;
   said overdrape configured for trapping liquid in and around said foam core;
   said overdrape configured for transferring air to said foam core;
   said overdrape including a cover return ring extending outwardly and underneath the foam core; and
   said cover return ring including adhesive for releasably attaching said foam core to the patient's skin around the wound below said foam core perimeter.

2. The wound healing dressing according to claim 1, which includes:
   said foam core including multiple individual pieces with beveled ends.

3. The wound healing dressing according to claim 1, wherein:
   said foam core is configured for being cut to a desired length.

4. The wound healing dressing according to claim 1, wherein:
   said wound healing dressing is configured for side-by-side placement with one or more additional wound healing dressings.

5. The wound healing dressing according to claim 1, further comprising:
   one or more drain strips configured to be located in the wound and fluidically communicate with said wick, said drain strips being made of latex or elastic.

6. The wound healing dressing according to claim 1, which includes:
   said foam core having a first, expanded configuration and a second, compressed configuration;
   said vacuum compressing said foam core from its first configuration to its second, compressed, negative pressure configuration; and
   said foam core perimeter having an outwardly-convex configuration in its second, compressed configuration with said perimeter extending outwardly over said cover return ring whereby said cover return ring reduces the negative pressure applied to the skin surface underlying the return ring.

7. The dressing according to claim 1, which is configured for pressing said opposed wound edges together to promote closure and healing.

8. A dressing for promoting closure and healing of a closed, incisional wound by pressing the opposed wound edges including:
   a foam core having a perimeter and upper and lower surfaces;
   a fabric wick covering the foam core;
   an overdrape draped over the wick-covered foam core and configured for placement over a patient's skin and around the wound;
   a drain in the overdrape;
   a vacuum configured for applying negative pressure to the wound site, the vacuum connected to the overdrape drain;
   the wick configured for spreading patient fluid from the wound around and through the foam core;

the vacuum configured for removing patient fluid from the wick and out of the dressing through the drain;

said overdrape configured for trapping liquid in and around said foam core;

said overdrape configured for transferring air to said foam core;

said overdrape including a cover return ring extending outwardly and underneath the foam core;

said cover return ring including adhesive for releasably attaching said foam core to the patient's skin around the wound below said foam core perimeter; and said foam core is configured for being cut to a desired length.

* * * * *

UNITED STATES PATENT AND TRADEMARK OFFICE
CERTIFICATE OF CORRECTION

PATENT NO. : 10,363,344 B2
APPLICATION NO. : 14/624417
DATED : July 30, 2019
INVENTOR(S) : David S. Zamierowski Page 1 of 1

It is certified that error appears in the above-identified patent and that said Letters Patent is hereby corrected as shown below:

In the Specification

In Column 12, Line 38, please replace the word "intention" with the correct "invention."

In Column 24, Line 29, please replace the word "freshy" with the correct "freshly."

In Column 25, Line 6, please replace the word "than" with the correct "then." Please remove the "," after the word "above" and before the word "it."

In Column 25, Line 30, please replace the word "hodrophilic" with the correct "hydrophobic."

In Column 26, Line 20, please replace the word "cannisters" with the correct "canisters."

Signed and Sealed this
Tenth Day of December, 2019

Andrei Iancu
*Director of the United States Patent and Trademark Office*